United States Patent
Massague et al.

(10) Patent No.: US 11,058,665 B2
(45) Date of Patent: Jul. 13, 2021

(54) METHODS FOR TREATING BRAIN METASTASIS

(71) Applicant: MEMORIAL SLOAN-KETTERING CANCER CENTER, New York, NY (US)

(72) Inventors: Joan Massague, New York, NY (US); Adrienne Boire, New York, NY (US); Qing Chen, Palisades Park, NJ (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/570,180

(22) Filed: Sep. 13, 2019

(65) Prior Publication Data

US 2020/0085781 A1 Mar. 19, 2020

Related U.S. Application Data

(63) Continuation of application No. 15/462,253, filed on Mar. 17, 2017, now Pat. No. 10,413,522, which is a continuation of application No. PCT/US2015/051057, filed on Sep. 18, 2015.

(60) Provisional application No. 62/052,966, filed on Sep. 19, 2014.

(51) Int. Cl.
| | |
|---|---|
| *A61P 35/04* | (2006.01) |
| *A61P 35/00* | (2006.01) |
| *A61K 45/06* | (2006.01) |
| *A61K 31/196* | (2006.01) |
| *A61K 31/555* | (2006.01) |
| *A61K 31/282* | (2006.01) |
| *A61K 31/352* | (2006.01) |
| *A61K 31/7105* | (2006.01) |
| *G01N 33/50* | (2006.01) |

(52) U.S. Cl.
CPC ......... *A61K 31/352* (2013.01); *A61K 31/196* (2013.01); *A61K 31/282* (2013.01); *A61K 31/555* (2013.01); *A61K 31/7105* (2013.01); *A61K 45/06* (2013.01); *A61P 35/00* (2018.01); *A61P 35/04* (2018.01); *G01N 33/5011* (2013.01); *G01N 2333/705* (2013.01)

(58) Field of Classification Search
CPC .. A61K 31/196; A61K 31/555; A61K 31/282; A61K 45/06; A61P 35/00; A61P 35/04; A61P 43/00
See application file for complete search history.

(56) References Cited

U.S. PATENT DOCUMENTS

| | | |
|---|---|---|
| 5,843,989 A | 12/1998 | Vong et al. |
| 5,981,732 A | 11/1999 | Cowsert |
| 6,046,321 A | 4/2000 | Cowsert |
| 6,107,091 A | 8/2000 | Cowsert |
| 6,211,211 B1 | 4/2001 | Chan et al. |
| 6,251,931 B1 | 6/2001 | Boger et al. |
| 6,365,354 B1 | 4/2002 | Bennett et al. |
| 6,410,323 B1 | 6/2002 | Roberts et al. |
| 6,506,559 B1 | 1/2003 | Fire et al. |
| 6,566,131 B1 | 5/2003 | Cowsert |
| 6,566,135 B1 | 5/2003 | Watt |
| 6,573,099 B2 | 6/2003 | Graham |
| 6,770,633 B1 | 8/2004 | Robbins et al. |
| 7,632,866 B2 | 12/2009 | Attali et al. |
| 7,704,946 B2 | 4/2010 | Wang |
| 9,840,533 B2 | 12/2017 | Patel et al. |
| 10,413,522 B2 * | 9/2019 | Massague ............ A61K 31/282 |
| 2009/0142295 A1 | 6/2009 | Becker |
| 2011/0172188 A1 | 7/2011 | Mouthon et al. |
| 2011/0262442 A1 | 10/2011 | Hamilton et al. |
| 2013/0281524 A1 * | 10/2013 | Blower .................. A61P 19/02 514/456 |

FOREIGN PATENT DOCUMENTS

| | | |
|---|---|---|
| EP | 2252320 A2 | 11/2010 |
| EP | 2510939 A1 | 10/2012 |
| JP | 2012-502082 A | 1/2012 |
| JP | 2013-512887 A | 4/2013 |
| JP | 2016-535006 A | 11/2016 |
| WO | WO 1999/026584 A2 | 6/1999 |
| WO | WO 1999/032619 A1 | 7/1999 |
| WO | WO 2001/036646 A1 | 5/2001 |

(Continued)

OTHER PUBLICATIONS

Chen et al., "Carcinoma—astrocyte gap junctions promote brain metastasis by cGAMP transfer", 2016, Nature, 533(7604), pp. 493-498 (Year: 2016).*
Kim et al., "Tonabersat Prevents Inflammatory Damage in the Central Nervous System by Blocking Connexin43 Hemichannels", 2017, Neurotherapeutics, 14(4), pp. 1148-1165. (Year: 2017).*
U.S. Appl. No. 15/462,253, (U.S. Pat. No. 10,413,522), filed Mar. 17, 2017 (Sep. 17, 2019).
Ablasser et al., "Cell intrinsic immunity spreads to bystander cells via the intercellular transfer of cGAMP," Nature 503(7477):530-534 (2013).

(Continued)

*Primary Examiner* — My-Chau T. Tran
(74) *Attorney, Agent, or Firm* — Baker Botts L.L.P.

(57) ABSTRACT

The present invention relates to methods for treating brain metastasis by inhibiting gap junction functionality. It is based, at least in part, on the discovery that cancer cells expressing Protocadherin 7 and Connexin 43 form gap junctions with astrocytes that promote the growth of brain metastases, and that inhibition of Protocadherin 7 and/or Connexin 43 expression in cancer cells reduce progression of brain metastases. It is further based on the discovery that treatment with gap junction inhibitors tonabersat and meclofenamate inhibited progression of brain metastatic lesions and enhanced the anti-cancer activity of the conventional chemotherapeutic agent, carboplatin.

20 Claims, 16 Drawing Sheets

Figure 5A:
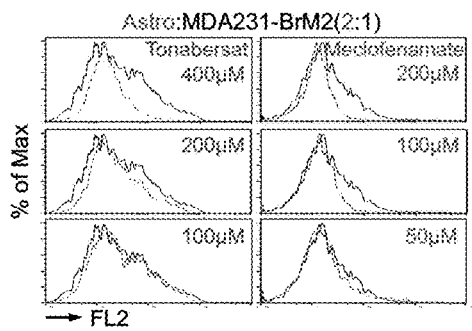
Figure 5B:
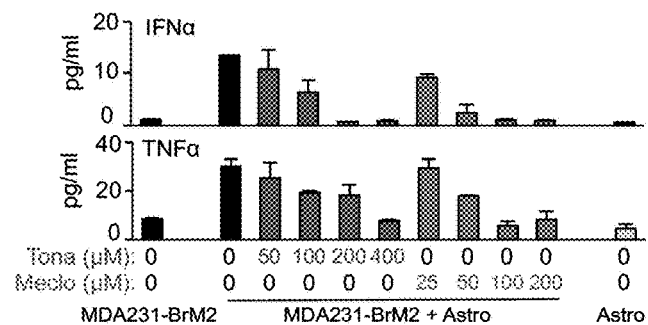

Specification includes a Sequence Listing.

(56) References Cited

FOREIGN PATENT DOCUMENTS

| WO | WO 2001/068836 A2 | 9/2001 |
|---|---|---|
| WO | WO 2009/085274 A2 | 7/2009 |
| WO | WO 2010/025272 A1 | 3/2010 |
| WO | WO 2011/067607 A1 | 6/2011 |
| WO | WO 2014/129914 A1 | 8/2014 |
| WO | WO 2015/057862 A1 | 4/2015 |

OTHER PUBLICATIONS

Anders et al., "Count-based differential expression analysis of RNA sequencing data using R and Bioconductor," Nat Protocols 8(9): 1765-1786 (2013).
Axelsen et al., "Managing the complexity of communication: regulation of gap junctions by post-translational modification," Front Pharmacol 4: 130 (2013).
Bartzatt, "Anti-Inflammatory Drugs and Prediction of New Structures by Comparative Analysis," Anti-Inflamm & Anti-Allergy Agents Med Chem 11:151-160 (2012).
Beahm et al., "Mutation of a Conserved Threonine in the Third Transmembrane Helix of α- and β-Connexins Creates a Dominant-negative Closed Gap Junction Channel," J. Biol. Chem 281(12):7994-8009 (2006).
Bennett et al., "Gap Junctions, Electrotonic Coupling, and Intercellular Communication," Neurosci Res Program Bull 16(3):373-486 (1978).
Boehm et al., "Integrative Genomic Approaches Identify IKBKE as a Breast Cancer Oncogene," Cell 129:1065-1079 (2007).
Bos et al., "Genes that mediate breast cancer metastasis to the brain," Nature 459(7249):1005-1009 (2009).
Bos et al., "Modeling metastasis in the mouse," Curr Opin Pharmacol 10(5):571-577 (2010).
Bradley et al., "Diffusion-Weighted MRI Used to Detect in Vivo Modulation of Cortical Spreading Depression: Comparison of Sumatriptan and Tonabersat," Exp Neuro 172:342-353 (2001).
Brummelkamp et al., "Stable suppression of tumorigenicity by virus-mediated RNA interference," Cancer Cell 2:243-247 (2002).
Cai et al., "Gap junctional communication and the tyrosine phosphorylation of connexin 43 in interaction between breast cancer and endothelial cells," Int J Mol Med 1:273-278 (1998).
Cai et al., "The cGAS-cGAMP-STING Pathway of Cytosolic DNA Sensing and Signaling," Mol Cell 54:289-296 (2014).
Chambers et al., "Dissemination and Growth of Cancer Cells in Metastatic Sites," Nat Rev Cancer 2:563-572 (2002).
Chan et al., "Identification of (−)-cis-6-Acetyl-4S-(3-Chloro-4-Fluoro-Benzoylamino)-3,4-Dihydro-2,2-Dimethyl-2H-Benzo[b]Pyran-3S-ol as a Potential Antimigraine Agent," Bioorg Med Chem Lett 9:285-290 (1999).
Dahl et al., "Attempts to Define Functional Domains of Gap Junction Proteins with Synthetic Peptides," Biophys. J ., 67:1816-1822 (1994).
Dahlof et al., "Efficacy and safety of tonabersat, a gap junction modulator, in the acute treatment of migraine: a double-blind, parallel-group, randomized study," Cephalalgia 29(Suppl. 2):7-16 (2009).
Damodaram et al., "Tonabersat Inhibits Trigeminal Ganglion Neuronal-Satellite Glial Cell Signaling," Headache 49:5-20 (2009).
Danesh-Meyer et al., "Connexin43 mimetic peptide reduces vascular leak and retinal ganglion cell death following retinal ischaemia," Brain 135:506-520 (2012).
DeAngelis et al., "Intracranial Metastasis," Neurologic Complications of Cancer, pp. 141-274 (2009).
Deeken et al., "The Blood-Brain Barrier and Cancer: Transporters, Treatment, and Trojan Horses," Clin Cancer Res 13(6):1663-1674 (2007).
Eichler et al., "The biology of brain metastases-translation to new therapies," Nat Rev Clin Oncol 8(6):344-356 (2011).
Elbashir et al., "RNA interference is mediated by 21-and 22-nucleotide RNAs," Genes & Development 15:188-200 (2001).

Eugenin et al., "The Role of Gap Junction Channels During Physiologic and Pathologic Conditions of the Human Central Nervous System," J. Neuroimmune Pharmacol 7(3):499-518 (2012).
Evans et al., "Connexin mimetic peptides: specific inhibitors of gap junctional intercellular communication," Biochem. Soc. Trans., 29(4):606-612 (2001).
Gaspar et al., "Limited-Stage Small-Cell Lung Cancer (stages I-III): Observations from the National Cancer Data Base," Clin Lung Cancer 6(6):355-360 (2005).
Gaspar et al., "Time from Treatment to Subsequent Diagnosis of Brain Metastases in Stage III Non-Small-Cell Lung Cancer: a Retrospective Review by the Southwest Oncology Group," J Clin Oncol 23:2955-2961 (2005).
Gaspar et al., "Validation of the RTOG Recursive Partitioning Analysis (RPA) Classification for Brain Metastases," Int. J. Radiat Oncol Biol. Phys. 47(4):1001-1006 (2000).
Gatza et al., "A pathway-based classification of human breast cancer," PNAS USA 107(15):6994-6999 (2010).
Gavrilovic et al., "Brain metastases: epidemiology and pathophysiology," J Neuro-Oncology 75:5-14 (2005).
Gilula et al., "Metabolic Coupling, Ionic Coupling and Cell Contacts," Nature 235:262-265 (1972).
Goadsby et al., "Randomized, double-blind, placebo-controlled, proof-of-concept study of the cortical spreading depression inhibiting agent tonabersat in migraine prophylaxis," Cephalalgia 29:742-750 (2009).
Goldberg et al., "Selective transfer of endogenous metabolites through gap junctions composed of different connexins," Nat Cell Biol. 1:457-459 (1999).
Gupta et al., "Mediators of vascular remodelling co-opted for sequential steps in lung metastasis," Nature 446:765-770 (2007).
Hannon, "RNA interference," Nature 418:244-251 (2002).
Harks et al., "Fenamates: A Novel Class of Reversible Gap Junction Blockers," J. Pharmacol Exp. Ther 298(3):1033-1041 (2001).
Harks et al., "Fenannates: A Novel Class of Reversible Gap Junction Blockers," 2001, Journal of Pharmacology and Experimental Therapeutics, 298(3), pp. 1033-1041.
Haydon et al., "How Do Astrocytes Participate in Neural Plasticity?" Cold Spring Harb Perspect Biol 7:a020438 (2015).
Heiman et al., "Development of a BACarray translational profiling approach for the molecular characterization of CNS cell types," Cell 135(4):738-748 (2008).
Herdon et al., "Characterization of the binding of [3H]-SB-204269, a radiolabelled form of the new anticonvulsant SB-204269, to a novel binding site in rat brain membranes," Br J Pharmacol 121:1687-1691 (1997).
Heyn et al., "In Vivo MRI of Cancer Cell Fate at the Single-Cell Level in a Mouse Model of Breast Cancer Metastasis to the Brain," Magnetic Reson Med 56:1001-1010 (2006).
Hirano et al., "The Cadherin Superfamily in Neural Development: Diversity, Function and Interaction with Other Molecules," Front Biosci 8:d306-356 (2003).
Holder et al., "Gap Junction Function and Cancer," Cancer Res 53:3475-3485 (1993).
Hsu et al., "Cadherin repertoire determines partner-specific gap junctional communication during melanoma progression," J Cell Science 113:1535-1542 (2000).
International Search Report dated Jan. 5, 2016 in International Application No. PCT/US15/51057.
Jin et al., "Effects of meclofenamic acid on limbic epileptogenesis in mice kindling models," Neuroscience Lett 543:110-114 (2013).
Joyce et al., "Microenvironmental regulation of metastasis," Nat Rev Cancer 9(4):239-252 (2009).
Juszczak et al., "Properties of gap junction blockers and their behavioural, cognitive and electrophysiological effects: Animal and human studies," Prog Neuro-Psychopharmacol Biol Psychiatry 33:181-198 (2009).
Juul et al., "Quantitative Determination of Gap Junction Intercellular Communication Using Flow Cytometric Measurement of Fluorescent Dye Transfer," Cell Adhes Commun 7(6):501-512 (2000).
Kienast et al., "Real-time imaging reveals the single steps of brain metastasis formation," Nat Med 16:116-122 (2010).

(56) References Cited

OTHER PUBLICATIONS

Kim et al., "Astrocytes Upregulate Survival Genes in Tumor Cells and Induce Protection from Chemotherapy," Neoplasia 13(3):286-298 (2011).
Kim et al., "Spatiotemporal Expression Pattern of Non-Clustered Protocadherin Family Members in the Developing Rat Brain," Neuroscience 147:996-1021 (2007).
Kim et al., "TopHat2; accurate alignment of transcriptomes in the presence of insertions, deletions and gene fusions," Genome Biology 14:R36 (2013).
Li et al., "Elevated PLGF contributes to small-cell lung cancer brain metastasis," Oncogene 32:2952-2962 (2013).
Li et al., "Up-Regulation of the Gap Junction Intercellular Communication by Tea Polyphenol in the Human Metastatic Lung Carcinoma Cell Line," 2012, Journal of Cancer Therapy, 3(1), pp. 64-70.
Lim et al., "Updates on the Management of Breast Cancer Brain Metastases," Oncology 28(7):572-578 (2014).
Lorger et al., "Capturing Changes in the Brain Microenvironment during Initial Steps of Breast Cancer Brain Metastasis," Am J Pathol 176(6):2958-2971 (2010).
Loscher et al., "Drug Resistance in Brain Diseases and the Role of Drug Efflux Transporters," Nat Rev Neurosci 6:591-602 (2005).
Love et al., "Moderated estimation of fold change and dispersion for RNA-seq data with DESeq2," Genome Biology 15:550 (2014).
Luker et al., "Kinetics of regulated protein-protein interactions revealed with firefly luciferase complementation imaging in cells and living animals," PNAS USA 101(33):12288-12293 (2004).
MaassenVanDenBrink et al., "The potential anti-migraine compound SB-220453 does not contract human isolated blood vessels or myocardium; a comparison with sumatriptan," Cephalalgia 20:538-545 (2000).
Maher et al., "Brain Metastasis: Opportunities in Basic and Translational Research," Cancer Res 69:6015-6020 (2009).
McManus et al., "Small Interfering RNA-Mediated Gene Silencing in T Lymphocytes," J. Immunol 169:5754-5760 (2002).
Miyamoto et al., "Heparin-binding epidermal growth factor-like growth factor as a novel targeting molecule for cancer therapy," Cancer Sci 97(5):341-347 (2006).
Nguyen et al., "WNT/TCF signaling through LEF1 and HOXB9 mediates lung adenocarcinoma metastasis," Cell 138:51-62 (2009).
Nilsen et al., "Antiepileptic Effect of Gap junction Blockers in a Rat Model of Refractory Focal Cortical Epilepsy," Epilepsia 47(7):1169-1175 (2006).
Noy et al., "Tumor-associated macrophages: from mechanisms to therapy," Immunity 41:49-61 (2014).
Oberheim et al., "Heterogeneity of Astrocytic Form and Function," Methods Mol. Biol. 814:23-45 (2012).
Oshima, "Structure and Closure of Connexin Gap Junction Channels," FEBS Lett 588:1230-1237 (2014).
Oviedo-Orta et al., "Immunoglobulin and cytokine expression in mixed lymphocyte cultures is reduced by disruption of gap junction intercellular communication," The FASEB Journal 15(3):768-774 (2001).
Patel et al., "DNA-triggered innate immune responses are propagated by gap junction communication," PNAS USA 106(31):12867-12872 (2009).
Pekny et al., "Astrocyte Activation and Reactive Gliosis," Glia 50:427-434 (2005).
Pitz et al., "Tissue concentration of systemically administered antineoplastic agents in human brain tumors," J Neurooncol 104(3):629-638 (2011).
Pollmann et al., "Connexin 43 mediated gap junctional communication enhances breast tumor cell diapedesis in culture," Breast Cancer Res 7(4):R522-R534 (2005).
Qing et al., "Carcinoma-astrocyte gap junctions promote brain metastasis by cGAMP transfer," 2016, Nature, 533(7604), pp. 493-498.

Read et al., "Cortical spreading depression produces increased cGMP levels in cortex and brain stem that is inhibited by tonabersat (SB-220453) but not sumatriptan," Brain Res 891:69-77 (2001).
Read et al., "SB-220453, a potential novel antimigraine agent, inhibits nitric oxide release following induction of cortical spreading depression in the anaesthetized cat," Cephalalgia 20:92-99 (2000).
Reagan-Shaw et al., "Dose translation from animal to human studies revisited," The FASEB Journal 22(3):659-661 (2007).
Rongvaux et al., "Apoptotic caspases prevent the induction of type I interferons by mitochondrial DNA," Cell 159(7):1563-1577 (2014).
Sarrouilhe et al., "Involvement of gap junction channels in the pathophysiology of migraine with aura," Front Physiol 5:78 (2014).
Sharma et al., "Functional effects of protein kinases and peroxynitrite on cardiac carnitine palmitoyltransferase-1 in isolated mitochondria," Mol. Cell Biochem 337:223-237 (2010).
Silberstein et al., "Tonabersat, a gap junction modulator: efficacy and safety in two randomized, placebo-controlled, dose-ranging studies of acute migraine," Cephalalgia 29(Suppl. 2):17-27 (2009).
Smith et al., "Repetitive cortical spreading depression in a gyrencephalic feline brain: inhibition by the novel benzoylamino-benzopyran SB-220453," Cephalalgia 20:546-553 (2000).
Solan et al., "Connexin 43 Phosphorylation—Structural Changes and Biological Effects," Biochem J. 419(2):261-272 (2009).
Soriano-Hernandez et al., "Antitumor effect of meclofenamic acid on human androgen-independent prostate cancer: a preclinical evaluation," (2012), Int. Urol. Nephrol., 44(2), pp. 471-477.
Stetson et al., "Recognition of Cytosolic DNA Activates an IRF3-Dependent Innate Immune Response," Immunity 24:93-103 (2006).
Stoletov et al., "Role of connexins in metastatic breast cancer and melanoma brain colonization," J Cell Sci 126(4):904-913 (2013).
Taimur et al., "Treatment Options for Brain Metastases in Patients with Non-small-cell Lung Cancer," Curr Oncol Rep 5:342-346 (2003).
Theis et al., "Connexin-based intercellular communication and astrocyte heterogeneity," Brain Res 1487:88-98 (2012).
Tuschl et al., "Targeted mRNA degradation by double-stranded RNA in vitro," Genes & Development 13:3191-3197 (1999).
Upton et al., "Profile of SB-204269, a mechanistically novel anticonvulsant drug, in rat models of focal and generalized epileptic seizures," Br J Pharmacol 121:1679-1686 (1997).
Valiente et al., "Serpins Promote Cancer Cell Survival and Vascular Cooption in Brain Metastasis," Cell 156(5):1002-1016 (2014).
Wilson et al., "Lentiviral Delivery of RNAi for In Vivo Lineage-Specific Modulation of Gene Expression in Mouse Lung Macrophages," Mol Ther 21(4):825-833 (2013).
Winder et al., "Experimental Observations on Flufenamic, Mefenamic, and Meclofenamic Acids," Rheumatology VIII(Suppl_1):7-49 (1966).
Winslow et al., "Suppression of Lung Adenocarcinoma Progression by Nkx2-1," Nature 473(7345):101-104 (2011).
Wu et al., "Cyclic-GMP-AMP is an Endogenous Second Messenger in Innate Immune Signaling by Cytosolic DNA," Science 339(6121) (2013).
Xing et al., "Reactive astrocytes promote the metastatic growth of breast cancer stem-like cells by activating Notch signalling in brain," EMBO Mol Med 5:384-396 (2013).
Yagi et al., "Cadherin superfamily genes: functions, genomic organization, and neurologic diversity," Genes Dev 14:1169-1180 (2000).
Yoshida et al., "Cloning, Expression Analysis, and Chromosomal Localization of BH-Protocadherin (PCDH7), a Novel Member of the Cadherin Superfamily," Genomics 49:458-461 (1998).
YoshStelzer, "Epidemiology and prognosis of brain metastases," Surg Neuro Int 4:S192-S202 (2013).
Zhang et al., "Differential Permeability of the Blood-Brain Barrier in Experimental Brain Metastases Produced by Human Neoplasms Implanted into Nude Mice," Am J Pathol 141(5):1115-1124 (1992).
Zhang et al., "Gold nanoparticles as a contrast agent for in vivo tumor imaging with photoacoustic tomography," Nanotechnology 20:395102 (2009).
Zhang et al., "Selection of Bone Metastasis Seeds by Mesenchymal Signals in the Primary Tumor Stroma," Cell 154(5):1060-1073 (2013).

(56) References Cited

OTHER PUBLICATIONS

Guo et al., cGAMP: A New Mammalian Second Messenger, Progress in Biochemistry and Biophysical, 40, 6, 520-523 (2013).
Li et al., "Protocadherin-7 induces bone metastasis of breast cancer," Biochemical and Biophysical Research Communications, 436, 3, 486-490, doi: 10.1016/j.bbrc.2013.05.131 (2013).
Maeda, "Structure and function of human gap junction channel," Protein, Nucleic Acid Enzyme, 54, 13, 1760-1766 (2009).
Mitsumdomi, "noshinkeigekai ni hitsuyona haigan no chishiki (knowledge of lung cancer required for neurosurgeons)," Currently Practical Neurosurgery, 21, 8, 895-901 (2011).
Narita, "Chemotherapy for brain metastases," Japanese Journal of Clinical Medicine, 268, 10, 593-597 (2010).
Notification of First Office Action for Chinese Patent Application No. 201580063121.3, dated Sep. 4, 2019 [English translation], 15 pages.
Official Action for Japanese Patent Application No. 2017-515756 dated Oct. 16, 2019 [English translation], 14 pages.
Ohori et al., "The Role of Chemotherapy in Brain Metastases," Japanese Journal of Neurosurgery, 16, 840-848 (2007).

* cited by examiner

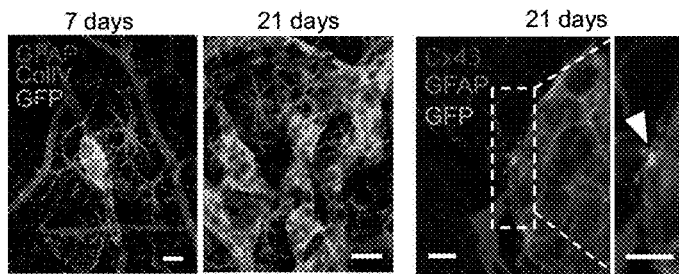
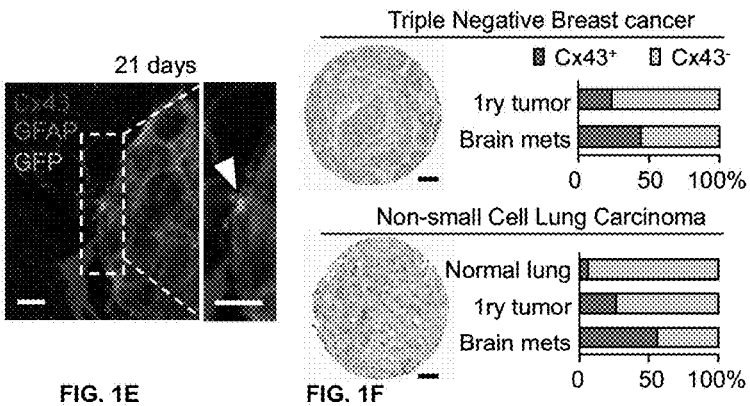
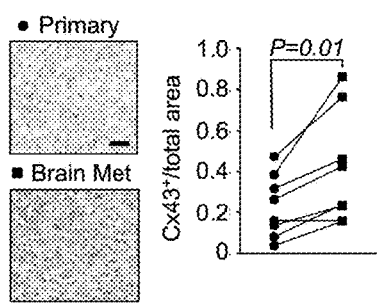
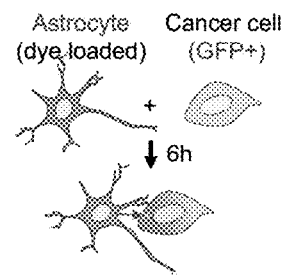
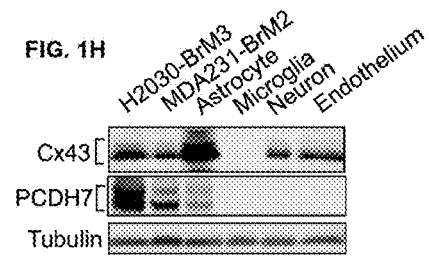
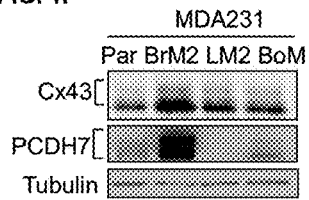
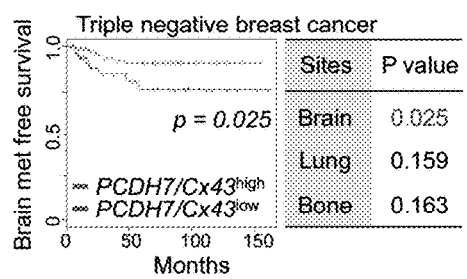
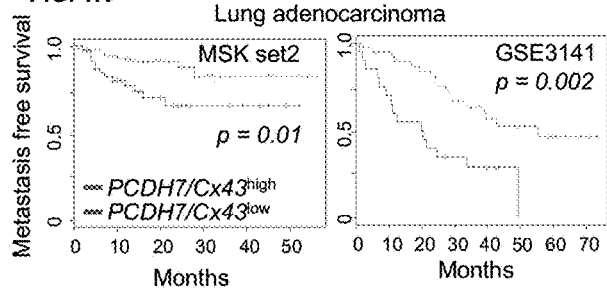

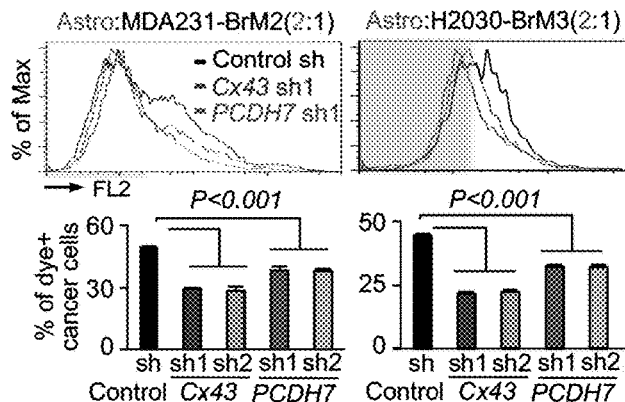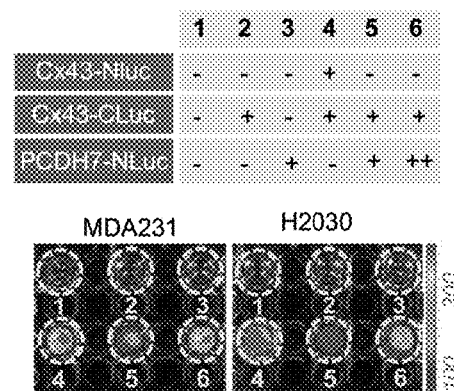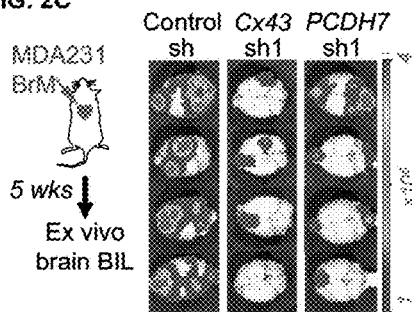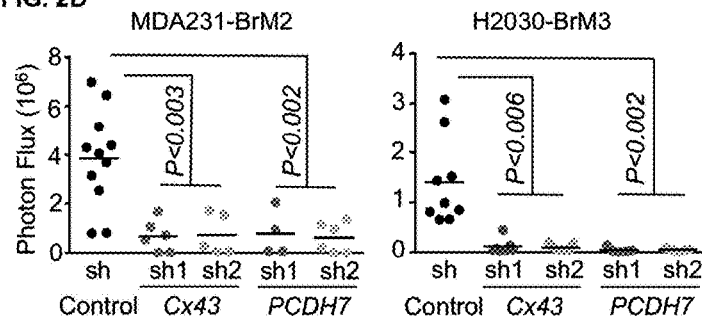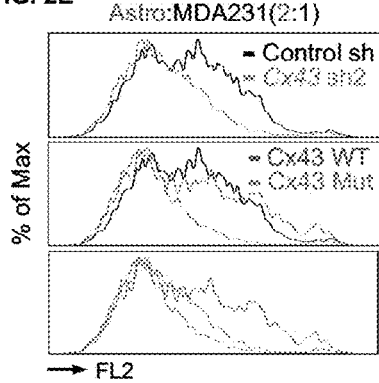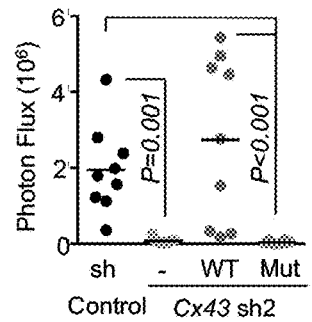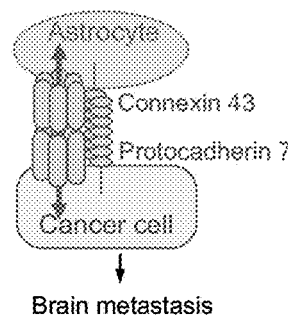

FIG. 3A
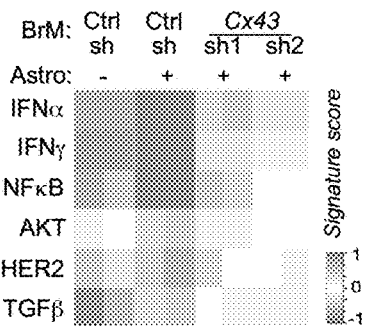
FIG. 3B
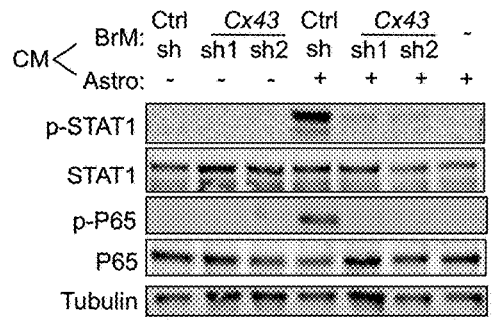
FIG. 3C
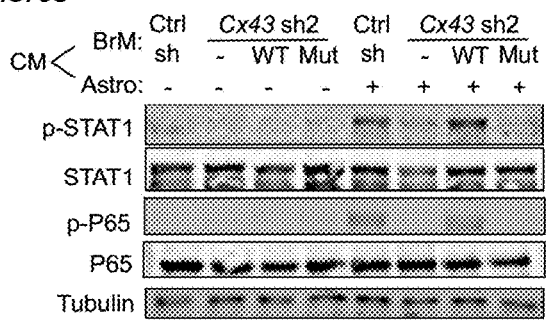
FIG. 3D
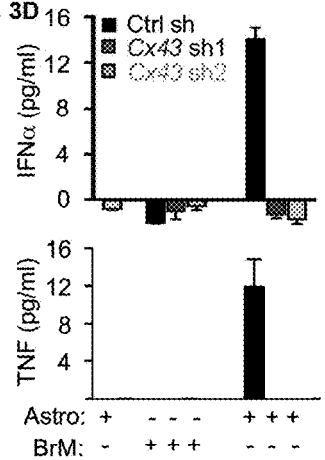
FIG. 3E
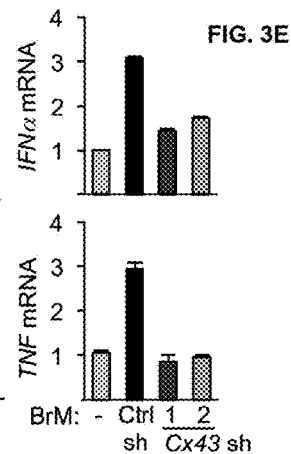
FIG. 3F
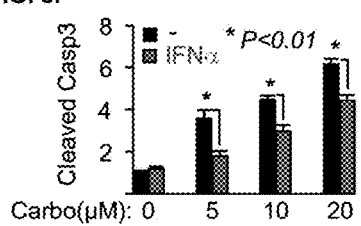
FIG. 3G
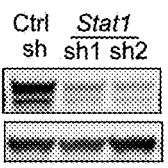
FIG. 3H
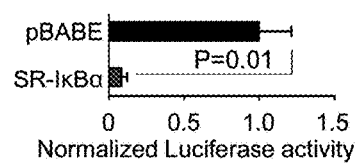
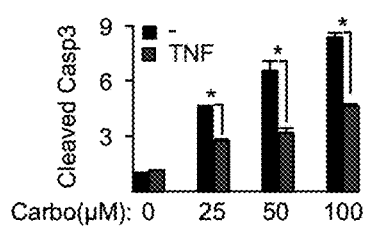
FIG. 3I
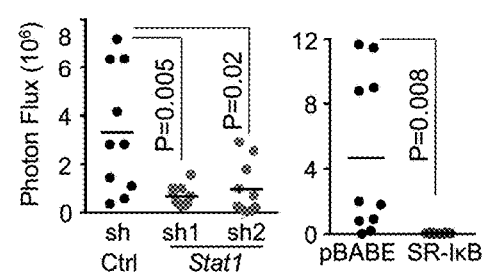

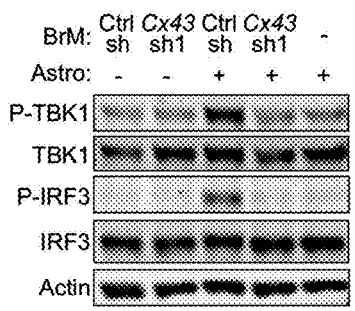
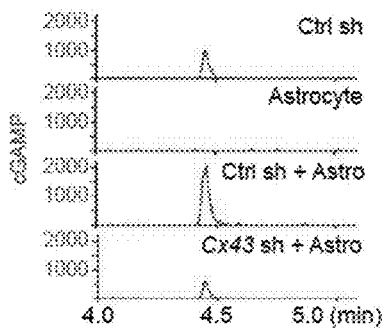
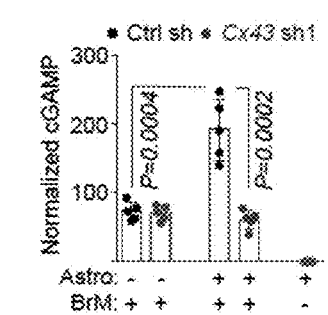
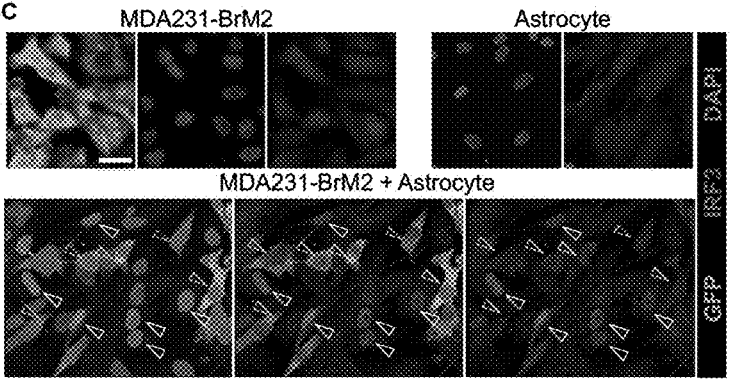
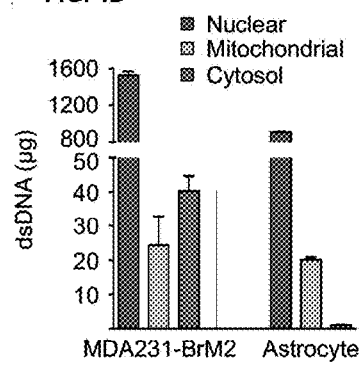
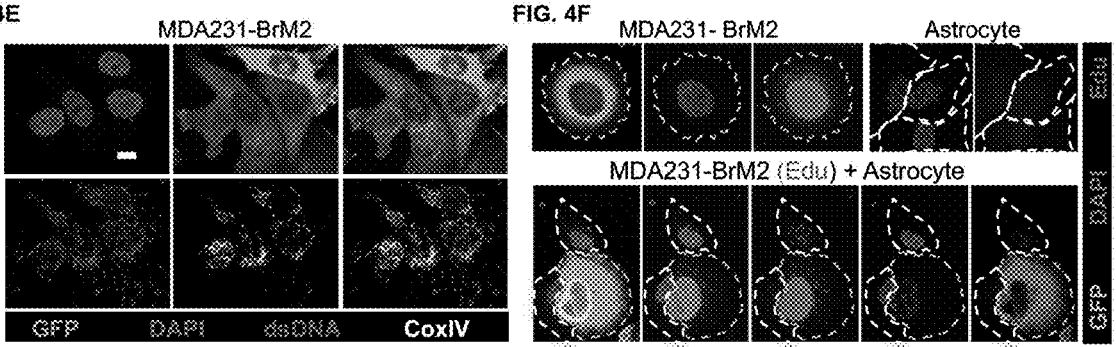
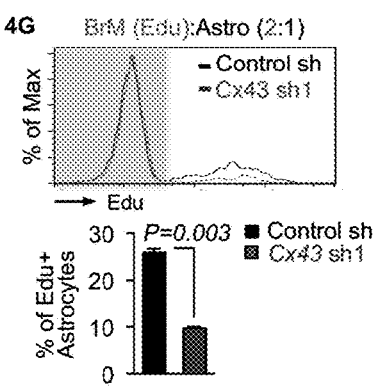
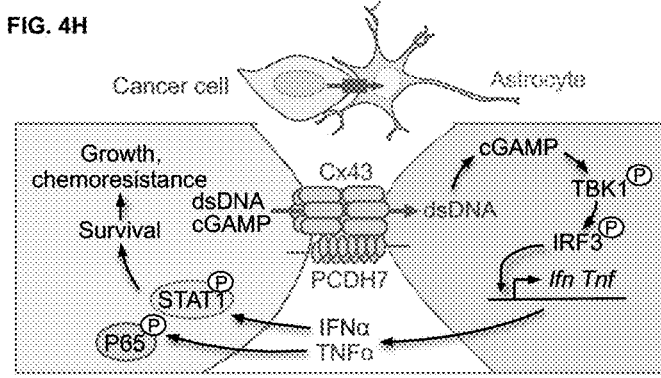

FIG. 6A
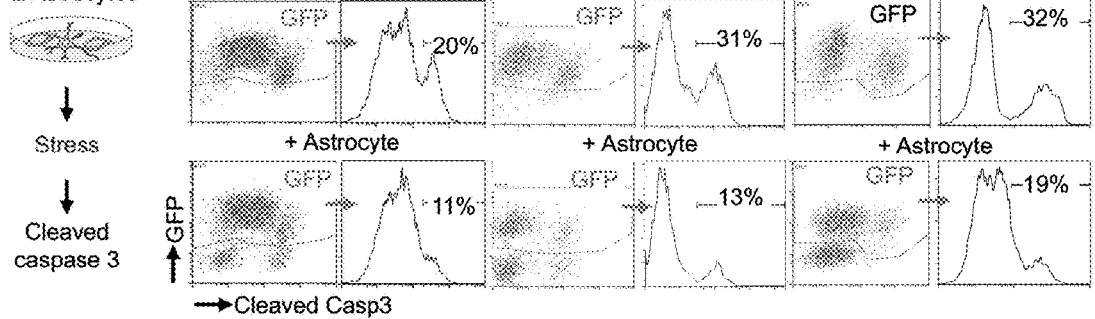
FIG. 6B Cancer cells ± Astrocytes
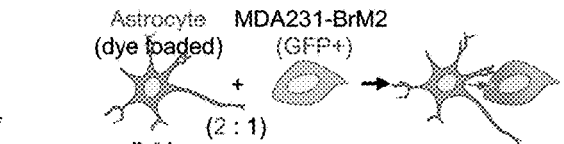
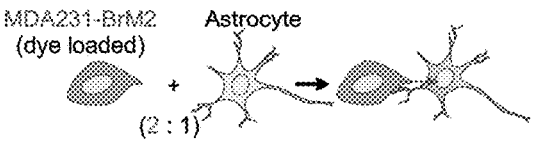
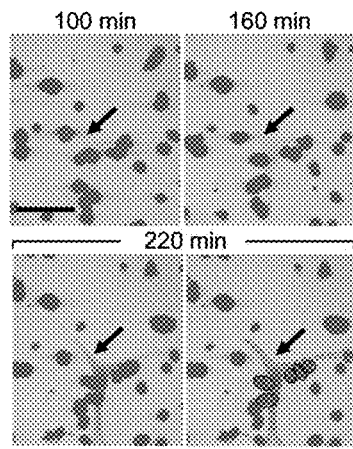
FIG. 6C
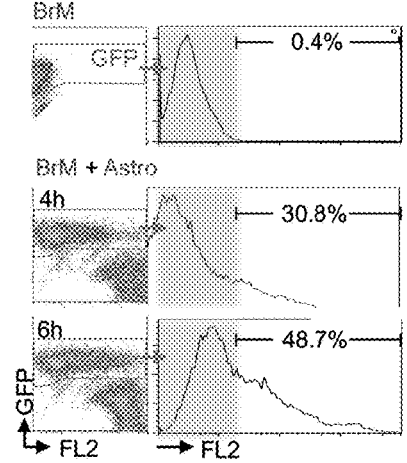
FIG. 6D

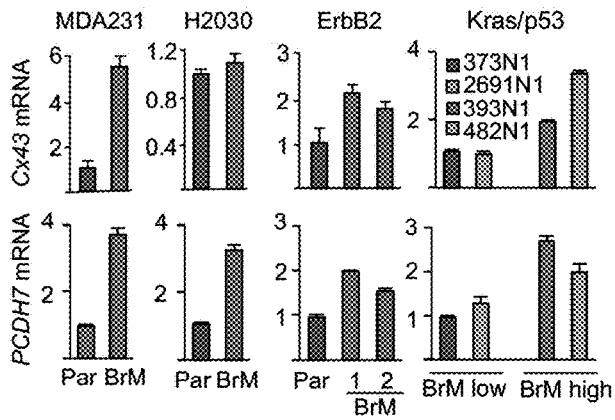
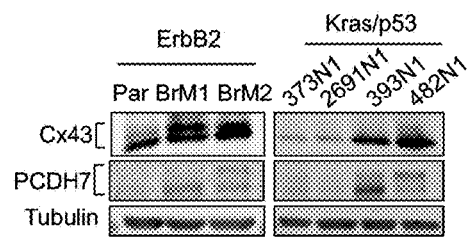
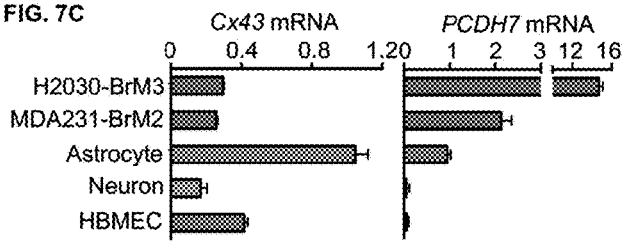
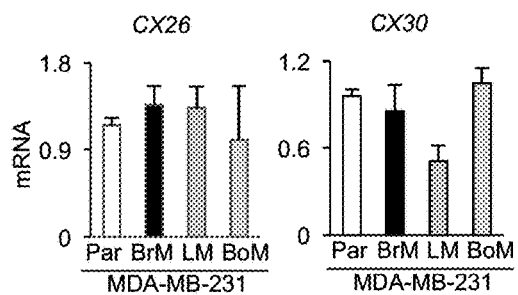
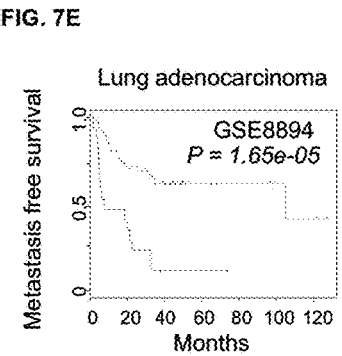
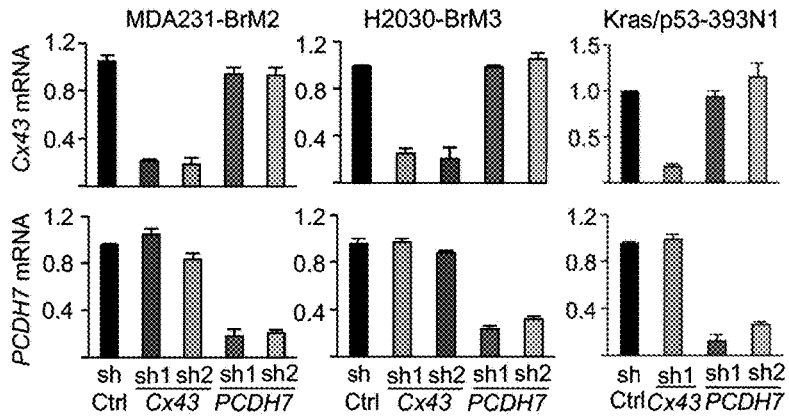

FIG. 13A
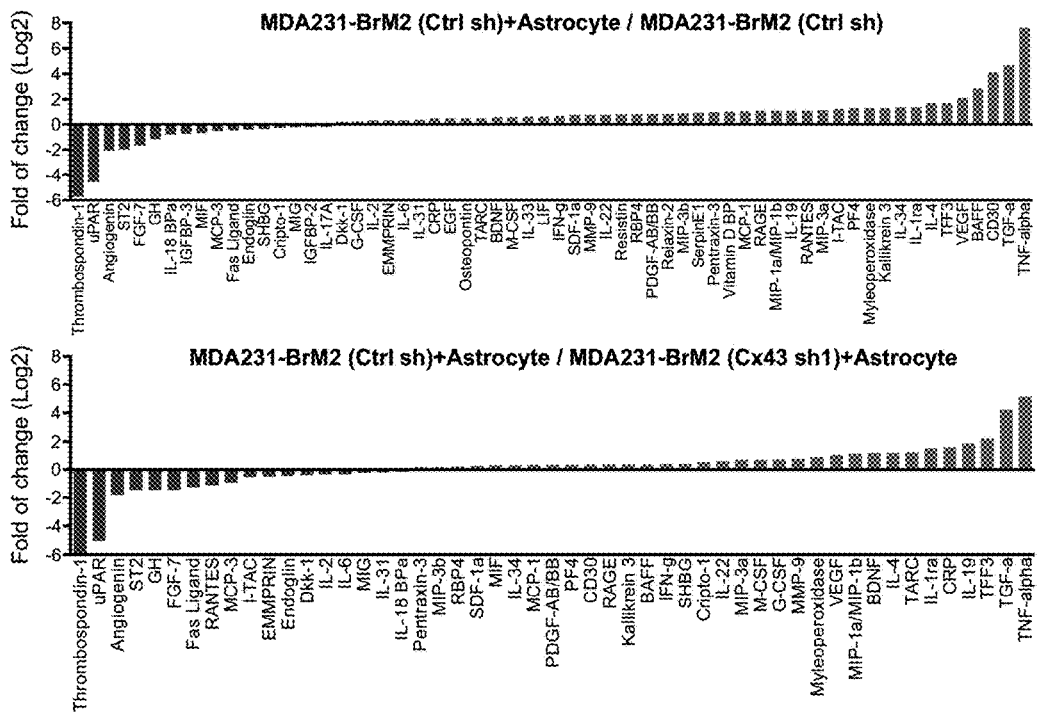
FIG. 13B
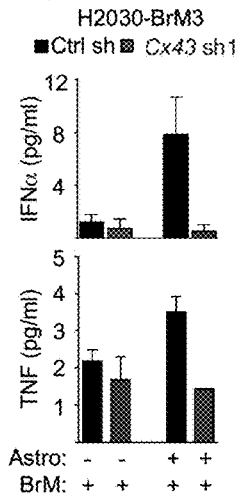
FIG. 13C
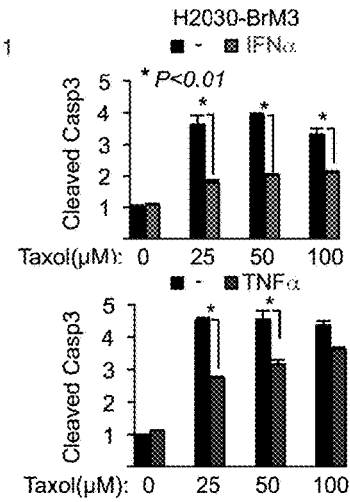
FIG. 13D
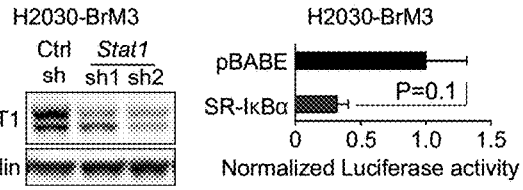
FIG. 13E
FIG. 13F
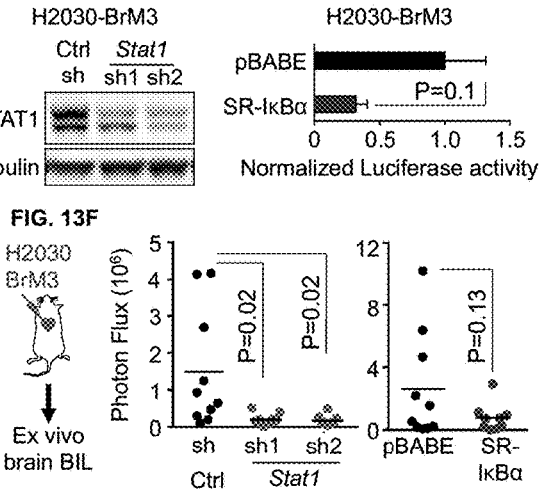

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcccaaactg atggtgtcaa t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcgacagaaa caattcttct t                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaggagaca acatttcaat                                                20
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctggcatta tgacggtgat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctggaagatt tacaagatga a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccctgaagta tctgtatcca a                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taaggacaat cctctgtct                                                 19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgagtggaat cttgatgct                                                 19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gaatcaacac tgccatccg                                                 19

```
<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttaagatgat tagaatcac                                                      19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgagtaccac ctccaccgg                                                      19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
taactttaaa ctcatacct                                                      19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taaacttagg gtcgttgtc                                                      19

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccgggcgcga tagcgctaat aatttctc                                            28

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agttcaacgt ggtcatcgtg                                                     20
```

```
<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acaatcaggg agttgttgct c                                               21
```

METHODS FOR TREATING BRAIN METASTASIS

PRIORITY CLAIM

This application is a continuation of U.S. patent application Ser. No. 15/462,253, filed Mar. 17, 2017, which is a continuation of International Patent Application No. PCT/US2015/051057, filed Sep. 18, 2015, which claims priority to U.S. Provisional Application No. 62/052,966, filed Sep. 19, 2014, to each of which priority is claimed and the contents of which are hereby incorporated by reference in their entireties.

GRANT INFORMATION

This invention was made with government support under CA129243, CA163167 and CA008748 awarded by the National Institutes of Health and W81XWH-12-0074 awarded by the Department of Defense (DoD). The government has certain rights in the invention.

SEQUENCE LISTING

The specification further incorporates by reference the Sequence Listing submitted via EFS on Sep. 13, 2019. Pursuant to 37 C.F.R. § 1.52(e)(5), the Sequence Listing text file, identified as 072734_0933SEQLIST.txt, is 4,064 bytes in size and was created on Sep. 13, 2019. The Sequence Listing, electronically filed on Sep. 13, 2019, does not extend beyond the scope of the specification and thus does not contain new matter.

1. INTRODUCTION

This present invention relates to gap junction inhibitors for use in treating brain metastasis. As such, these inhibitors may be used in methods of treating cancer patients.

2. BACKGROUND OF THE INVENTION

Brain metastases occur in 20-40% of advanced stage cancers and represent the most prevalent intracranial malignancy in adults (Gavrilovic and Posner, 2005; Maher et al., 2009). Lung and breast cancers are the most common sources. Despite treatment advances at other metastatic sites, current clinical management of brain metastases affords limited disease control and most patients succumb to tumor progression less than twelve months after diagnosis (Gavrilovic and Posner, 2005; Stelzer, 2013). The mechanisms underlying this disease process must therefore be understood so that they may be parlayed into rational therapeutic strategies.

The brain's unique microenvironment poses a formidable barrier to metastatic cancer cells. Recent progress has begun to unravel the complex cellular and molecular interactions responsible for the initiation of brain metastases. Circulating cancer cells that mechanically lodge in brain capillaries must first traverse the reinforced vessel walls that constitute the blood-brain barrier (BBB) (Eichler et al., 2011). Genes have been identified that mediate cancer cell extravasation through the BBB in experimental models and predict brain metastasis in the clinic (Bos et al., 2009; Li et al., 2013). Once inside the brain parenchyma, metastatic cells remain associated with the microvasculature (Kienast et al., 2010; Lorger and Felding-Habermann, 2010). Expression of the cell adhesion molecule LCAM in the cancer cells mediates their tight adhesion to the abluminal capillary basal lamina as a requirement for the initiation of metastatic outgrowth (Valiente et al., 2014). Wnt is one of the signaling pathways supporting the outgrowth (Nguyen et al., 2009). However, the vast majority of cancer cells that infiltrate the brain perish (Chambers et al., 2002; Heyn et al., 2006; Kienast et al., 2010), and they are rejected by the most abundant cell type in the brain, the astrocyte (Valiente et al., 2014).

Functionally pleiotropic, astrocytes maintain the BBB, orchestrate neurovascular coupling, sustain homeostasis of a tissue under stringent metabolic demands (Oberheim et al., 2012) and react acutely against disturbances like injury or infiltrating cells (Pekny and Nilsson, 2005). Reactive astrocytes generate plasmin, which mobilizes the pro-apoptotic cytokine FasL to kill infiltrating cancer cells (Valiente et al., 2014). Plasmin additionally cleaves cell surface LCAM in the cancer cells to suppress their ability to coopt the vasculature (Valiente et al., 2014). To evade astrocyte attack, brain metastatic cells from breast cancer and lung cancer express serpin inhibitors of plasminogen activator (PA) (Valiente et al., 2014). Although these observations indicate that astrocytes guard the brain against metastatic invasion, there is also evidence that the role of astrocytes in metastasis may not be uniformly antagonistic. In vitro, astrocyte co-culture protects melanoma cell lines from chemotherapeutic drugs (Kim et al., 2011), and in vivo astrocytes can activate Notch signaling in cancer cells (Xing et al., 2013).

3. SUMMARY OF THE INVENTION

The present invention relates to methods for treating brain metastasis by inhibiting gap junction functionality. It is based, at least in part, on the discovery that cancer cells expressing Protocadherin 7 and Connexin 43 form gap junctions with astrocytes that promote the growth of brain metastases, and that inhibition of Protocadherin 7 and/or Connexin 43 expression in cancer cells reduces progression of brain metastases. It is further based on the discovery that treatment with gap junction inhibitors tonabersat and meclofenamate inhibited progression of brain metastatic lesions and enhanced the anti-cancer activity of the conventional chemotherapeutic agent, carboplatin.

Certain non-limiting embodiments provide for a method for treating a subject having a cancer comprising administering, to the subject, an amount of a gap junction inhibitor that inhibits metastatic progression of the cancer in the brain. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for a method for inhibiting growth and/or survival of metastatic cancer cells in the brain of a subject, comprising treating the subject with a therapeutically effective amount of a gap junction inhibitor. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for a method for treating brain metastasis in a subject having a cancer, comprising administering, to the subject, a therapeutically effective amount of a gap junction inhibitor. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for, in a subject having a cancer, a method of preventing metastasis of the cancer to the brain, comprising administering, to the subject, a therapeutically effective amount of a gap junction inhibitor. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for in a subject having a cancer, a method of reducing the risk of detectable metastasis of the cancer to the brain, comprising administering, to the subject, a therapeutically effective amount of a gap junction inhibitor. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent that can attain therapeutic levels in the brain, such as, but not limited to, carboplatin. When the method of the invention is applied, the subject may be known to have one or more brain metastases, or alternatively, was not known to have a brain metastasis prior to treatment.

Certain non-limiting embodiments provide for, in a subject having a cancer, a method of reducing the risk of detectable metastasis of the cancer to the brain, comprising administering, to the subject, a therapeutically effective amount of a Protocadherin 7 inhibitor. In particular non-limiting examples, the Protocadherin 7 inhibitor is an interfering RNA. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for a method for lengthening the period of survival of a subject having a cancer, comprising administering to the subject an effective amount of a gap junction inhibitor, for example, wherein administering the gap junction inhibitor inhibits metastatic progression of the cancer in the brain. In particular non-limiting examples, the gap junction inhibitor is a Connexin 43 inhibitor or a Protocadherin 7 inhibitor, or a combination thereof. In particular non-limiting examples, the inhibitor is tonabersat or meclofenamate or a combination thereof. In particular non-limiting examples, the cancer is breast cancer or lung cancer, and/or the cancer cells of the subject express Connexin 43 and/or Protocadherin 7. In particular non-limiting examples, the method further comprises administering, to the subject, a therapeutically effective amount of an anti-cancer agent such as, but not limited to, carboplatin. When the method of the invention is applied, the subject may be known to have one or more brain metastases, or alternatively, was not known to have a brain metastasis prior to treatment.

Certain non-limiting embodiments provide for an assay for evaluating gap junction activity, for example assessing inhibition, by measuring levels of cGAMP, where a decrease in cGAMP correlates with gap junction inhibition. Particular non-limiting embodiments provide for a method for inhibiting growth and/or survival of metastatic cancer cells in the brain of a subject, comprising treating the subject with a therapeutically effective amount of a gap junction inhibitor that produces a decrease in cGAMP relative to the level of cGAMP in the absence of that amount of gap junction inhibitor. Further non-limiting embodiments provide for a method of determining whether a brain tumor or metastatic brain tumor in a subject will receive therapeutic benefit from treatment with a gap junction inhibitor, comprising determining whether, in a sample from said tumor, exposure to a gap junction inhibitor leads to a decrease in cGAMP, where a decrease in cGAMP is indicative of therapeutic benefit.

4. BRIEF DESCRIPTION OF FIGURES

FIGS. 1A-1K provide Cx43 and PCDH7 association with brain metastasis. (FIG. 1A) GFP+H2030-BrM3 cells (green) are surrounded by GFAP+ activated astrocytes (red) in the brain parenchyma at early (day 7) and later (day 21) time points following intracardiac inoculation in mice. Blue, collagen IV (ColIV) staining in vessels. Scale bar, 10 µm. (FIG. 1B) Cx43 staining (arrowhead) at the interface of GFP+H2030-BrM3 (green) and GFAP+ astrocytes (blue). Scale bar, 10 µm. (FIG. 1C) Representative images of Cx43 staining in human brain metastasis samples from triple-negative breast cancer and non-small cell lung carcinoma.

The proportion of CX43-positive samples was quantified in primary (1ry) tumours, brain metastases, and normal lung tissues. Scale bar, 100 µm. (FIG. 1D) Representative images and quantification of Cx43 immunostaining in matched primary and brain metastatic samples from non-small lung carcinoma patients. Scale bar, 100 µm. (FIG. 1E) Schematic illustration of dye transfer assay. (FIG. 1F) Quantification of dye transfer from astrocytes to cancer cells. Histograms show red fluorescent signal in parental (Par) and BrM cells. All values are mean±S.E.M. (n=3 biological replicates). n=3 independent experiments. (FIG. 1G-1I) Cx43 and PCDH7 western immunoblotting in the indicated parental and brain metastatic derivatives ((FIG. 1G) n=3 independent experiments), in brain metastatic cells compared to brain cell types ((FIG. 1H) n=2 independent experiments), and in MDA231 derivatives metastatic to brain, lung (LM) or bone (BoM) ((FIG. 1I) n=2 independent experiments). (FIGS. 1J-1K) Kaplan-Meier plot of cumulative brain metastasis-free survival in 189 cases of triple-negative breast cancer (FIG. 1J) and 129 cases (MSKCC set2) and 58 cases (GSE3141) of lung adenocarcinoma (FIG. 1K), based on Cx43/PCDH7 expression in the primary tumour.

FIGS. 2A-2G provide Cx43/PCDH7 carcinoma-astrocyte gap junctions mediate brain metastasis. (FIG. 2A) Histograms (top) and quantification (bottom) of dye transfer from astrocytes to control and Cx43-depleted or PCDH7-depleted brain metastatic cells. Values are mean±S.E.M. (n=3 biological replicates). n=3 independent experiments. (FIG. 2B) Luciferase complementation assay to detect Cx43-PCDH7 interactions. NLuc and CLuc, N-terminal and C-terminal firefly luciferase halves. The table (top) numerically identifies the cell line combinations used in the assays (bottom), and bioluminescence imaging (BLI) of a representative plate. BLI (FIG. 2C) and quantification (FIG. 2D) of brain metastatic lesions formed by control, Cx43-depleted, or PCDH7-depleted brain metastatic cells. n=3 independent experiments. (FIGS. 2E, 2F) Wild type (WT) or T154A mutant (Mut) Cx43 was re-expressed in Cx43-depleted MDA231-BrM2 cells (Cx43 sh2). The cells were subjected to astrocyte dye transfer analysis ((FIG. 2E) n=3 independent experiments), or to brain metastasis assays and BLI quantification ((FIG. 2F) n=2 independent experiments). (FIG. 2G) Schematic summary of Cx43- and PCDH7-mediated interactions between cancer cells and astrocytes in brain metastasis.

FIGS. 3A-3I provide gap junctions activate STAT1 and NF-κB pathways in cancer cells. (FIG. 3A) Signaling pathway analysis of TRAP-Seq data from MDA231-BrM2 cells after co-culture with astrocytes. Control (Ctrl) or Cx43-depleted MDA231-BrM2 cells expressing an L10a-GFP ribosomal protein fusion were co-cultured with astrocytes for 24 h prior to polysome immunoprecipitation and mRNA sequencing. Heatmap depicts blue (down-regulated) and red (up-regulated) pathways. n=2 biological replicates. (FIGS. 3B, 3C) STAT1 and NF-κB p65 phosphorylation in MDA231-BrM2 cells after a 2 h incubation with conditioned media (CM) from astrocyte co-culture. CM were collected after 24 h co-culture of astrocytes with control or Cx43-depleted MDA231-BrM2 cells (FIG. 3B), or from Cx43-depleted MDA231-BrM2 cells that were transduced with wild type Cx43 (WT) or Cx43(T154A) mutant (Mut) (FIG. 3C). n>3 independent experiments. (FIG. 3D) ELISA of IFNα and TNFα in CM from astrocyte co-cultures with the indicated MDA231-BrM2 cells. All values are mean±S.E.M. (n=4 technical replicates). n>2 independent experiments. (FIG. 3E) Relative mRNA levels of IFNA and TNFA in astrocytes re-isolated after co-culture with MDA231-BrM2 cancer cells. All values are mean±S.E.M. (n=3 biological replicates). n=2 independent experiments. (FIG. 3F) Relative levels of cleaved caspase 3 in MDA231-BrM2 cells treated with various concentrations of carboplatin (Carbo) in the presence or absence of 10 units/ml (39 units/ng) IFNαA or 10 µg/ml TNFα. All values are mean±S.E.M. (n=5 technical replicates). n=3 independent experiments. (FIG. 3G) STAT1 levels in control and STAT1-knockdown MDA231-BrM2 cells. (FIG. 3H) NF-κB renilla luciferase reporter assay in MDA231-BrM cells expressing control pBABE or SR-IκBα vector. All values are mean±S.E.M. (n=3 technical replicates). (FIG. 3I) Quantification of BLI signal from brain metastases formed by control, STAT1-knockdown, and SR-IκBα MDA231-BrM2 cells. n=2 independent experiments.

FIGS. 4A-4H provide gap junctions mediate a cytosolic dsDNA response in astrocytes. (FIG. 4A) MDA231-BrM2 cells expressing control shRNA (Ctrl sh) or shRNA targeting Cx43, were cultured for 18 h with or without astrocytes, and subjected to immunoblotting analysis of phosphorylated TBK1 and IRF3 (n=3 independent experiments). (FIG. 4B) MDA231-BrM2 alone, astrocytes alone, or 18 h co-cultures, were harvested for sample preparation and cGAMP analysis by LC-MS/MS. Histogram (right) corresponds to normalized cGAMP peaks in (left), and is representative of 5 biological replicates. n=3 independent experiments. See also FIG. 16. (FIG. 4C) Representative images of dual immunofluorescent staining of IRF3 and GFP. DAPI, nuclear staining. In co-cultures: white arrows, nuclear accumulation of IRF3 in astrocytes; green arrows, even distribution of IRF3 in GFP+ MDA231-BrM2 cells. Scale bar, 20 µm. n=2 independent experiments. (FIG. 4D) Quantification of dsDNA in the indicated cellular fractions from $2\times10^7$ cells. Values are mean±S.E.M. (n=3 biological replicates). n=2 independent experiments. (FIG. 4E) Representative image of immunofluorescence staining of dsDNA, GFP, and Cox IV (mitochondrial marker) in MDA231-BrM2 cells. DAPI, nuclear staining. Scale bar, 10 µm. n=2 independent experiments. (FIGS. 4F, 4G) EdU labeled MDA231-BrM2 cells were co-cultured with astrocytes for 6 h. Transfer of EdU-labeled DNA from cancer cells to astrocytes was visualized using confocal microscopy (FIG. 4F), or quantified by flow cytometry (FIG. 4G). Cancer cells and astrocytes are delineated by green and white dotted lines, respectively. Scale bar, 10 µm. Values are mean±S.E.M. (n=3 biological replicates, n=2 independent experiments). (FIG. 4H) Schematic summary of gap junction mediated anti-dsDNA response, production of IFNα and TNFα in astrocytes, and consequent activation of STAT1 and NF-κB pathways in cancer cells to support brain metastasis.

Figure 5C:
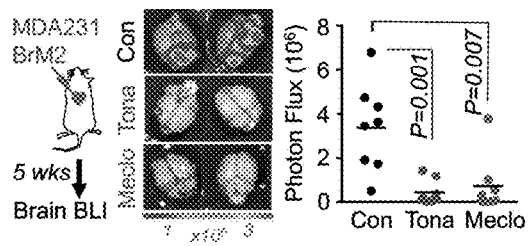
Figure 5D:
Figure 5E:
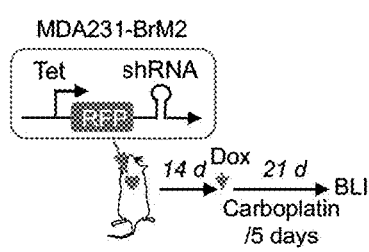
Figure 5F:
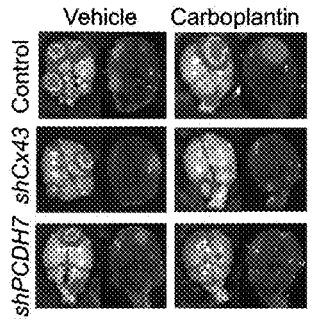
Figure 5G:
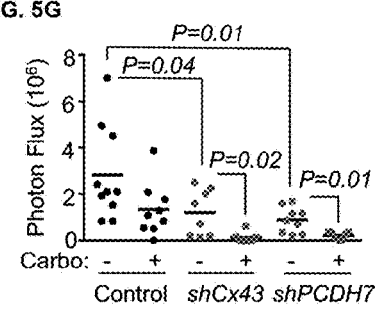
Figure 5H:
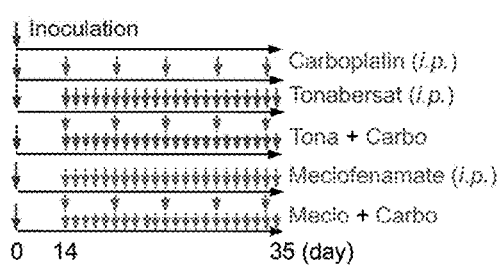
Figure 5I:
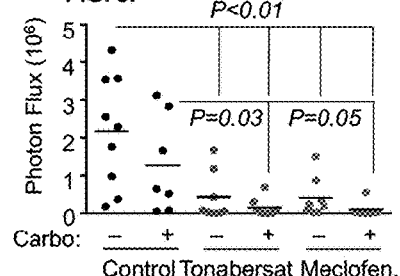

FIGS. 5A-5I provide inhibition of gap junction activity controls brain metastatic outgrowth. (FIG. 5A) Dye transfer from astrocytes to MDA231-BrM2 cells in the presence of the indicated concentrations of Tonabersat or meclofenamate. n≥3 independent experiments. (FIG. 5B) ELISA of IFNα and TNFα in conditioned media from co-cultured MDA231-BrM2 cell and astrocytes in the presence of Tonabersat (Tona) or meclofenamate (Meclo) with indicated concentrations. All graphs shown are mean±S.E.M. (n=4 technical replicates). n=2 independent experiments. (FIG. 5C) Tonabersat or meclofenamate was administered daily starting one day after cancer cell inoculation in mice. Brain metastatic lesions were quantified based on BLI. n=2 independent experiments. (FIG. 5D) GFP staining of 14-day brain metastatic lesions. Representative images show large, progressive lesions. DAPI, nuclear staining. Scale Bar, 40 µm. n=10 experimental mice. (FIG. 5E) 14 days after inoculation with MDA231-BrM2 cells transduced with inducible control, CX43 or PCDH7 shRNAs, mice were treated with doxycycline and carboplatin, as illustrated in the scheme. Brain metastatic lesions were quantified based on BLI. (FIGS. 5F, 5G) Representative images of matched ex vivo brain BLI and red fluorescence imaging. n=2 independent experiments. (FIG. 5H) 14 days after inoculation with MDA231-BrM2 cells, mice were treated with Tonabersat, meclofenamate, and carboplatin. Following the indicated regimens, brain metastatic lesions were quantified based on BLI. n=2 independent experiments (FIG. 5I).

FIGS. 6A-6D provide cancer cell-astrocyte interactions. (FIG. 6A) Cancer cells used in this study. (FIG. 6B) Astrocyte co-culture protects cancer cells. As illustrated in schema (left), cleaved caspase 3+/GFP+ apoptotic BrM cells were quantified after sFasL- or chemo-treatments. n=3 independent experiments. (FIGS. 6C, 6D) Gap junction communications between astrocytes and BrM cells. Time-lapse images of dye transfer from MDA231-BrM2 cells to astrocytes (FIG. 6C). Scale bars, 100 µm. Quantification of dye transfer from astrocytes to MDA231-BrM2 cells by flow cytometry over time (FIG. 6D). n=3 independent experiments.

FIGS. 7A-7G provide elevated expression of Cx43 and PCDH7 in brain metastatic cancer cells and astrocytes. (FIG. 7A) Cx43 and PCDH7 mRNA in parental (Par) and BrM cells. Values are mean±S.E.M. (n=3 technical replicates). n=3 independent experiments. (FIG. 7B) Cx43 and PCDH7 western blotting in ErbB2 parental and brain cells, as well as Kras/p53 cell lines. n=3 independent experiments. (FIG. 7C) Cx43 and PCDH7 mRNA in BrM cells compared to brain cells. n=3 independent experiments. (FIG. 7D) Cx26 and Cx30 mRNA in MDA231 parental (Par) and the metastatic derivatives of brain (BrM2), lung (LM) and bone (BoM). (FIG. 7E) Kaplan-Meier plot illustrates the probability of cumulative metastasis free survival in 63 cases (GSE8893) of lung adenocarcinoma based on Cx43/PCDH7 expression in the primary tumour. (FIGS. 7F, 7G) Knockdown of Cx43 and PCDH7 with short hairpin RNAs (shRNA) as assessed by RT-PCR (FIG. 7F) and western blotting (FIG. 7G). Ctrl, control. Values are mean±S.E.M. (n=3 technical replicates). n=3 independent experiments.

Figure 8A:
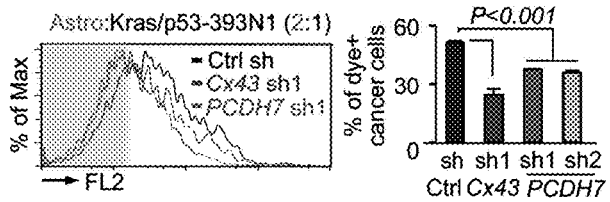
Figure 8B:
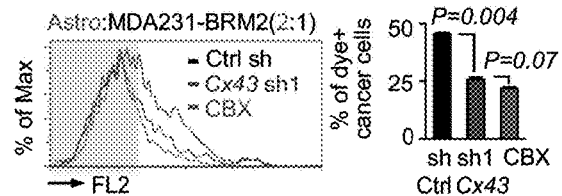
Figure 8C:
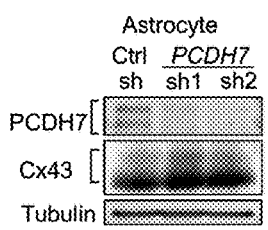
Figure 8D:
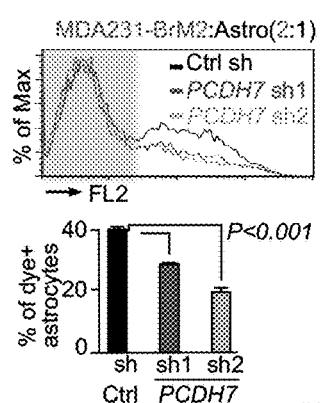

FIGS. 8A-8H provide PCDH7 facilitates gap junction communication. (FIGS. 8A, 8B) Histograms and quantification of dye transfer from astrocytes to control and Cx43-depleted or PCDH7-depleted Kras/p53-393N1 cells (FIG. 8A), and from astrocytes to control or Cx43-depleted MDA231-BrM2 cells, in comparison to Carbenoxolone (50 uM) treatment (FIG. 8B). (FIGS. 8C, 8D) PCDH7 in astrocytes facilitate gap junctions. PCDH7 western blotting in control or PCDH7-depleted astrocytes (FIG. 8C). Quantification of dye transfer from MDA231-BrM2 cells to PCDH7-depleted astrocytes (FIG. 8D). (FIG. 8E) Quantification of dye transfer from human brain microvascular endothelial cells (HBMEC) to control, Cx43- or PCDH7-depleted MDA231-BrM2 cells. (FIG. 8F) Dye transfer from MDA231-BrM2 cells to a mixed population of astrocytes and HBMEC. (FIG. 8G) Quantification of dye transfer from control or Cx43-depleted MDA231-BrM2 cells to human microglia. (FIG. 8H) As illustrated in schema, Cx43 mRNA in MDA231-BrM2 cells (left) or astrocytes (right) was detected after 24 h co-culture, separated by transwell, with microglia, astrocytes or cancer cells. For dye transfer assays, values are mean±S.E.M. (n=3 biological replicates). n≥2 independent experiments. In h, values are mean±S.E.M. (n=4 biological replicates).

FIGS. 9A-9E provide Cx43 directly interacts with PCDH7, but not with E cadherin or N cadherin. (FIG. 9A) Cx43 and PCDH7 western immunoblotting in cancer cells overexpressing fusion proteins. (FIG. 9B) Quantification of BLI after co-culture of Cx43-CLuc/PCDH7-NLuc(+) cancer cells and astrocytes for 15 min. c-e, Luciferase split assay to detect Cx43-E cadherin or Cx43-N cadherin interactions. NLuc and CLuc: N-terminal and C-terminal firefly luciferase halves. The table (FIG. 9C) numerically identified the cell line combinations used in the assays, western immunoblotting (FIG. 9D) indicated E or N cadherin expression in cancer cells overexpressing fusion proteins, and bioluminescence imaging (BLI) of a representative plate (FIG. 9E). n≥2 independent experiments.

FIGS. 10A-10E provide Inhibition of gap junction activity prevents brain metastatic outgrowth. (FIG. 10A) Bioluminescent imaging (BLI) quantification of brain metastatic lesions formed by control (Ctrl), Cx43- or PCDH7-depleted Kras/p53-393N1 cells. n=2 independent experiments. (FIG. 10B) Representative images of GFP+ brain metastatic lesions formed by control, Cx43- or PCDH7-depleted MDA231-BrM2 cells. Brain sections or brain metastatic lesions are delineated by dotted white line or dotted red line, respectively. Scale bar, 1000 µm. (FIG. 10C) BLI (images) and quantification (bar graph) of lung metastatic lesions formed by MDA231-BrM2 cells. Values are mean±S.E.M. (n=5 mice in each group). n=2 independent experiments. (FIGS. 10D, 10E) Gap junction-mediated brain metastasis requires channel function of Cx43. Wild type (WT) or T154A mutant (Mut) Cx43 was re-expressed in Cx43 depleted MDA231-BrM2 cells (CX43 sh2). Cx43 expression was detected by western blotting (FIG. 10D) and brain metastatsis formed by these cells was quantified by BLI (FIG. 10E). n=2 independent experiments.

FIGS. 11A-11D provide role of Cx43 and PCDH7 in brain metastasis. (FIG. 11A) Cx43 and PCDH7 do not mediate trans-BBB Migration. Quantification of control (Ctrl), Cx43- or PCDH7-depleted MDA231-BrM2 cells in 7-day brain lesions. Values are mean±S.E.M. (n=5 brains in each group). (FIG. 11B) Cx43 and PCDH7 mediate cancer cell colonization in 14-day brain lesions. Representative images are GFP (green) and Ki67 (red) staining. DAPI, nuclear staining. Scale bar, 20 µm. Bar graph is the proportion of Ki67+ cancer cells. Values are mean±S.E.M. (n=5 brains in each group). (FIG. 11C) Cx43 and PCDH7 mediate cancer cell survival. Brain slice assays. Representative images are GFP (green) and cleaved caspase 3 (Casp3)(red) staining. Scale bar, 30 µm. Histogram is the proportion of caspase 3+ apoptotic cancer cells. Values are mean±S.E.M. (n=5 brain slices in each group). Scale bars, 30 µm. (FIG. 11D) Cx43 and PCDH7 do not affect vascular cooption of cancer cells in 14-day brain lesions. Representative images are GFP (green) staining and vascular structure filled with TRITC dextran (red). Scale bar, 20 µm. n=2 independent experiments.

FIGS. 12A-12D provide translating ribosome affinity purification (TRAP) and cytokine array. (FIG. 12A) Schematic illustration of TRAP experimental set up to isolate translating mRNA from MDA231-BrM2 cells under 3 conditions (#1, #2, #3). (FIG. 12B) Principle component (PC) analysis of TRAP mRNA sequencing. (FIG. 12C) Scatter plot of log 2 fold-changes regulated by astrocytes and gap junction communications between BrM cells and astrocytes. (FIG. 12D) STAT1 and NF-κB p65 phosphorylation in H2030-BrM3 cells after a 2 h incubation with conditioned media (CM) from astrocyte co-cultures. CM were collected after 24 h co-culture of astrocytes with control or Cx43-depleted H2030-BrM3 cells. n=3 independent experiments.

FIGS. 13A-13F provide gap junction-generated signaling activates IFN and NF-Kb pathways in cancer cells. (FIG. 13A) Cytokine array analysis of the conditioned media collected after 24 h co-culture of astrocytes with control or Cx43-depleted MDA231-BrM2 cells. Log 2 fold-changes were plotted. (FIG. 13B) ELISA of IFNα and TNFα in CM from astrocyte co-cultures with the indicated H2030-BrM3 cells. All values shown are mean±S.E.M. (n=4 technical replicates). n=2 independent experiments. (FIG. 13C) Relative levels of cleaved caspase 3 in H2030-BrM3 cells treated with various concentrations of Taxol in the presence or absence of 10 units/ml (39 units/ng) recombinant IFNαA or 10 μg/ml recombinant TNFα. All values are mean±S.E.M. (n=5 technical replicates). n=3 independent experiments. (FIGS. 13D, 13E) STAT1 levels in control and STAT1-knockdown H2030-BrM3 cells. (FIG. 13F) Quantification of BLI signal from brain metastases formed by control, STAT1-knockdown cells. n=2 independent experiments.

FIGS. 14A-14G provide gap junctions initiate cytosolic DNA response in astrocytes. (FIG. 14A) Control or Cx43-deplated H2030-BrM3 cells were co-cultured for 18 h with or without astrocytes, and subjected to immunoblotting analysis of phosphorylated TBK1 and IRF3 (n=3 independent experiments). (FIG. 14B) cGAMP identification. The peak at 4.47 min contains all 3 SRM transitions specific for cGAMP. RT: retention time, AA: automatically integrated peak area. (FIG. 14C) Quantification of dsDNA in the indicated cellular fractions from $2 \times 10^7$ H2030-BrM3 cells. Values are mean±S.E.M. (n=3 biological replicates). n=2 independent experiments. (FIG. 14D) Ratio of cytosol dsDNA and nuclear dsDNA in indicated cancer cells and non-neoplastic cells. (FIG. 14E) Representative image of immunofluorescent staining of dsDNA, GFP, Cox IV (mitochondria marker) in H2030-BrM3 cells. DAPI, nuclear staining. Scale bar, 10 μm. (FIG. 14F) Representative image of immunofluorescent staining of dsDNA, Cox IV (mitochondria marker) in astrocytes. DAPI, nuclear staining. Phalloidin, cytoskeletal staining. Scale bar, 10 μm. (FIG. 14G) EdU labeled H2030-BrM3 cells were co-cultured with astrocytes for 6 h. Transfer of EdU-labeled DNA from cancer cells to astrocytes was visualized using con-focal microscopes. Cancer cells or astrocytes were delineated by green or white dotted lines, respectively. Scale bar, 10 μm. n=2 independent experiments.

FIGS. 15A-15G provide inhibition of gap junction activity prevents brain metastatic outgrowth. (FIGS. 15A-15D) Following treatment with Tonabersat (Tona) or meclofenamate (Meclo) (FIG. 15A), brain metastasis (FIG. 15B), primary tumour growth in mammary fat pads (FIG. 15C), or lung metastasis (FIG. 15D) were quantified by BLI. Values are mean±S.E.M. (n=5 mice in each group). n=2 independent experiments. (FIGS. 15E, 15F) Knockdown of Cx43 and PCDH7 in MDA231-BrM2 cells with tet-on inducible short hairpin RNAs (shRNA), as assessed by RT-PCR (FIG. 15E) and Western immunoblotting (FIG. 15F), after doxycycline treatment in vitro. n=2 independent experiments. (FIG. 15G) Brain ex vivo Bioluminescent imaging (BLI) 14 days after inoculation of MDA231-BrM2 cells.

Figure 16:
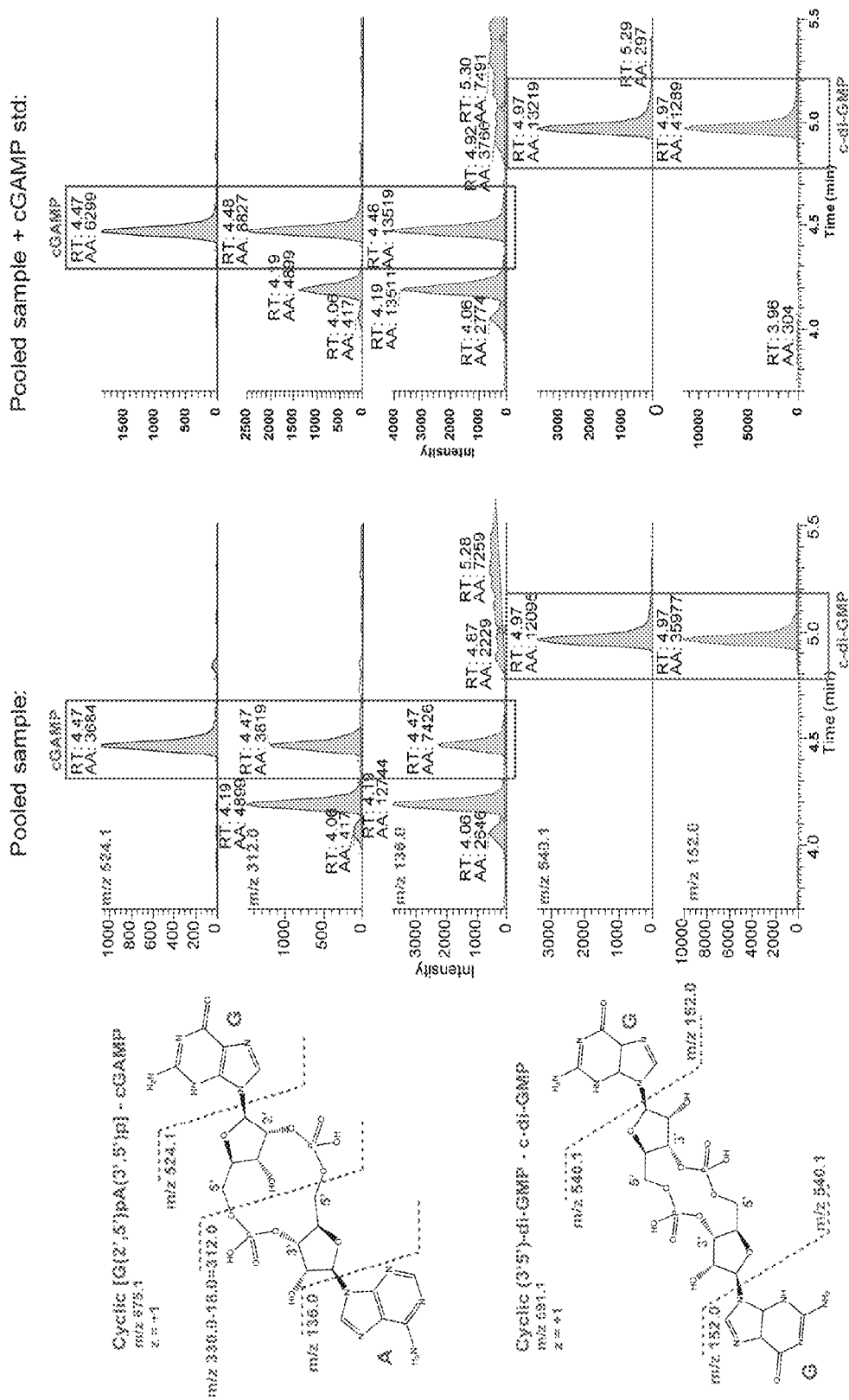

FIG. 16 provides confirmation of cGAMP identification. A pooled sample from all experimental conditions shown in FIG. 4b analyzed by LC-MS/MS. Only the peak at 4.47 min contains all 3 SRM transitions specific for cGAMP. The peak at 4.47 min is increased by the addition of 5 μL of 40 nM cyclic [G(2',5')pA(3',5')p] (cGAMP) to the pooled sample. As internal and negative control, c-di-GMP contains all 2 SRM transitions at 4.97 min peak and the peak does not change by adding standard cGAMP. dRT: retention time, AA: automatically integrated peak area.

5. DETAILED DESCRIPTION

For clarity and not by way of limitation the detailed description of the invention is divided into the following subsections:

(i) Gap junction inhibitors;
(a) Connexin 43 inhibitors; and
(b) Protocadherin 7 inhibitors;
(c) Assay for gap junction activity/inhibition;
(ii) cancer targets;
(iii) pharmaceutical formulations; and
(iv) methods of treatment.

5.1 Gap Junction Inhibitors

The present invention provides inhibitors of gap junctions (e.g., gap junction antagonists) for use in the disclosed methods. In certain embodiments, gap junction inhibitors can include compounds, small molecules, chemicals, polypeptides, nucleic acids and proteins that inhibit and/or reduce the expression and/or activity of gap junction components or inhibit and/or reduce the formation, patency, signaling and/or activity of gap junctions.

In certain non-limiting embodiments, gap junction inhibitors that are small molecules include carbenoxolone, glycyrrhetinic acid, quinine, quinidine, mefloquine, heptanol, octanol, anandamide, fenamates, 2-aminoethoxy-diphenylborate (2-APB), retinoic acid, oleamide, spermine, aminosulfonates, sodium propionate, tonabersat and meclofenamate (meclofenamic acid). Additional non-limiting examples of gap junction inhibitors are disclosed in U.S. Pat. Nos. 5,843,989; 6,211,211; 7,632,866, 6,251,931; 7,704,946; and PCT Patent Application No. WO 1999/026584.

In certain embodiments, the gap junction inhibitor comprises a compound of Formula I having the following structure:

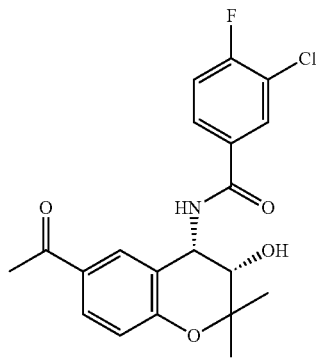 [SMILES: CC(=O)c1ccc2c(c1)[C@H](NC(=O)c1ccc(F)c(Cl)c1)[C@H](O)C(C)(C)O2]

In certain embodiments, the gap junction inhibitor comprises a compound of Formula II having the following structure:

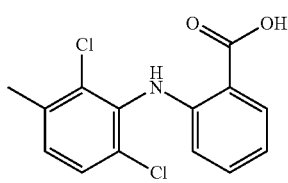 [SMILES: Cc1ccc(Cl)c(Nc2ccccc2C(=O)O)c1Cl]

In certain embodiments, the gap junction inhibitor comprises a compound of Formula III having the following structure:

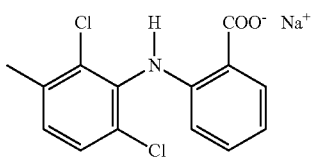

In certain non-limiting embodiments, the gap junction inhibitor can be a salt, a stereoisomer, an analog or a derivative form of the compounds of Formulas I-III. For example, and not by way of limitation, the gap junction inhibitor can include a sodium salt form of Formula II.

In certain non-limiting embodiments, the gap junction inhibitor can be an antibody or antibody fragment that can partially or completely block gap junction formation and/or gap junction patency between cells, gap junction signaling and/or activity. See, for example, Ernesto Oviedo-Orta et al., The FASEB Journal, Vol. 15: 768-774 (2001). In certain non-limiting embodiments, the gap junction inhibitor can be an anti-Connexin compound and/or a Connexin mimetic peptide. See, for example, Evans and Boitano, Biochem. Soc. Trans., Vol. 29(4):606-612 (2001); Dahl, Biophys. J., Vol. 67(5):1816-1822 (1994); European Patent Application Nos. EP2510939 and EP2252320; and U.S. Patent Application No. 2009/0142295.

Further non-limiting examples of gap junction inhibitors include ribozymes, antisense oligonucleotides, short hairpin RNA (shRNA) molecules and siRNA molecules that specifically inhibit and/or reduce the expression or activity of gap junction components. A "ribozyme" refers to a nucleic acid capable of cleaving a specific nucleic acid sequence. In certain non-limiting embodiments, a ribozyme refers to RNA molecules that contain anti-sense sequences for specific recognition, and an RNA-cleaving enzymatic activity, see, for example, U.S. Pat. No. 6,770,633. In contrast, "antisense oligonucleotides" generally are small oligonucleotides complementary to a part of a gene to impact expression of that gene. Gene expression can be inhibited through hybridization of an oligonucleotide to a specific gene or messenger RNA (mRNA) thereof. Methods for using antisense techniques for specifically inhibiting gene expression of genes whose sequence is known are well known in the art (e.g., see U.S. Pat. Nos. 6,566,135; 6,566,131; 6,365,354; 6,410,323; 6,107,091; 6,046,321; and 5,981,732). "Small interfering RNA" or "short interfering RNA" or "siRNA" or "short hairpin RNA" or "shRNA" are forms of RNA interference (RNAi). An interfering RNA can be a double-stranded RNA or partially double-stranded RNA molecule that is complementary to a target nucleic acid sequence. Micro RNAs (miRNA) can also fall in this category. Various modifications to the oligonucleotides of the present invention, e.g., antisense, shRNA or siRNA molecules, can be introduced as a means of increasing intracellular stability and half-life. Non-limiting examples of such modifications include the addition of flanking sequences of ribonucleotides or deoxyribonucleotides to the 5' and/or 3' ends of the molecule, or the use of atypical or non-naturally occurring residues such as phosphorothioate or 2'-O-methyl rather than phosphodiesterase linkages within the oligonucleotide backbone.

The RNA molecules of the invention can be expressed from a vector or produced chemically or synthetically. Methods for selecting an appropriate dsRNA or dsRNA-encoding vector are well known in the art for genes whose sequence is known (e.g., see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and PCT Patent Application Nos. WO 2001/036646, WO 1999/032619 and WO 2001/068836).

5.1.1 Connexin 43 Inhibitors

In certain non-limiting embodiments, the gap junction inhibitor can be specific for a gap junction component. For example, and not by way of limitation, gap junction components include the Connexin family of proteins. A non-limiting example of a Connexin protein is Connexin 43 (Cx43), which is encoded by the gene gap junction protein, al (gial). A Cx43 nucleic acid or protein may be a human Cx43 nucleic acid having the sequence as set forth in NCBI database accession no. NM_000165, NG_008308 or M65188, or a nucleic acid encoding a human Cx43 protein molecule that has the amino acid set forth in NCBI database accession no. NP_000156. According to the present invention, inhibitors of the expression and/or function of such Cx43 nucleic acids and/or proteins may be used as gap junction inhibitors. For example, and not by way of limitation, a gap junction inhibitor can include a Cx43 inhibitor such as, but not limited to, ioxynil or ioxynil octanoate. In certain embodiments, a Cx43 inhibitor can include a Cx43 antibody, antibody fragment or a mimetic peptide (see Danesh-Meyer et al., Brain, 135:506-520 (2012)).

One non-limiting example of a gap junction inhibitor comprises an antisense, shRNA or siRNA nucleic acid sequence homologous to at least a portion of a Cx43 nucleic acid sequence, disclosed above, wherein the homology of the portion relative to the Cx43 sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Non-limiting examples of a shRNA that inhibit Cx43 are set forth in the Example below. In non-limiting embodiments, a Cx43 inhibitor, which is a nucleic acid, may be provided in a Cx43-expressing cancer cell via a vector, for example a lentivirus, which may be selectively targeted to said cancer cell and/or wherein expression of the Cx43 inhibitor nucleic acid may be directed by a promoter which is selectively active in tumor cells.

5.1.2 Protocadherin 7 Inhibitors

The present invention provides Protocadherin 7 (PCDH7) inhibitors for use in the disclosed methods. Non-limiting examples of PCDH7 inhibitors include compounds, molecules, chemicals, polypeptides, proteins that inhibit and/or reduce the expression and/or activity of PCDH7. A PCDH7 nucleic acid or protein may be a human PCDH7 nucleic acid having the sequence as set forth in NCBI database accession no. NM_001173523, NM_032457, NM_032456 or NM_002589, or a nucleic acid encoding a human PCDH7 protein molecule that has the amino acid set forth in NCBI database accession no. NP_001166994, NP_115832, NP_115833 or NP_002580.

In certain non-limiting embodiments, PCDH7 inhibitors can include ribozymes, antisense oligonucleotides, shRNA molecules and siRNA molecules that specifically inhibit and/or reduce the expression or activity of PCDH7. One non-limiting example of a PCDH7 inhibitor comprises an antisense, shRNA or siRNA nucleic acid sequence homologous to at least a portion of a PCDH7 nucleic acid sequence, wherein the homology of the portion relative to the PCDH7 sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. In certain embodiments, antisense, shRNA or siRNA molecules of the present invention may comprise DNA or atypical or non-naturally occurring residues as disclosed above, for example, but not limited to, phosphorothioate residues. Non-limiting examples of a shRNA that inhibits PCDH7 are set forth in the Example below. In non-limiting embodiments, a PCDH7 inhibitor, which is a nucleic acid, may be provided in a PCDH7-expressing cancer cell via a vector, for example a lentivirus, which may be selectively targeted to said cancer cell and/or wherein expression of the PCDH7 inhibitor nucleic acid may be directed by a promoter which is selectively active in tumor cells.

In non-limiting embodiments, a PCDH7 inhibitor can be an antibody or antibody fragment or single chain antibody that specifically binds to PCDH7. Non-limiting examples of such antibodies include ab55506 (Abcam Inc.) and HPA011866 (Sigma-Aldrich). In certain non-limiting embodiments, an anti-PCDH7 antibody or antibody fragment may be used to prepare a human, humanized or otherwise chimeric antibody that is specific for PCDH7 for use according to the invention.

5.1.3 Assay for Gap Junction Activity/Inhibition

Certain non-limiting embodiments of the invention provide for an assay for evaluating gap junction activity, for example assessing inhibition, by measuring levels of cyclic guanosine monophosphate-adenosine monophosphate, e.g., [G(2',5')pA(3',5')p]("cGAMP"), where a decrease in cGAMP correlates with gap junction inhibition. This aspect of the invention is based, at least in part, on the discovery that cGAMP increases when gap junctions form between astrocytes and cancer cells that have metastasized to the brain, and that said elevated cGAMP decreases with Connexin 43 inhibition (see, for example, FIGS. 4B and 14B).

Particular non-limiting embodiments provide for a method for inhibiting growth and/or survival of metastatic cancer cells in the brain of a subject, comprising treating the subject with a therapeutically effective amount of a gap junction inhibitor that produces a decrease in cGAMP relative to the level of cGAMP in the absence of that amount of gap junction inhibitor.

Particular non-limiting embodiments provide for a method of determining whether a brain tumor or metastatic brain tumor in a subject will receive therapeutic benefit from treatment with a gap junction inhibitor, comprising determining whether, in a sample from said tumor, exposure to a gap junction inhibitor leads to a decrease in cGAMP, where a decrease in cGAMP is indicative of therapeutic benefit.

Further non-limiting embodiments of the invention provide for a method of inhibiting growth and/or survival of metastatic cancer cells in the brain of a subject, comprising (i) determining whether the subject will receive therapeutic benefit from treatment with a gap junction inhibitor, comprising determining whether cancer cells of the subject (which may be obtained from a brain metastasis, the primary tumor, or a metastatic tumor outside the brain), when exposed to a gap junction inhibitor, exhibit a decrease in cGAMP relative to the cGAMP level in the absence of the inhibitor, where a decrease in cGAMP is indicative of therapeutic benefit; and (ii) where a decrease in cGAMP is observed, treating the subject with the gap junction inhibitor or, where a decrease in cGAMP is not observed, either assaying another gap junction inhibitor for its ability to decrease cGAMP in the tumor cells or treating the subject with another modality, such as chemotherapy, immunotherapy, radiation therapy, etc. Said determination may be performed, for example, using an in vitro assay as described in the working example below, or a comparable cGAMP measuring system known in the art.

Further non-limiting embodiments of the invention provide for a method of inhibiting growth of a brain tumor in a subject, comprising (i) determining whether the subject will receive therapeutic benefit from treatment with a gap junction inhibitor, comprising determining whether a tumor cell(s) of the subject, when exposed to a gap junction inhibitor, exhibits a decrease in cGAMP relative to the cGAMP level in the absence of the inhibitor, where a decrease in cGAMP is indicative of therapeutic benefit; and (ii) where a decrease in cGAMP is observed, treating the subject with the gap junction inhibitor or, where a decrease in cGAMP is not observed, either assaying another gap junction inhibitor for its ability to decrease cGAMP in the tumor cell(s) or treating the subject with another modality, such as chemotherapy, immunotherapy, radiation therapy, etc. Said determination may be performed, for example, using an in vitro assay as described in the working example below, or a comparable cGAMP measuring system known in the art.

cGAMP may be measured by any method known in the art. In certain non-limiting embodiments of the invention, a cGAMP level is determined by Liquid Chromatography Mass Spectrometry/Mass Spectrometry ("LC-MS/MS"). the LC-MS/MS may be normalized to an internal standard (for example, to account for any losses in the purification steps). As one specific non-limiting example, an assay is described in the working example below, section "cGAMP quantitation by LC-MS/MS," incorporated by reference in this detailed description. See also FIG. 16.

In certain non-limiting embodiments, the present invention provides for a kit to be used in said assay, comprising at least one cGAMP standard, and information regarding decrease of cGAMP with gap junction inhibition in brain tumors.

In certain non-limiting embodiments, the present invention provides for a kit for detecting the amount of cGAMP present within a sample. In certain embodiments, a kit can comprise isotopically labeled cGAMP. For example, and not by way of limitation, the isotopically labeled cGAMP can be used as an internal control in analytical chemistry techniques, e.g., mass spectrometry (MS) and Liquid chromatography (LC)-MS/MS. In certain embodiments, the isotopically labeled cGAMP can be enriched with a low abundance stable isotope such as, but not limited to, 2H (deuterium), 13C (carbon-13), 15N (nitrogen-15) or 18O (oxygen-18).

In certain non-limiting embodiments, a kit of the present invention can further include instructions for using the kit to detect the amount of cGAMP in a sample. For example, and not by way of limitation, the instructions can describe the amount of isotopically labeled cGAMP to add to a sample prior to analysis. In certain embodiments, the instructions can further describe how to calculate the amount of cGAMP in the sample from the amount of isotopically labeled cGAMP added to the sample. In certain non-limiting embodiments, the instructions can describe that reduction in the amount or level of cGAMP in a sample from a subject in response to a gap junction inhibitor, as compared to a reference control level, is indicative of therapeutic benefit from use of the gap junction inhibitor.

5.2 Cancer Targets

In certain embodiments, the present invention provides methods for treating brain metastasis. "Metastasis," as used herein, refers to the presence of one or more cancer cells at a location that is not physically contiguous with the original location of the cancer (e.g., primary cancer). For example, and not by way of limitation, the cancer can include lung cancer, breast cancer, melanoma, colon cancer, kidney cancer, renal cell carcinoma, mesothelioma, ovarian cancer, pancreatic cancer, sarcoma, leukemia, lymphoma, urothelial cancer, head and neck cancer, osteosarcoma and bladder cancer. In certain embodiments, the cancer can include glioblastoma and astrocytoma.

A "detectable" metastasis is a cluster of cells that may be identifiable by magnetic resonance imaging, computerized tomography or positron emission tomography. In certain non-limiting embodiments, a cluster of metastatic cells may include at least about $1 \times 10^7$ cells. In certain embodiments, a detectable metastasis can include a cluster of cells having a size greater than about 5 mm or about 10 mm.

5.3 Pharmaceutical Formulations

In certain non-limiting embodiments, the present invention provides for pharmaceutical formulations of the gap junction inhibitors disclosed above in section 5.1 for therapeutic use. In certain embodiments, the pharmaceutical formulation comprises a gap junction inhibitor and a pharmaceutically acceptable carrier.

"Pharmaceutically acceptable," as used herein, includes any carrier which does not interfere with the effectiveness of the biological activity of the active ingredients, e.g., inhibitors, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioadsorbable matrix materials, implantation elements containing the inhibitor and/or any other suitable vehicle, delivery or dispensing means or material. Such carriers can be formulated by conventional methods and can be administered to the subject.

In certain non-limiting embodiments, the pharmaceutical formulations of the present invention can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral or nasal ingestion by a patient to be treated. In certain embodiments, the pharmaceutical formulation can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion. In certain embodiments, the pharmaceutical formulations of the present invention can be formulated using pharmaceutically acceptable carriers well known in the art that are suitable for parenteral administration.

In certain embodiments, the pharmaceutical formulations suitable for use in the present invention can include formulations where the active ingredients, e.g., gap junction inhibitors, are contained in a therapeutically effective amount. A "therapeutically effective amount" refers to an amount that is able to achieve one or more of an anti-cancer effect, prolongation of survival and/or prolongation of period until relapse. The therapeutically effective amount of an active ingredient can vary depending on the active ingredient, e.g., gap junction inhibitor, formulation used, the cancer and its severity, and the age, weight, etc., of the subject to be treated. In certain embodiments, a patient can receive a therapeutically effective amount of a gap junction inhibitor in single or multiple administrations of one or more formulations, which can depend on the dosage and frequency as required and tolerated by the patient.

An "anti-cancer effect" or "therapeutic benefit" as used herein, refers to one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse) and/or a response with a later relapse or progression-free survival in a patient diagnosed with cancer. In certain embodiments, an anti-cancer effect can refer to the prevention and/or reduction of metastasis of a primary cancer within a subject, e.g., the prevention and/or reduction of metastasis of a cancer to the brain in a subject.

In certain non-limiting embodiments, the gap junction inhibitors described above can be used alone or in combination with one or more anti-cancer agents. An "anti-cancer agent," as used herein, can be any molecule, compound, chemical or composition that has an anti-cancer effect. Anti-cancer agents include, but are not limited to, chemotherapeutic agents, radiotherapeutic agents, cytokines, anti-angiogenic agents, apoptosis-inducing agents, anti-cancer antibodies, anti-cyclin-dependent kinase agents and/or agents which promote the activity of the immune system including, but not limited to, cytokines such as but not limited to interleukin 2, interferon, anti-CTLA4 antibody and/or anti-PD-1 antibody. Non-limiting examples of anti-cancer agents include paclitaxel, temozolomide, vinorelbine, procarbazine, lomustine, vincristine, sFasL and carboplatin. For example, but not by way of limitation, a gap junction inhibitor, e.g., meclofenamate and/or tonabersat, can be used in combination with carboplatin. "In combination with," as used herein, means that the gap junction inhibitor and the one or more anti-cancer agents are administered to a subject as part of a treatment regimen or plan. In certain embodiments, being used in combination does not require that the inhibitor and one or more anti-cancer agents are physically combined prior to administration or that they be administered over the same time frame.

In certain embodiments, where an inhibitor is used in combination with an anti-cancer agent, the amount of each may in some instances be less than a therapeutically effective amount for that agent taken singly, but when both are used therapeutically effectiveness is achieved.

5.4 Methods of Treatment

The present invention relates to methods for treating brain metastasis by inhibiting gap junction functionality. As described in detail in the Example section below, the studies presented in the instant application indicate that inhibition of gap junction signaling and/or formation between the cancer cell and astrocyte can be used to treat brain metastasis. It is based, at least in part, on the discovery that cancer cells expressing Protocadherin 7 and Connexin 43 form gap junctions with astrocytes, which promote the growth of brain metastases, and that inhibition of Protocadherin 7 and/or Connexin 43 expression in cancer cells reduce progression of brain metastases. It is further based on the discovery that treatment with gap junction inhibitors tonabersat and meclofenamate inhibited progression of brain metastatic lesions and enhanced the anti-cancer activity of the conventional chemotherapeutic agent, carboplatin.

Accordingly, the present invention provides methods of treating brain metastasis by inhibiting gap junction signaling and/or formation by the administration of a gap junction inhibitor, disclosed above. Non-limiting examples of gap junction inhibitors, and pharmaceutical formulations thereof, are disclosed in sections 5.1 and 5.3, above. Cancers that can be treated with the methods of the present invention are disclosed above in section 5.2. As such, the present invention relates to methods for inhibiting gap junction functionality to produce an anti-cancer effect in a subject.

A "subject" or "patient," as used interchangeably herein, refers to a human or a non-human subject. Non-limiting examples of non-human subjects include non-human primates, dogs, cats, mice, rats, guinea pigs, rabbits, pigs, fowl, horses, cows, goats and sheep.

In certain non-limiting embodiments, the present invention provides for a method of treating a subject having a cancer comprising administering, to the subject, an amount of a gap junction inhibitor that inhibits metastatic progression of the cancer in the brain. In certain embodiments, the gap junction inhibitor can be meclofenamate, tonabersat, a Cx43 inhibitor and/or a PCDH7 inhibitor. In certain embodiments, the cancer can be breast cancer. In certain embodiments, the cancer can be lung cancer. In certain non-limiting embodiments, one or more cells of the cancer of the subject express Connexin 43 and/or Protocadherin 7. In certain embodiments, the subject was known to have one or more brain metastases prior to treatment. In certain non-limiting embodiments of the present invention, the subject was not known to have a brain metastasis prior to treatment.

In certain embodiments, the method of treating a subject having a cancer comprises administering, to the subject, an amount of tonabersat to inhibit metastatic progression of the cancer in the brain.

In certain embodiments, the method of treating a subject having a cancer comprises administering, to the subject, an amount of meclofenamate to inhibit metastatic progression of the cancer in the brain.

In certain embodiments, the method of treating a subject having a cancer comprises administering, to the subject, an amount of a Cx43 inhibitor to inhibit metastatic progression of the cancer in the brain.

In certain embodiments, the method of treating a subject having a cancer comprises administering, to the subject, an amount of a PCDH7 inhibitor to inhibit metastatic progression of the cancer in the brain.

In certain non-limiting embodiments, the present invention further provides for a method for inhibiting growth and/or survival of metastatic cancer cells in the brain of a subject, comprising administering, to the subject, a therapeutically effective amount of a gap junction inhibitor, disclosed above. In certain embodiments, the gap junction inhibitor can be meclofenamate, tonabersat, a Cx43 inhibitor and/or a PCDH7 inhibitor. In certain embodiments, the cancer is lung cancer and/or breast cancer. In certain non-limiting embodiments, one or more cells of the cancer of the subject express Connexin 43 and/or Protocadherin 7. In certain embodiments, the subject was known to have one or more brain metastases prior to treatment. In certain non-limiting embodiments of the present invention, the subject was not known to have a brain metastasis prior to treatment.

In certain embodiments, the method for inhibiting growth and/or survival of metastatic cancer cells in the brain of a subject comprises administering, to the subject, a therapeutically effective amount of tonabersat.

In certain embodiments, the method for inhibiting growth and/or survival of metastatic cancer cells in the brain of a subject comprises administering, to the subject, a therapeutically effective amount of meclofenamate.

In certain embodiments, the method for inhibiting growth and/or survival of metastatic cancer cells in the brain of a subject comprises administering, to the subject, a therapeutically effective amount of a Cx43 inhibitor.

In certain embodiments, the method for inhibiting growth and/or survival of metastatic cancer cells in the brain of a subject comprises administering, to the subject, a therapeutically effective amount of a PCDH7 inhibitor.

In certain non-limiting embodiments, the present invention provides for a method of treating brain metastasis in a subject comprising administering, to the subject, a therapeutically effective amount of a gap junction inhibitor, disclosed above. In certain non-limiting embodiments, the gap junction inhibitor can be meclofenamate, tonabersat, a Cx43 inhibitor and/or a PCDH7 inhibitor. In certain embodiments, the cancer is lung cancer and/or breast cancer. In certain non-limiting embodiments, one or more cells of the cancer of the subject express Connexin 43 and/or Protocadherin 7. In certain embodiments, the brain metastasis is a detectable metastasis.

In certain embodiments, the method of treating brain metastasis in a subject comprises administering, to the subject, a therapeutically effective amount of tonabersat.

In certain embodiments, the method of treating brain metastasis in a subject comprises administering, to the subject, a therapeutically effective amount of meclofenamate.

In certain embodiments, the method of treating brain metastasis in a subject comprises administering, to the subject, a therapeutically effective amount of a Cx43 inhibitor.

In certain embodiments, the method of treating brain metastasis in a subject comprises administering, to the subject, a therapeutically effective amount of a PCDH7 inhibitor.

In certain non-limiting embodiments, the present invention provides for a method of preventing metastasis of a cancer to the brain in a subject comprising administering, to the subject, a therapeutically effective amount of a gap junction inhibitor, disclosed above. In certain embodiments, the gap junction inhibitor can be meclofenamate, tonabersat, a Cx43 inhibitor and/or a PCDH7 inhibitor. In certain embodiments, the cancer is lung cancer and/or breast cancer. In certain non-limiting embodiments, one or more cells of the cancer of the subject express Connexin 43 and/or Protocadherin 7. In certain non-limiting embodiments of the present invention, the subject was not known to have a brain metastasis prior to treatment.

In certain embodiments, the method of preventing metastasis of a cancer to the brain in a subject comprises administering, to the subject, a therapeutically effective amount of tonabersat.

In certain embodiments, the method of preventing metastasis of a cancer to the brain in a subject comprises administering, to the subject, a therapeutically effective amount of meclofenamate.

In certain embodiments, the method of preventing metastasis of a cancer to the brain in a subject comprises administering, to the subject, a therapeutically effective amount of a Cx43 inhibitor.

In certain embodiments, the method of preventing metastasis of a cancer to the brain in a subject comprises administering, to the subject, a therapeutically effective amount of a PCDH7 inhibitor.

In certain non-limiting embodiments, the present invention provides for a method of reducing the risk of detectable metastasis of a cancer to the brain in a subject having cancer comprising administering, to the subject, a therapeutically effective amount of a gap junction inhibitor, disclosed above. In certain embodiments, the gap junction inhibitor can be meclofenamate, tonabersat, a Cx43 inhibitor and/or a PCDH7 inhibitor.

In certain embodiments, the cancer is lung cancer and/or breast cancer. In certain non-limiting embodiments, one or more cells of the cancer of the subject express Connexin 43 and/or Protocadherin 7. In certain embodiments, the subject was known to have one or more brain metastases prior to treatment. In certain non-limiting embodiments of the present invention, the subject was not known to have a brain metastasis prior to treatment.

In certain embodiments, the method of reducing the risk of detectable metastasis of a cancer to the brain in a subject having cancer comprises administering, to the subject, a therapeutically effective amount of tonabersat.

In certain embodiments, the method of reducing the risk of detectable metastasis of a cancer to the brain in a subject having cancer comprises administering, to the subject, a therapeutically effective amount of meclofenamate.

In certain embodiments, the method of reducing the risk of detectable metastasis of a cancer to the brain in a subject having cancer comprises administering, to the subject, a therapeutically effective amount of a Cx43 inhibitor.

In certain embodiments, the method of reducing the risk of detectable metastasis of a cancer to the brain in a subject having cancer comprises administering, to the subject, a therapeutically effective amount of a PCDH7 inhibitor.

In certain embodiments, the present invention provides a method for lengthening the period of survival of a subject having a cancer comprising administering, to the subject, a therapeutically effective amount of a gap junction inhibitor, disclosed above. In certain embodiments, the gap junction inhibitor can be meclofenamate, tonabersat, a Cx43 inhibitor and/or a PCDH7 inhibitor. In certain embodiments, the cancer is lung cancer and/or breast cancer. In certain non-limiting embodiments, one or more cells of the cancer of the subject express Connexin 43 and/or Protocadherin 7. In certain embodiments, the subject was known to have one or more brain metastases prior to treatment. In certain non-limiting embodiments of the present invention, the subject was not known to have a brain metastasis prior to treatment.

In certain embodiments, the method for lengthening the period of survival of a subject having a cancer comprises administering, to the subject, a therapeutically effective amount of tonabersat.

In certain embodiments, the method for lengthening the period of survival of a subject having a cancer comprises administering, to the subject, a therapeutically effective amount of meclofenamate.

In certain embodiments, the method for lengthening the period of survival of a subject having a cancer comprises administering, to the subject, a therapeutically effective amount of a Cx43 inhibitor.

In certain embodiments, the method for lengthening the period of survival of a subject having a cancer comprises administering, to the subject, a therapeutically effective amount of a PCDH7 inhibitor.

In certain embodiments, the methods of the present invention can lengthen the survival period of a subject having cancer by about 1 month, about 2 months, about 3 months, about 4 months, about 6 months, about 8 months, about 10 months, about 12 months, about 14 months, about 18 months, about 20 months, about 2 years, about 3 years, about 4 years, about 5 years, about 6 years or more.

In certain embodiments, a method for treating cancer cell metastasis in a subject in need of such treatment comprises administering, to the subject, a therapeutically effective amount of a gap junction inhibitor, disclosed above, to inhibit cancer cell-astrocyte gap junction functionality.

In certain embodiments, the present invention provides a method of producing an anti-cancer effect in a subject having a cancer comprising administering, to the subject, a therapeutically effective amount of a gap junction inhibitor, disclosed above.

In certain embodiments, the present invention provides a method of producing an anti-cancer effect in a subject having a cancer comprising administering, to the subject, a therapeutically effective amount of a gap junction inhibitor, disclosed above, to inhibit cancer cell-astrocyte gap junction functionality.

In certain embodiments, the present invention provides a method of producing an anti-cancer effect in a subject having a cancer comprising administering, to the subject, a therapeutically effective amount of a gap junction inhibitor to inhibit gap junction functionality.

In certain embodiments, the present invention provides methods for treating a subject that has cancer, for inhibiting the growth and/or survival of cancer cells, for preventing and/or delaying the reoccurrence of a cancer, for inhibiting the infiltration of cancer cells and for lengthening the period of survival of a subject having cancer, comprising, administering, to the subject, a therapeutically effective amount of a gap junction inhibitor, disclosed above. In certain embodiments, the cancer is glioblastoma and/or astrocytoma.

In certain embodiments, the methods of the present invention can further comprise administering to the subject an anti-cancer agent, as described above. For example, and not by way of limitation, a method of the present invention comprises administering, to the subject, a therapeutically effective amount of a gap junction inhibitor and a therapeutically effective amount of an anti-cancer agent that can penetrate the blood brain barrier to achieve therapeutic levels, such as, but not limited to ACNU, BCNU, CCNU, hydroxyurea, topotecan, temozolomide, dacarbazine, methotrexate, Ara-C, capecitabine, cisplatin, vinorelbine, carboplatin, or combinations thereof.

In certain embodiments, a method of the present invention comprises administering, to the subject, a therapeutically effective amount of meclofenamate and a therapeutically effective amount of carboplatin.

In certain embodiments, a method of the present invention comprises administering, to the subject, a therapeutically effective amount of tonabersat and a therapeutically effective amount of carboplatin.

In certain embodiments, a method of the present invention comprises administering, to the subject, a therapeutically effective amount of a Cx43 inhibitor and a therapeutically effective amount of carboplatin.

In certain embodiments, a method of the present invention comprises administering, to the subject, a therapeutically effective amount of a PCDH7 inhibitor and a therapeutically effective amount of carboplatin.

In a specific non-limiting embodiment, a gap junction inhibitor can be administered at an amount of about 1 mg/kg to about 30 mg/kg. For example, and not by way of limitation, a gap junction inhibitor can be administered at an amount of about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 30 mg/kg, about 10 mg/kg to about 30 mg/kg, about 15 mg/kg to about 30 mg/kg, about 20 mg/kg to about 30 mg/kg or about 25 mg/kg to about 30 mg/kg. In certain non-limiting embodiments, the gap junction inhibitor can be administered at an amount of about 0.08 mg/kg to about 3.6 mg/kg (see Reagan-Shaw et al., The FASEB J., Vol. 22: 659-661 (2008)). In certain non-limiting embodiments, the gap junction inhibitor can be administered at an amount of about 0.15 mg/kg to about 18 mg/kg.

In certain non-limiting embodiments, the gap junction inhibitor can be administered at an amount of about 1 mg to about 200 mg. For example, and not by way of limitation, a gap junction inhibitor can be administered at an amount of about 1 mg to about 200 mg, about 10 mg to about 200 mg, about 20 mg to about 200 mg, about 30 mg to about 200 mg, about 40 mg to about 200 mg, about 50 mg to about 200 mg, about 60 mg to about 200 mg, about 70 mg to about 200 mg, about 80 mg to about 200 mg, about 90 mg to about 200 mg, about 100 mg to about 200 mg, about 110 mg to about 200 mg, about 120 mg to about 200 mg, about 130 mg to about 200 mg, about 140 mg to about 200 mg, about 150 mg to about 200 mg, about 160 mg to about 200 mg, about 170 mg to about 200 mg, about 180 mg to about 200 mg, about 190 mg to about 200 mg, about 1 mg to about 190 mg, about 1 mg to about 180 mg, about 1 mg to about 170 mg, about 1 mg to about 160 mg, about 1 mg to about 150 mg, about 1 mg to about 140 mg, about 1 mg to about 130 mg, about 1 mg to about 120 mg, about 1 mg to about 110 mg, about 1 mg to about 100 mg, about 1 mg to about 90 mg, about 1 mg to about 80 mg, about 1 mg to about 70 mg, about 1 mg to about 60 mg, about 1 mg to about 50 mg, about 1 mg to about 40 mg, about 1 mg to about 30 mg about 1 mg to about 20 mg, about 1 mg to about 10 mg or about 1 mg to about 5 mg.

In certain embodiments, the gap junction inhibitor tonabersat can be administered at an amount of about 10 mg/kg. In certain embodiments, the gap junction inhibitor tonabersat can be administered at an amount of about 0.8 mg/kg to about 1.2 mg/kg. In certain embodiments, the gap junction inhibitor tonabersat can be administered at an amount of about 0.01 mg/kg to about 9 mg/kg. In certain embodiments, the gap junction inhibitor meclofenamate can be administered at an amount of about 20 mg/kg. In certain embodiments, the gap junction inhibitor meclofenamate can be administered at an amount of about 1.6 mg/kg to about 2.4 mg/kg. In certain embodiments, the gap junction inhibitor meclofenamate can be administered at an amount of about 0.1 mg/kg to about 19 mg/kg. In certain embodiments, the gap junction inhibitor meclofenamate can be administered at an amount of between about 100 mg to about 400 mg daily. In certain embodiments, the gap junction inhibitor meclofenamate can be administered at an amount of about 100 mg twice daily. In certain embodiments, a subject is treated concurrently with a proton-pump inhibitor and meclofenamate. In certain embodiments, the gap junction inhibitor meclofenamate can be administered at an amount of about 100 mg twice daily, the subject may be treated concurrently with a proton-pump inhibitor and meclofenamate, and the treatment period may be at least about 2 months, at least about 4 months, or at least about 6 months.

In a specific non-limiting embodiment, an anti-cancer agent can be administered at an amount of about 1 nM to about 1 µM and/or about 10 mg/kg to about 100 mg/kg. In a specific non-limiting embodiment, an anti-cancer agent can be administered at an amount of about 0.8 mg/kg to about 8 mg/kg. In a specific non-limiting embodiment, an anti-cancer agent can be administered at an amount of about 1.2 mg/kg to about 60 mg/kg. For example, and not by way of limitation, the anti-cancer agent carboplatin can be administered at an amount of about 500 nM and/or about 50 mg/kg. In certain embodiments, the anti-cancer agent carboplatin can be administered at an amount of about 4 to about 6 mg/kg. In certain embodiments, the anti-cancer agent Paclitaxel can be administered at an amount of about 25 nM.

In certain embodiments, the gap junction inhibitors of the present invention can be administered once, twice, three, four, five or six times per week, or daily. In certain embodiments, the anti-cancer agents of the present invention can be administered once, twice, three, four, five, or six times per week, or daily. In certain embodiments, the inhibitors and/or anti-cancer agents of the presently disclosed subject matter can be administered one or more times per day. For example, and not by way of limitation, the gap junction inhibitors and/or anti-cancer agents of the present invention can be administered once, twice, three, four, five or more times a day.

An inhibitor and/or an anti-cancer agent, disclosed herein, can be administered to the subject using standard methods of administration. In certain embodiments, the inhibitor can be administered to the subject orally or parenterally. For example, and not by way of limitation, the route of administration can be intravenous, intraarterial, intrathecal, intraperitoneal, intramuscular, subcutaneous, topical, intradermal, locally or combinations thereof. In certain embodiments, the inhibitor can be administered to the patient from a source implanted in the patient. In certain embodiments, administration of the inhibitor can occur by continuous infusion over a selected period of time.

The following example is merely illustrative of the presently disclosed invention and should not be considered as a limitation in any way.

6. EXAMPLE 1: PROTOCADHERIN 7 AND CONNEXIN 43 MEDIATE CARCINOMA-ASTROCYTE GAP JUNCTIONS AND BRAIN METASTASIS

6.1 Materials and Methods

Cell culture.

Human MDA-MB-231 (MDA231), murine MMTV-neu, their metastatic derivatives, and murine 373N1, 393N1, 482N1, 2691N1 cell lines were cultured in DMEM with 10% fetal bovine serum (FBS) and 2 mM L-Glutamine. Human H2030 cells and metastatic derivatives were cultured in RPMI 1640 medium supplemented with 10% FBS and 2 mM L-Glutamine. For lentivirus production, 293T cells were cultured in DME media supplemented with 10% fetal bovine serum and 2 mM L-glutamine. Human primary astrocytes, brain microvascular endothelial cells (HBMEC), adult dermal fibroblasts, and microglia were cultured in media specified by the supplier (ScienCell), and used between passages 2-6. All cells tested negative for micoplasma.

Animal Studies.

All experiments using animals were done in accordance to protocols approved by the MSKCC Institutional Animal Care and Use Committee. Athymic NCR nu/nu mice (NCI-Frederick), Cr:NIH bg-nu-xid mice (NCI-Frederick) and B6129SF1/J mice (Jackson Laboratory) were use at 5-6 weeks of age. For long-term brain metastasis assays we followed previously described procedures (Bos, Nguyen et al. 2010). In brief, $10^4$ MDA231-BrM2 cells, $5 \times 10^4$ H2030-BrM3 cells, or $10^5$ 393N1 cells suspended in 100 μl of PBS were injected into the left cardiac ventricle. At the experimental endpoint, anesthetized mice (ketamine 100 mg/kg, xylazine 10 mg/kg) were injected retro-orbitally with D-luciferin (150 mg/kg), and brain colonization was quantified by ex vivo Bio-luminescent imaging (BLI). For short-term (7-day and 14-day) brain metastasis experiments, we injected $5 \times 10^5$ cells. TRITC dextran (70 KD) (Life Technologies) was intravenously injected to stain vascular structures. For inducible knockdown experiments, mice were given doxycycline hyclate (Sigma-Aldrich) in the drinking water (2 mg/mL) and the diet (Harlan) 14 days after injection of cancer cells. For lung colonization assays, $2 \times 10^5$ MDA231-BrM2 cells in 100 piL PBS were injected into the lateral tail vein. For orthotopic tumour implantation, $5 \times 10^3$ cells in 50 piL of 1:1 mix of PBS/growth factor reduced matrigel (BD Biosciences) were injected into the 4th right mammary fat pad of female mice. For drug treatment experiments, mice were intraperitoneally injected with carboplatin (Hospira) (50 mg/kg/5 days), Tonabersat (Med-Chem Express) (10 mg/kg/day), or meclofenamic acid sodium salt (Sigma-Aldrich) (20 mg/kg/day). Vehicle (10% DMSO in Polyethylene glycol 400) was used in control mice. BLI was performed using an IVIS Spectrum Xenogen instrument (Caliper Life Sciences) and analysed using Living Image software, v. 2.50. For brain metastasis assays, 8-10 mice were used in each group. For drug treatment experiments, mice were inoculated with cancer cells and randomly assigned to treatment groups. Gap junction modulators and chemotherapeutic agents were blindly administered in the MSKCC Antitumour Assessment Core.

Knockdown and Overexpression Constructs.

For stable knockdown of Cx43 and PCDH7, we used shRNAs in lentiviral vectors. For inducible knockdown, shRNAs in TRIPZ lentivial vector were used. 1 μg/mL doxycycline hyclate (Sigma-Aldrich) was added to induce the expression of shRNA. Targeted sequences of shRNAs are listed Table 1, below. pBabe-Puro-IKBalpha-mut (Addgene) was used for stable expression of SR-IkB. For expression of wild type Cx43 (Origene), or Cx43(T154A) mutant (ACC to GCC), we used pLVX vector.

mRNA and Protein Detection.

Total RNA was extracted using the PrepEase RNA spin kit (USB). To prepare cDNA, 1 μg of total RNA was treated using the Transcriptor First Strand cDNA synthesis kit (Roche). Cx43, Cx30 and Cx 26 expression was quantified by Taqman gene expression assay primers: (Cx 43: Hs00748445_s1, Mm00439105_ml; Cx30: Hs00922742_s1, Mm00433661_s1; Cx26: Hs00269615_s1, Mm00433643_s1; Applied Biosystems). Relative gene expression was normalized relative to β2-microglobulin (Hs99999907_m1, Mm00437762_m1). The PCDH7 primer pair was designed to detect all PCDH7 isoforms: 5'-agtt-caacgtggtcatcgtg-3'(sense), 5'-acaatcagggagttgttgctc-3'(antisense). Reactions were performed using SYBR Green I Master Mix (Applied Biosystems). Quantitative expression data were analyzed using an ABI Prism 7900HT Sequence Detection System (Applied Biosystems). For western immunoblotting, cell pellets were lysed with RIPA buffer and protein concentrations determined by BCA Protein Assay Kit (Pierce). Protein lysates of primary human astrocytes, neurons, microglia and HBMEC were purchased from ScienCell. Proteins were separated by SDS-PAGE and transferred to nitrocellulose membranes (BioRad). Antibodies used for western blotting are listed in Table 2, below.

Dye Transfer and EdU Transfer Assays.

Monolayers of cancer cells or astrocytes were labeled with 2.5 gig/ml calcein Red-Orange AM dye (Life Technologies) at 37° C. for 30 min. Single cell suspensions were mixed at a ratio of 2:1 labeled:unlabeled cells for 6 h. Certain experiments used a mix of three cell populations, MDA231-BrM2 (GFP+), HBMEC (pre-labeled with Cell Proliferating Dye Fluor@670, eBioscience), and unlabeled astrocytes. Dye transfer was visualized by Zeiss LSM 5 Live confocal microscopy (20-min time-lapse) or quantified by FACSCalibur flow cytometry (BD Biosciences) at different time points. For DNA transfer assays, cancer cells were labeled overnight with EdU (10 μM, Molecular Probes) and maintained in culture for additional 3 days. Single cell suspensions of labeled cancer cells and astrocytes were mixed at 2:1 ratio for 6 h. EdU transfer was visualized using Zeiss LSM 5 Live confocal microscopy or quantified by FACSCalibur flow cytometry (BD Biosciences) following the manufacturer's instructions (Molecular Probes).

Cancer Cell and Astrocyte Co-Culture Experiments.

Astrocytes and cancer cells were mixed at ratio of 1:1. For apoptosis assays, overnight co-cultures were treated with 500 ng/ml sFasL (Peprotech) in serum free media, 500 nM carboplatin (Sigma-Aldrich) or 25 nM Paclitaxel (Sigma-Aldrich) for 24 h. Single cell suspensions were stained with APC-conjugated cleaved caspase 3 antibody (Cell Signaling), apoptotic GFP+ cancer cells were detected by flow cytometery. For translating ribosome affinity purification (TRAP), EGFP-L10a expressing cancer cells were co-cultured with astrocytes for 24 h. Following previously published protocols, (Heiman, Schaefer et al. 2008, Zhang, Jin et al. 2013) mRNA purified from cancer cells were was used for library construction with TruSeq RNA Sample Prep Kit v2 (Illumina) following the manufacturer's instructions. Samples were barcoded and run on a Hiseq 2000 platform in a 50 bp/50 bp paired-end run, using the TruSeq SBS Kit v3 (Illumina). An average of 50 million paired reads were generated per sample. For conditioned media analysis, media were collected after 24 h, and cytokines in the conditioned media were either identified using Human Cytokine Array (R&D systems) or measured by IFNα or TNFα ELISA kits (R&D systems). To detect the activity of IFNα or TNFα in the collected conditioned media, cancer cells were treated with the collected conditioned media for 2 h and phosphorylation status of STAT1 or NF-κB p65 was determined by western blotting. For cGAMP and TBI-IRF3 activation experiments, cancer cells and astrocytes were co-cultured for 18 h. The phosphorylation status of TBK1, IRF3 was determined by western immunoblotting. Nuclear translocation of IRF3 was determined by immunofluorescence staining with Zeiss LSM 5 Live confocal microscopy. cGAMP levels were determined by LC-MS/MS.

Cytokine Treatment and Pathway Reporter Assays.

Cancer cells were treated with 10 units/ml (39 u/ng) recombinant IFNαA (R&D Systems) or 10 µg/ml recombinant TNFα (R&D Systems) in combination with carboplatin or Taxol (Sigma-Aldrich) for 24 h. Apoptosis was quantified by Caspase-Glo 3/7 assay (Promega). For NFκB reporter assays, the NF-κB responsive sequence from the pHAGE NFKB-TA-LUC-UBC-dTomato-W construct (Addgene) (Wilson, Kwok et al. 2013) was cloned into a pGL4.82 Renilla luciferase reporter (Promega). Cancer cells were co-transfected with this vector and a LeGO-C2 mCherry vector (Addgene). Renilla luciferase activity was determined using RenillaGlo Luciferase system (Promega). Red fluorescence signal was used to normalize transfection efficiency.

Immunohistochemical Staining.

Mouse brains were fixed with 4% paraformaldehyde, sectioned by vibratome (Leica) or cryostat (Leica) and stained following established protocols (Valiente, Obenauf et al. 2014). For brain slice assays (Valiente, Obenauf et al. 2014), 250 µm thick slices of adult mouse brain were prepared with a vibratome (Leica) and placed on top of 0.8 µm pore membranes (Millipore) in brain slice culture medium (DMEM, complete HBSS, 5% FBS, 1 mM L-glutamine, 100 IU/mL penicillin, 100 µg/mL streptomycin). $3 \times 10^5$ cancer cells were placed on the surface of the slice. After 48 h of incubation, brain slices were fixed with 4% paraformaldehyde, and stained. For immunostaining in chamber slide cultures, cells were fixed with 4% paraformaldehyde and stained. Antibodies used for immunochemical staining are listed in Table 2. Images were acquired with Zeiss Axio Imager.Z1 microscope or Leica SP5 upright confocal microscope, and analyzed with ImageJ, Imaris and Metamorph softwares. Antibodies used for immunostaining are listed in Table 2.

Split Luciferase Assay.

Fusion cDNAs were generated by deleting the stop codon in human Cx43 (Origene), PCDH7 (Origene), E-cadherin (Addgene) or N-cadherin (Addgene) cDNAs and splicing the N-terminal or C-terminal fragment of firefly luciferase (Luker, Smith et al. 2004). (Addgene). Constructs were cloned into pLVX lentiviral expression vector and transduced into non-GFP-luciferase-labeled parental MDA-MB-231 or H2030 cells. To detect luciferase activity, 7.5 mg/ml D-luciferin potassium salt was added in the culture media. BLI was performed by IVIS Spectrum Xenogen instrument, using Living Image software v.2.50.

Cytosolic dsDNA Detection.

For visualization of dsDNA, cells were immunostained with anti-dsDNA antibody. Anti-GFP staining was used to delineate cancer cell bodies, DAPI to distinguish nuclei, and anti-CoxIV antibody (a mitochondrial marker) to distinguish mitochondria. Phalloidin staining (Molecular Probe) was used to delineate astrocyte cell bodies. For quantification of dsDNA, nuclear, cytosolic and mitochondrial fractions were prepared using a mitochondria isolation kit (Thermo Scientific). DNA from all subcellular fractions was purified by QIAamp DNA mini kit (Qiagen) and quantified by QuantoFluor dsDNA system (Promega).

Bioinformatic and Statistical Analysis.

Bioinformatic analysis was performed in R (ver. 3.1.2) unless otherwise noted. The data were analyzed using the TopHat2-HTSeq-DESeq2 pipeline (Anders, McCarthy et al. 2013, Kim, Pertea et al. 2013, Love, Huber et al. 2014). Differential gene expression was compared with cooksCutoff and independentFiltering turned off. Scatter plot showing fold changes was produced using the ggplot2 package. Principal component analysis (PCA) was performed usingprcomp. Pathway gene response signatures were analyzed and scored by the sum of z-score method (Zhang, Jin et al. 2013), as previously described (Nguyen, Chiang et al. 2009, Gatza, Lucas et al. 2010). Multiple hypothesis testing was adjusted using the Benjamini & Hochberg false-discovery-rate method. Statistical analysis was performed using GraphPad software (Prism) and Student's t-test (two-tailed). P values <0.05 were considered statistically significant. Values are averages±standard error of the mean (S.E.M.).

Clinical Sample Analysis.

CX43 and PCDH7 transcript levels were analyzed in the microarray data of primary breast cancer (EMC-MSK) and adenocarcinoma datasets (MSKCC set2, GSE3141 and GSE8893). Multiple probes mapping to the same gene were combined by selecting the probe with maximal variance across samples. Triple-negative breast cancer subtypes were identified either based on clinical annotation of the data set or on ESR1 and ERBB2 transcript levels. The hazard ratio of the CX43 and PCDH7 values was computed based on Cox proportional hazards model, as implemented by the "coxph" command in R. P values were calculated from a Cox proportional hazard model, with CX43 and PCDH7 expression treated as a continuous variable. For Cx43 immunohistochemistry, normal lung tissue array (75 cases), primary triple negative breast cancer tissue array (98 cases) and primary non-small cell lung carcinoma tissue array (138 cases) were purchased from US Biomax. Paraffin embedded tissue microarrays from brain metastases (117 case of triple-negative breast cancer, 91 cases of non-small cell lung carcinoma) were obtained from the MSKCC Department of Pathology in compliance with the MSKCC Institutional Review Board. Informed consent was obtained from all subjects. Immunohistochemical staining for Cx43 was performed by the MSKCC Pathology Core Facility using standardized, automated protocols. For matched primary-brain metastatic lesions, Cx43 staining images was quantified by positive staining area (Metamorph software).

cGAMP Quantitation by LC-MS/MS.

Cells (2.4 million MDA231-BRM2 or Human Astrocytes alone, 2.4 million Human Astrocytes+2.4 million MDA231-BRM2 co-culture) were seeded in 10 cm dishes. After 18 h culture media was aspirated and replaced with 2 mL 80:20 methanol:water containing 4 nM c-di-GMP internal standard. Dishes were incubated at −80° C. overnight to promote protein precipitation, scraped and transferred to 2 mL centrifuge tubes. Samples were subjected to 2 vortex, freeze/thaw cycles in liquid nitrogen, sonicated in an ice water bath at full power for 5 min, and clarified by centrifugation at 21,000×g for 20 min at 4° C. Extracts were dried using a bench top evaporator (Genevac) and reconstituted in 100 µL of 0.1% formic acid in water. Liquid chromatography separation was performed using a Shimadzu HPLC, Accela Open autosampler (Thermo) and Cortecs C18+ column (Waters, 150 mm×2.1 mm, 2.7 µm). Samples were maintained at 4° C. and injection volume was 15 µL. The aqueous mobile phase (A) was 0.1% formic acid in water and the organic mobile phase (B) was 0.1% formic acid in acetonitrile. Initial conditions were 0% B with gradient program: 1.0 min: 0% B; 7 min: 20% B; 7.1 min: 90% B; 9.0 min: 90% B and 5 min re-equilibration time. Flow rate was 400 µL/min, with a post-column solvent of 90:10 acetone:DMSO added to the LC stream using a zero-dead volume tee at 120 µL/min to boost detection sensitivity. Cyclic nucleotides were detected using a TSQ Vantage mass spectrometer (Thermo) operating in SRM and positive ionization modes. Source parameters were: spray voltage: 4000 V; vaporizer temperature: 200° C., sheath gas pressure: 70 psi; aux gas pressure: 20 psi, capillary temperature: 400° C. Compound-specific S-lens values were: 164 V (cGAMP) and 190 V (c-di-GMP). Individual reactions monitored and collision energies were: cGAMP m/z 675.1→m/z 512.1 (CE: 19 V), m/z 312.0 (CE: 40 V), m/z 136.0 (CE: 39 V)* and c-di-GMP m/z 675.1→m/z 540.1 (CE: 19 V), m/z 248.0 V (CE: 27 V), m/z 152.0 (CE: 31 V)*, * indicating the primary transition used to quantify each cyclic nucleotide. Retention times and transitions were confirmed relative to cyclic [G(2',5')pA(3',5')p] and c-di-GMP metabolite standards (BioLog). Data analysis was performed using Xcalibur software (Thermo) and Prism (GraphPad).

6.2 Results

Brain Metastasis Linked to Cx43 Gap Junction Formation

Lung and breast cancers are the most common sources of brain metastasis (Gavrilovic and Posner 2005). We employed four brain metastatic models derived from mammary (MDA231-BrM2, ErbB2-BrM) or lung adenocarcinomas (H2030-BrM3, Kras/p53-BrM), of either human or murine origin (FIG. 6a) (Bos, Zhang et al. 2009, Nguyen, Chiang et al. 2009, Winslow, Dayton et al. 2011, Valiente, Obenauf et al. 2014). When implanted as orthotopic tumours or inoculated into the arterial circulation of mice, these cells form lesions that replicate key histopathologic features of brain metastasis, including marked astrocytosis (FIG. 1a) (Bos, Zhang et al. 2009, Nguyen, Chiang et al. 2009, Valiente, Obenauf et al. 2014). In all these models, brain metastatic cells produce anti-PA serpins to prevent generation of lethal plasmin by reactive astrocytes (Valiente, Obenauf et al. 2014). However, co-culture with astrocytes protected cancer cells from chemotherapy and the pro-apoptotic cytokine FasL (FIG. 6b), congruent with previous in vitro findings (Kim, Kim et al. 2011). These results suggested a possible dual role of astrocytes in brain metastasis.

Astrocytes interact in a vast gap-junction network (Theis and Giaume 2012, Haydon and Nedergaard 2015). Connexin 43 (Cx43) is one of the principal gap junction proteins in astrocytes. In our brain metastatic mouse model, we observed Cx43 expression at the interface of cancer cells and surrounding astrocytes (FIG. 1b). Cx43 can mediate interactions between cancer cells and endothelial cells (Cai, Jiang et al. 1998) and astrocytes (Zhang, Iwakuma et al. 2009) proposed to be pro-metastatic (Pollmann, Shao et al. 2005) or anti-metastatic (Sharma, Abraham et al. 2010). To determine the clinical association of Cx43 with brain metastasis, we assayed patient tissue samples. In triple-negative breast cancer and non-small cell lung cancer (NSCLC), we found a higher level of Cx43 staining in brain metastases than in primary tumours or normal tissues (FIG. 1c-d).

Gap junctions are formed by hexameric connexin hemi-channels. Pairwise interactions between hemi-channels on adjacent cells form pores for the traffic of cytosolic molecules (Bennett and Goodenough 1978, Oshima 2014). Not all gap junctions form functional pores (Stoletov, Strnadel et al. 2013), (Sharma, Abraham et al. 2010). However, we observed time-dependent transfer of calcein from brain metastatic cells to astrocytes, as shown by time-lapse fluorescence microscopy (FIG. 1e; FIG. 6c), and from astrocytes to metastatic cells, as shown by flow cytometry (FIG. 6d).

Brain Metastases Upregulate Protocadherin 7.

Astrocyte calcein transfer occurred more readily with brain metastatic cells than with their parental counterparts (FIG. 1f). This phenotype was not fully explained by higher Cx43 expression in the brain metastatic derivatives (FIG. 1g, FIG. 7a,b). Moreover, Cx43 expression in the metastatic cells was lower than, or similar to that in astrocytes, neurons, or brain microvascular endothelial cells (FIG. 1h, FIG. 7c). The expression level of other astrocytic connexins (Cx26, Cx30) in brain metastatic cells was similar to that of parental cells (FIG. 7d). These observations raised the question of how metastatic cells could compete for gap junction formation with resident astrocytes.

Reasoning that cancer cells must use another component besides Cx43 to engage astrocytes, we investigated protocadherin 7 (PCDH7), one of a small group of genes that are upregulated in brain metastatic cells from both breast and lung tumours (Bos, Zhang et al. 2009, Nguyen, Chiang et al. 2009, Valiente, Obenauf et al. 2014). Protocadherins are integral membrane proteins with seven cadherin repeats that direct cell-cell contacts by homophilic interaction. PCDH7 (also known as cadherin-related neuronal receptor) is the sole protocadherin expressed predominantly in the brain (Yoshida, Yoshitomo-Nakagawa et al. 1998, Kim, Chung et al. 2007); its function is unknown. PCDH7 levels were higher in brain metastatic derivatives than in parental cell lines (FIG. 1g, FIG. 7a,b) or in matched derivatives that are highly metastatic to bone or lung but not brain (FIG. 1i; refer to FIG. 6a). The PCDH7 level in brain metastatic cells was higher than in astrocytes, neurons, microglia or endothelial cells (FIG. 1h, FIG. 7c).

In clinical cohorts of triple-negative breast cancer with site of relapse annotation, combined expression of PCDH7 and Cx43 in primary tumours was associated with brain metastasis, but not bone or lung metastasis (FIG. 1j). Although most NSCLC datasets are not annotated with site-specific metastasis information, a large proportion (up to 70%) of relapses in these patients include brain metastases (Gaspar, Chansky et al. 2005). Due to the profound morbidity and mortality associated with brain metastases (Gaspar, Scott et al. 2000), these contribute disproportionately to metastasis-free survival. Indeed, Cx43 and PCDH7 expression was associated with decreased metastasis-free survival of NSCLC patients in three cohorts (FIG. 1k, FIG. 7e). These results all support the hypothesis that PCDH7 and Cx43 are relevant in brain metastasis.

PCDH7 Directs Carcinoma-Astrocyte Gap Junctions.

Brain-metastatic cells depleted of either PCDH7 or Cx43 by means of short hairpin RNAs (shRNA) (FIG. 7f,g)

showed reduced capacity for dye transfer to astrocytes compared to controls (FIG. 2a, FIG. 8a). The extent of dye-transfer inhibition after Cx43 depletion was comparable to that obtained with the pan-connexin inhibitor, carbenoloxone (FIG. 8b). Given the ability of cadherins to establish homophilic binding between molecules on adjacent cells (Yagi and Takeichi 2000), we hypothesized that astrocyte PCDH7 might participate in the formation of gap junctions with cancer cells. Indeed, PCDH7 depletion in astrocytes (FIG. 8c) also inhibited dye transfer from MDA231-BrM2 cells (FIG. 8d).

Figure 8E:
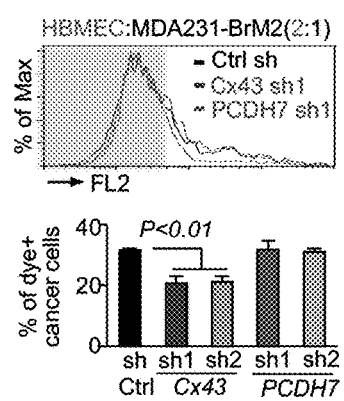
Figure 8F:
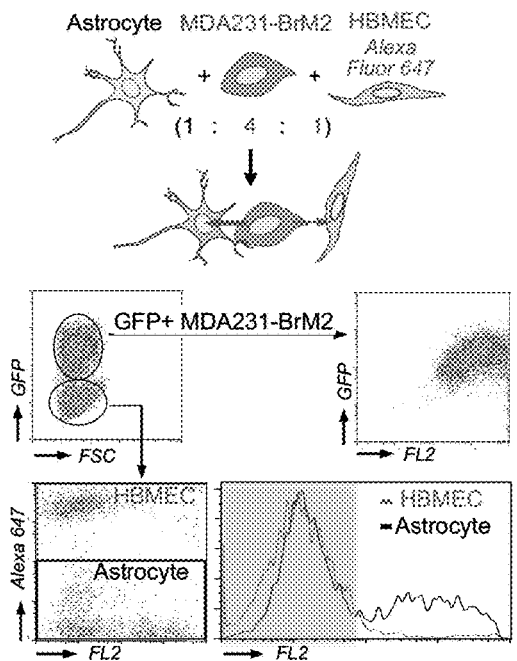
Figure 8G:
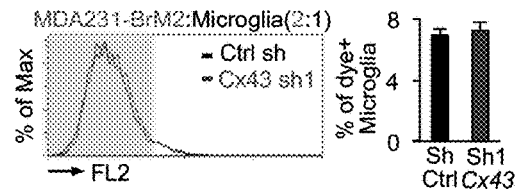
Figure 8H:
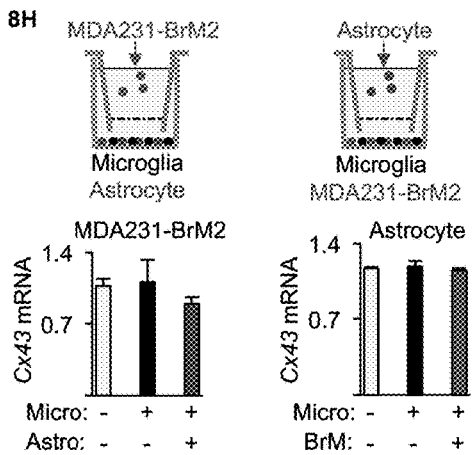

Human brain microvascular endothelilal cells (HBMECs) express much lower levels of Cx43 than astrocytes, and have no detectable PCDH7 expression (FIG. 1h, FIG. 7c). A low level of PCDH7-independent gap junction communication occurred between cancer cells and HBMECs (FIG. 8e). In a competition experiment, dye transfer between cancer cell and astrocyte was favored over dye transfer between cancer cell and endothelial cell (FIG. 8f). Primary microglia cells expressed very low levels of Cx43 and PCDH7 and did not accept calcein from cancer cells (FIG. 8g). Cx43 levels in astrocytes and cancer cells remained constant after co-culture with microglia (FIG. 8h). Thus, PCDH7 directs cancer cells to preferentially form Cx43 gap junctions with astrocytes.

Figure 9A:
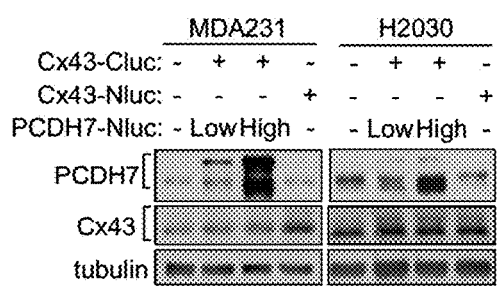
Figure 9B:
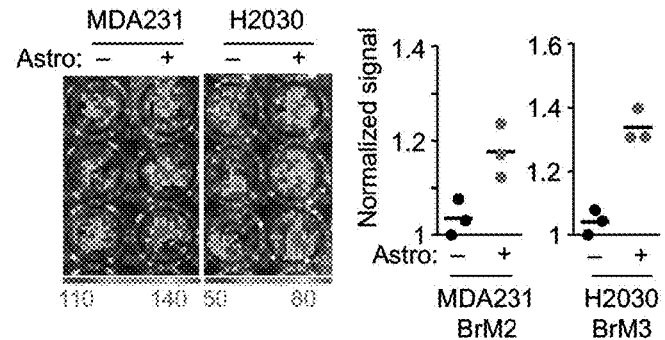
Figure 9C:
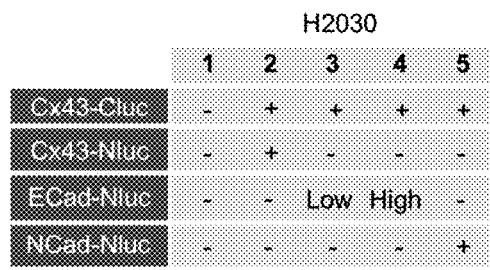
Figure 9D:
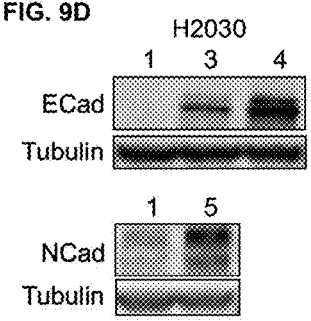
Figure 9E:
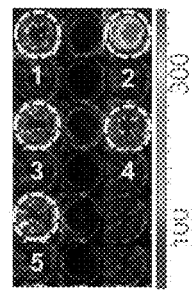

We employed a split luciferase complementation assay (Luker, Smith et al. 2004) to detect PCDH7 interactions with Cx43 in live cells. Constructs encoding PDCH7 and Cx43 fused to the N-terminal (NLuc) and C-terminal (CLuc) halves of firefly luciferase were expressed in relevant combinations in non-GFP-luciferase labeled parental cells (FIG. 2b). When NLuc and CLuc come into proximity, luciferase activity is reconstituted. Because Cx43 self-assembles into hexameric semi-channels in the cell membrane, transduction of cells with Cx43-NLuc and Cx43-CLuc vectors served as positive control (FIG. 2b). We detected specific luciferase activity in cells expressing both Cx43-CLuc and PCDH7-NLuc (FIG. 2b). The expression level of PCDH7 and Cx43 was higher than the endogenous levels in the parental cells but lower than, or comparable to the levels in brain metastatic cells (FIG. 9a). Moreover, co-culture with astrocytes increased the luciferase signal in the cancer cells (FIG. 9b) suggesting that astrocyte Cx43 and PCDH7 induce further clustering of cancer cell Cx43-CLuc and PCDH7-NLuc. No activity was detected when N-cadherin or E-cadherin were fused with NLuc and co-expressed with Cx43-CLuc (FIG. 9c-e).

Figure 10A:
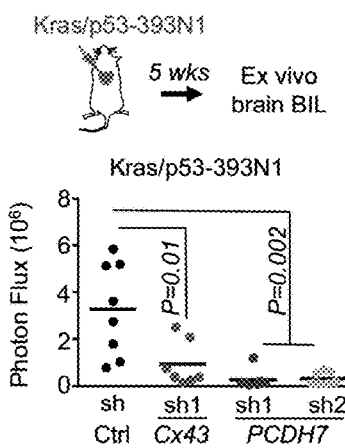
Figure 10B:
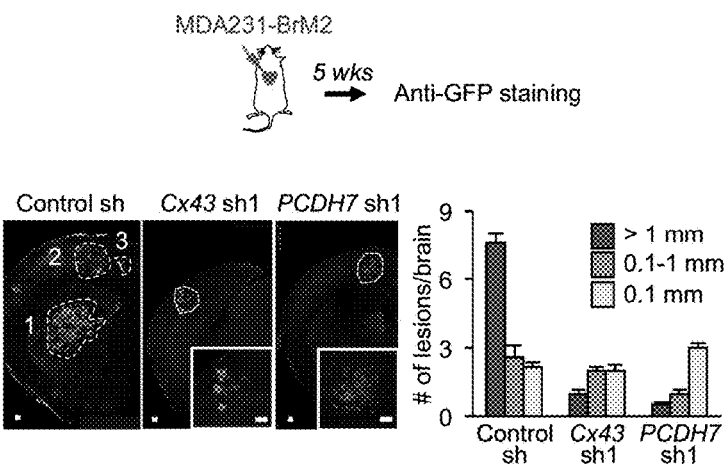
Figure 10C:
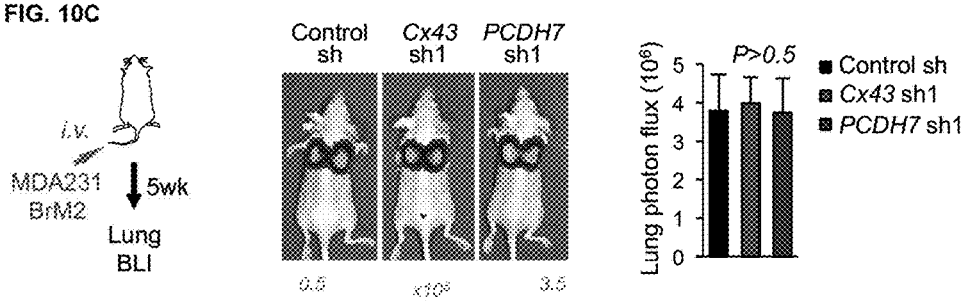

Cx43 and PCDH7 Mediate Brain Metastatic Colonization.

shRNA-mediated depletion of either Cx43 or PCDH7 inhibited formation of brain metastases by breast cancer and lung cancer cells in xenograft (FIG. 2c-d) and immunocompetent models (FIG. 10a). Immunohistologic staining for GFP in brain sections confirmed this result and demonstrated a marked reduction in lesion size as a result of Cx43 or PCDH7 depletion (FIG. 10b). Depletion of Cx43 or PCDH7 did not affect the formation of lung lesions by MDA231-BrM2 cells after tail vein injection (FIG. 10c).

Figure 10D:
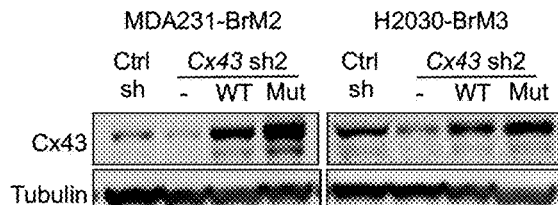
Figure 10E:
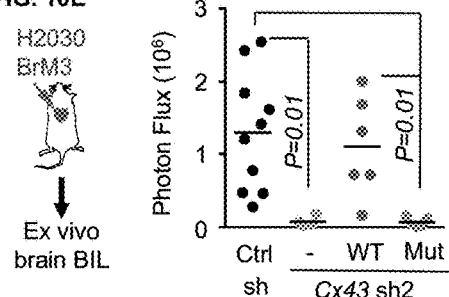

Because connexins may mediate cell-cell interactions independently of channel function, we employed the Cx43 (T154A) mutant that lacks channel function but still assembles hemichannels (FIG. 2e) (Beahm, Oshima et al. 2006). Cx43, either wild type or T154A mutant, was re-expressed in Cx43-depleted brain metastatic cancer cells (FIG. 10d). The mutant Cx43 was unable to mediate calcein transfer from astrocyte to MDA231-BrM cells (FIG. 2e). Wild-type Cx43 rescued brain metastatic activity in Cx43-depleted MDA231-BrM and H2030-BrM cells, whereas Cx43(T154A) did not (FIG. 2f, FIG. 10e). Together, these observations support a model in which PCDH7 directly and specifically interacts with Cx43 to selectively promote functional gap junction formation between cancer cells and astrocytes (FIG. 2g).

Figure 11A:
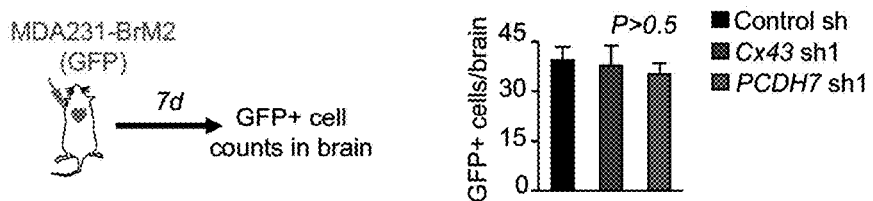
Figure 11B:
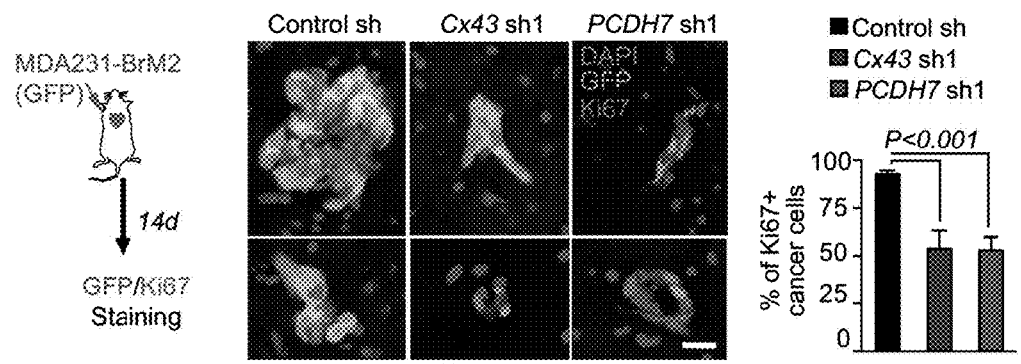
Figure 11C:
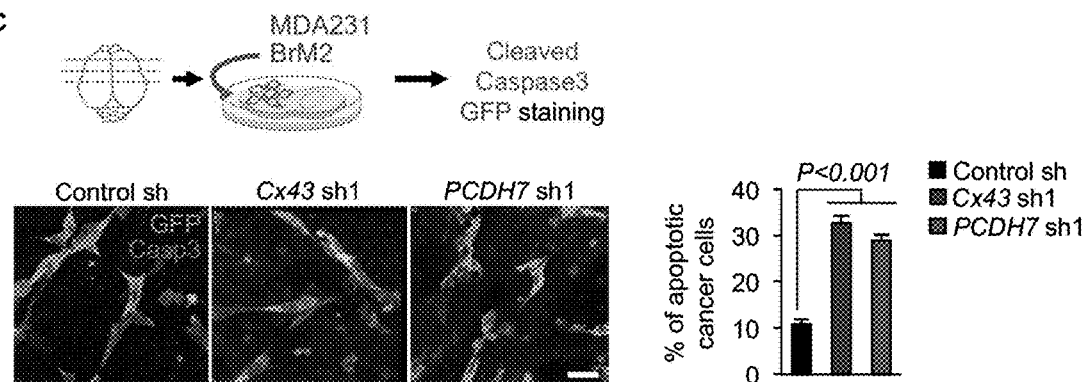
Figure 11D:
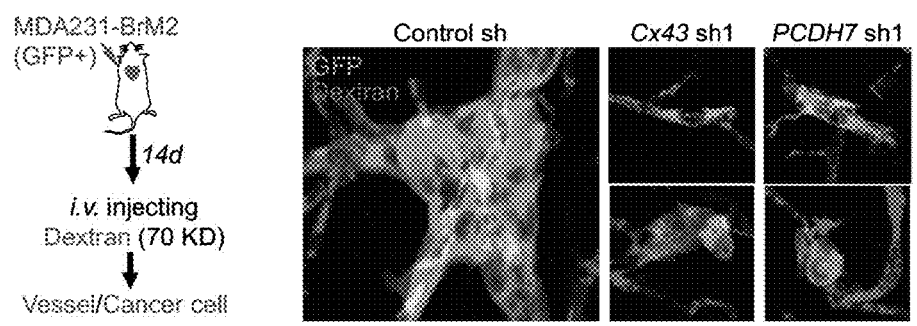

To define the stage at which PCDH7 and Cx43 contribute to the formation of brain metastases, we performed short-term metastasis assays with MDA231-BrM2 cells. In this model, extravasation across the BBB is complete 7 days post-inoculation, vascular cooption and overt outgrowth occur by day 14 (Valiente, Obenauf et al. 2014). Cx43 or PCDH7 depletion in the cancer cells did not significantly diminish the number of GFP+ cancer cells in the brain parenchyma 7 days after inoculation (FIG. 11a). Fourteen days after inoculation, micrometastases resulting from Cx43 or PCDH7 depleted cells showed decreased proliferation, as determined by Ki67 staining (FIG. 11b). Apoptosis of brain metastatic cells was determined in the ex-vivo brain slice assay (Valiente, Obenauf et al. 2014). With this approach, we found increased caspase 3 staining in Cx43 or PCDH7-depleted cells, consistent with increased apoptosis. (FIG. 11c). Of note, the Cx43-depleted or PCDH7-depleted cells were still able to closely interact with capillaries (FIG. 11d). Thus, cancer cell-astrocyte gap junctions support brain metastasis development after initial extravasation and vascular cooption.

Cancer Cells Gap Junctions Trigger Astrocyte Cytokine Release.

Figure 12A:
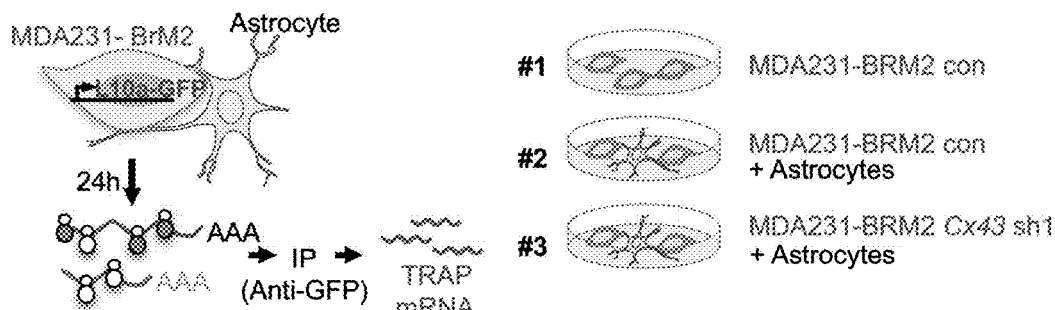
Figure 12B:
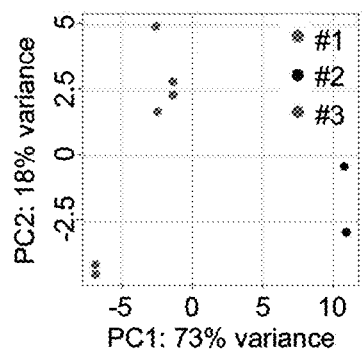
Figure 12C:
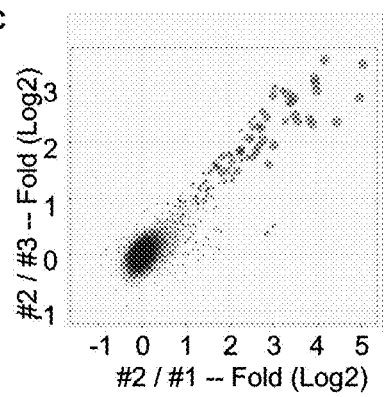
Figure 12D:
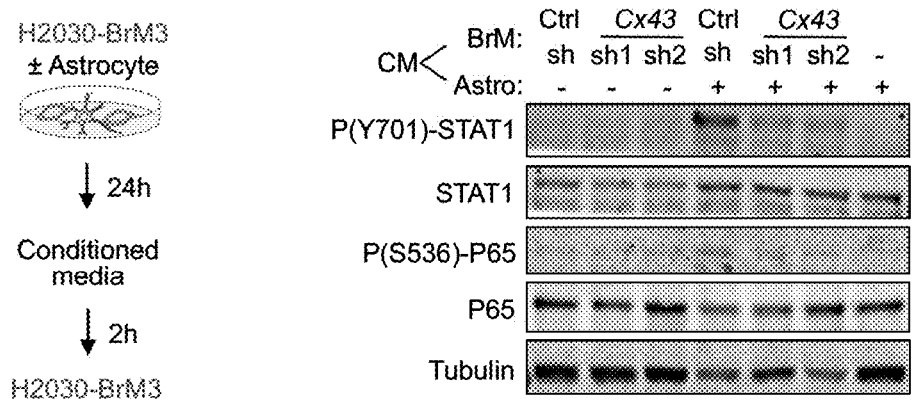

To determine the mechanism behind this Cx43-mediated brain metastatic growth, we employed translating ribosome affinity purification (TRAP) (Heiman, Schaefer et al. 2008) to assay cancer cell gene expression in mixed co-cultures (FIG. 12a). We expressed the eGFP-tagged L10a ribosomal subunit in MDA231-BrM2 cells with either basal or reduced Cx43 expression. After cancer cell co-culture with astrocytes for 24 h, eGFP immunoprecipitation and polysome-associated mRNA harvest from cancer cells was followed by global transcriptome sequencing (TRAP-RNAseq) (FIG. 12b.c). Gene signature analysis revealed that the interferon (IFN) and NF-κB pathways were the most activated pathways in brain metastatic cells after co-culture with astrocytes, and these effects required Cx43 (FIG. 3a). Other upregulated pathways included Her2/AKT and TGFβ. Conditioned media from astrocyte-MDA231-BrM2 cells was sufficient to activate the IFN and NF-κB signaling in the cancer cells, as determined by increased phosphorylation of STAT1 and NF-κB p65 (FIG. 3b, FIG. 12d). This effect was not observed with conditioned media from astrocyte co-cultures with Cx43-depleted or Cx43(T154A) reconstituted cancer cells (FIG. 3c).

Analysis of conditioned media generated in MDA231-BrM2-astrocyte co-cultures (FIG. 3d) demonstrated accumulation of type I interferon, IFNα, and TNFα in a gap-junction dependent manner (FIG. 3e, FIG. 13a-b); no type II interferon, IFNγ, was detected (data not shown). MDA231-BrM2, either alone or co-cultured with astrocytes, did not express these cytokines as detected by TRAP-RNAseq (data not shown). Upregulation of INFα and TNFα mRNA was detected in the astrocytes reisolated after the co-culture (FIG. 3f). These results suggested that the heterocellular gap junction communication elicited production of IFNα and TNFα in astrocytes, triggering STAT1 and NF-κB pathway activation in the cancer cells.

Addition of IFNα and TNFα inhibited the apoptotic response of brain metastatic cancer cells to cytotoxic chemotherapy in vitro (FIG. 3g, FIG. 13c). To assess the functional importance of these pathways in brain metastasis, we knocked down STAT1 by shRNAs (FIG. 3h, FIG. 13d) or inhibited NF-κB by overexpression of IκBα super suppressor (SR-IκBα) (Boehm, Zhao et al. 2007) (FIG. 3i) in brain metastatic cells. When inoculated into mice, these cells produced smaller brain metastases than control counterparts (FIG. 3j, FIG. 13e), suggesting that STAT1 and NF-κB activators provide a survival advantage for metastatic cells in the brain.

Cancer Cell Gap Junctions Activate the Cytosolic dsDNA Response in Astrocytes.

Whereas IFNα and TNFα may be individually induced by diverse inputs, the joint upregulation of both cytokines was reminiscent of a cellular response to cytosolic double stranded DNA (dsDNA) (Cai, Chiu et al. 2014). Cytosolic dsDNA triggers the cGAS-STING pathway, in which cyclic GMP-AMP synthase (cGAS) senses cytosolic dsDNA and synthesizes the second messenger 2'3'-cyclic GMP-AMP (cGAMP). cGAMP binding to STING triggers phosphorylation and activation of TBK1 and IRF3, nuclear accumulation of IRF3, and transcriptional activation of IRF3 target genes IFNA and TNFA (Wu, Sun et al. 2013). This pathway represents an ancient anti-viral innate immune response (Cai, Chiu et al. 2014).

Figure 14A:
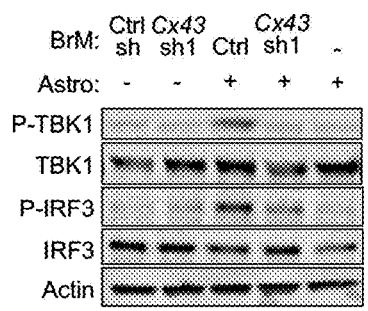
Figure 14B:
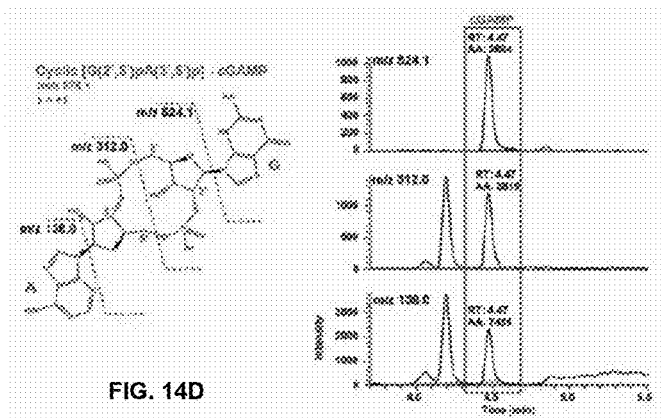

Co-incubation of MDA231-BrM2 cells and astrocytes triggered phosphorylation of TBK1 and IRF3 in a Cx43-dependent manner (FIG. 4a, FIG. 14a). Nuclear accumulation of IRF3 occurred only in the astrocytes in co-cultures, and not in astrocytes or cancer cells cultured alone (FIG. 4b). Using LC-MS/MS, we detected cGAMP in MDA231-BrM2 cells but not in astrocytes cultured alone (FIG. 4c-d, FIG. 14b). Co-culture of a fixed number of MDA231-BrM2 cells with astrocytes led to a Cx43-dependent increase in the levels of cGAMP (FIG. 4c-d). Using stress conditions that release mitochondrial dsDNA into the cytosol, we confirmed that astrocytes are competent to produce cGAMP in response to cytosolic dsDNA (Rongvaux, Jackson et al. 2014).

Figure 14C:
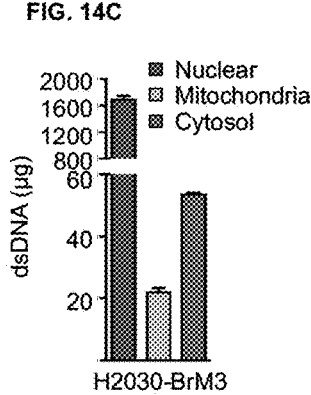
Figure 14D:
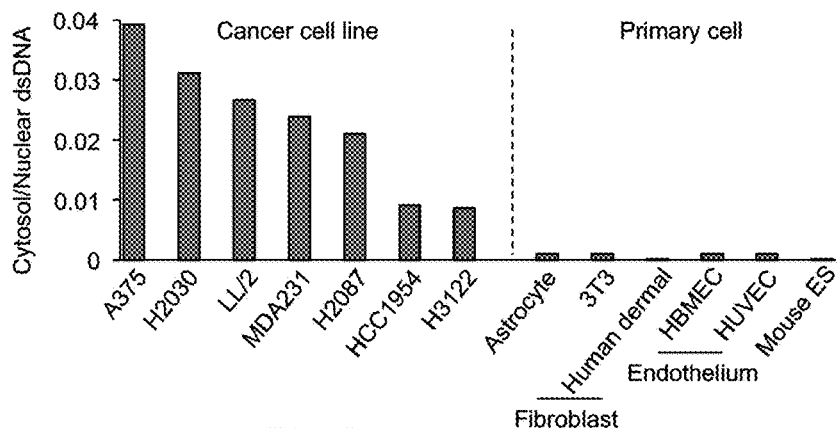
Figure 14E:
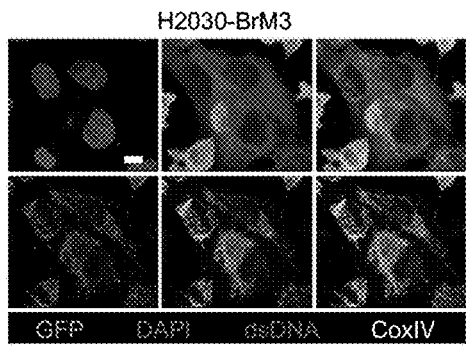
Figure 14F:
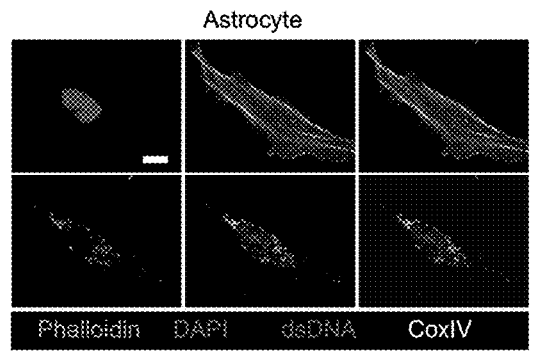
Figure 14G:
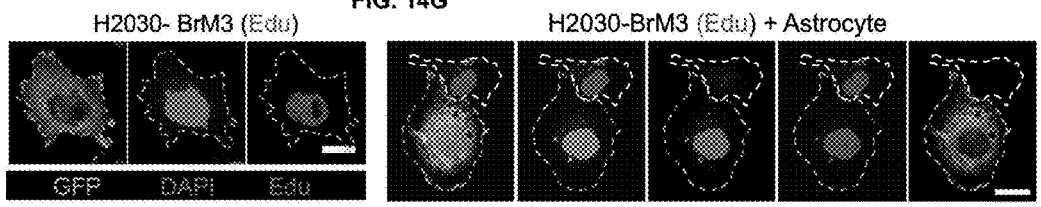

Subcellular fractionation demonstrated that these brain metastatic cells and other human cancer cell lines contain cytosolic dsDNA whereas astrocytes and other non-neoplastic human cells do not (FIG. 4e, FIG. 14c,d). By immunofluorescence, we detected cytosolic dsDNA in brain metastatic cancer cells (FIG. 4f, FIG. 9e), but not in astrocytes (FIG. 14f). To determine if cancer cell DNA passes to astrocytes through Cx43 gap junctions, we labeled cancer cell DNA with 5-ethynyl-2'-deoxyuridine (EdU), co-cultured the cells with astrocytes and analyzed the distribution of labeled DNA by microscopy (FIG. 4g, FIG. 14g) or flow cytometry (FIG. 4h). Both methods demonstrated transfer of DNA from the cancer cell to the astrocyte in a Cx43-dependent manner.

Taken together, these results support a model in which brain metastatic cancer cells contain cytosolic dsDNA and cGAMP, and employ PCDH7 to engage astrocytes in Cx43-based gap junctions. The gap junctions allow passage of cytosolic dsDNA (and cGAMP) from cancer cells into astrocytes to trigger the generation of additional cGAMP, TBK1 and IRF3 activation, and production of IFNα and TNFα. Acting as paracrine factors, these cytokines activate STAT1 and NF-κB signaling in the cancer cells, which support the growth and survival of the cancer cells in the face of microenvironmental and chemotherapeutic stresses (FIG. 4i).

Pharmacologic Inhibition of Gap Junction Activity.

The evidence that genetic inhibition of gap junction components decreased brain metastatic outgrowth provided a rationale for testing pharmacologic suppressors of gap junction activity against brain metastasis. To this end, we selected two orally bioavailable compounds for pre-clinical trials. In addition to anti-inflammatory activity, meclofenamate inhibits Cx43 gap junction gating (Harks, de Roos et al. 2001), inhibits epileptogenesis in animal models (Jin, Dai et al. 2013), passes the BBB after systemic administration (Harks, de Roos et al. 2001), is well tolerated systemically (Holmes 1966) and is currently an FDA-approved NSAID. Tonabersat is an benzopyran derivative that binds to a unique stereoselective binding site in astrocytes (Herdon, Jerman et al. 1997, Chan, Evans et al. 1999), inhibits gap-junction-mediated pathophysiological processes including cortical spreading depression (Read, Smith et al. 2000) and trigeminal ganglion neuronal-satellite cell signaling in animal models (Damodaram, Thalakoti et al. 2009), and was systemically well-tolerated and safe in patients with migraine (Dahlof, Hauge et al. 2009).

Figure 15A:
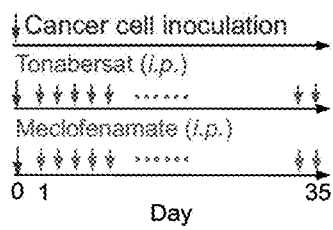
Figure 15B:
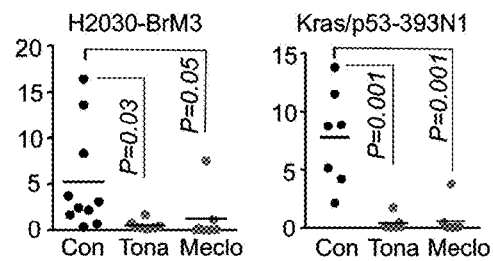
Figure 15C:
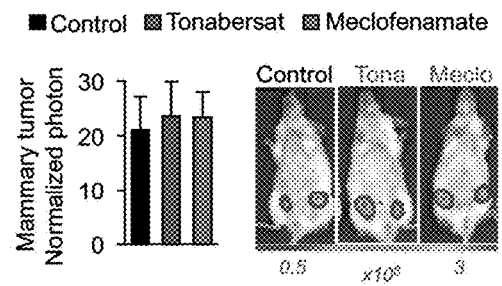
Figure 15D:
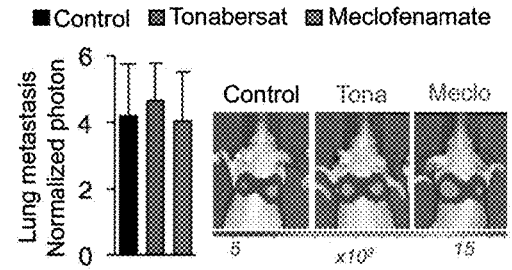
Figure 15E:
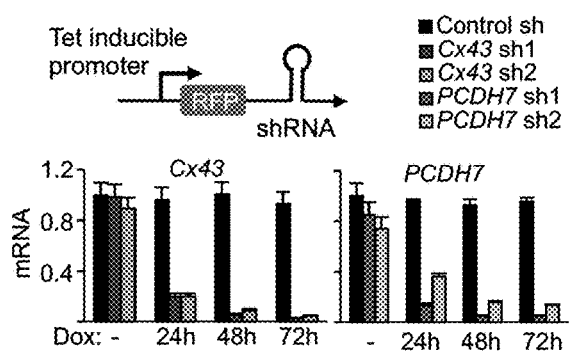

Both Tonabersat and meclofenamate inhibited dye transfer from astrocytes to cancer cells as measured by flow cytometry (FIG. 5a), and the release of IFNα and TNFα in co-cultures of these cells (FIG. 5b), recapitulating the phenotype seen in knockdown of Cx43 or PCDH7. Mice were treated with either vehicle or with these compounds from day 1 following arterial inoculation of MDA231-BrM2 cells or H2030-BrM3 cells in immunodeficient mice, or KRas/p53-393N1 cells in immunocompetent mice (FIG. 5c, FIG. 15a,b). Both drugs prevented the emergence of brain metastases, consistent with our evidence that gap junction activity is relevant for metastatic outgrowth. However, this treatment did not restrict growth of MDA231-BrM2 cells as lung metastatic lesions or as orthotopic tumours (FIG. 15c, d).

Gap Junction Directed Therapy.

Figure 15F:
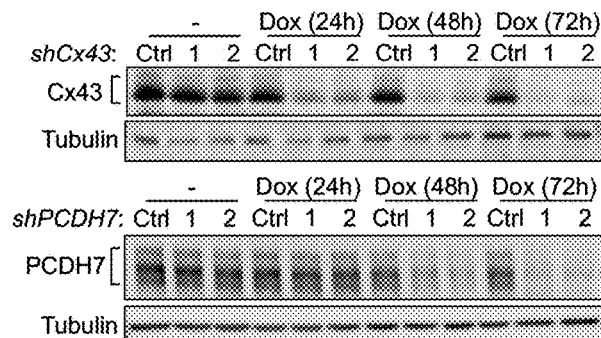
Figure 15G:

To test the effect of Cx43 or PCDH7 depletion in established metastases, we transduced MDA231-BrM2 cells with Tet-inducible shRNA expression vectors (FIG. 5e). A red fluorescence protein (RFP) under the control of the same promoter provided a marker of hairpin expression in vivo (FIG. 10e). Cells transduced with inducible Cx43 or PCDH7 shRNA vectors showed doxycycline-dependent depletion of Cx43 or PCDH7, respectively (FIG. 15f). These cells were injected intracardially and allowed to form brain metastases for 14 days. At this stage, brain lesions are apparent by BLI in all mice (FIG. 15g); the aggressive lesions engulf the microvasculature (FIG. 5d) and will result in death of the animals in 2-3 weeks (Bos, Zhang et al. 2009, Valiente, Obenauf et al. 2014). Doxycycline administration starting on day 14 resulted in reduced brain metastatic burden three weeks later, compared to controls (FIG. 5f,g).

Brain metastases are distinguished by pronounced resistance to chemotherapy (Zhang, Price et al. 1992, Deeken and Loscher 2007). Carboplatin crosses the BBB (Pitz, Desai et al. 2011), with modest improvement in overall survival in patients with brain metastases from breast (Lim and Lin 2014) or lung cancer (Taimur and Edelman 2003). Carboplatin alone (50 mg/kg/5 days) starting on day 14 inhibited brain metastasis to a similar extent as depletion of Cx43 or PCDH7 (FIG. 5f,g); combination carboplatin and doxycycline reduced the metastatic burden further (FIG. 5f,g). Therefore, we assessed the effectiveness of combination gap junction modulatory therapy with chemotherapy (FIG. 5h). Treatment with carboplatin alone minimally inhibited brain metastasis growth (FIG. 5i). Either Tonabersat (10 mg/kg) or meclofenamate (20 mg/kg) as single agents (FIG. 5i) significantly inhibited progression of metastatic lesions at the 35-day end point. The combination of carboplatin with either Tonabersat or meclofenamate profoundly inhibited brain metastasis (FIG. 5i).

6.3 Discussion

The brain represents a unique and formidable metastatic target, with astrocytes a predominant feature of the microenvironment. We present evidence that cancer cells employ PCDH7 to selectively engage astrocytes in vital Cx43 gap junctions. Cadherin family members are important mediators of cell-cell communication in development and tissue homeostasis (Yagi and Takeichi 2000), particularly in the nervous system (Hirano, Suzuki et al. 2003). It is remarkable that brain metastatic cells adopt a particular member of this family whose normal expression is largely restricted to the brain (Yoshida, Yoshitomo-Nakagawa et al. 1998). PCDH7 therefore joins ST6GALNAC5 (Bos, Zhang et al. 2009), and neuroserpin (Valiente, Obenauf et al. 2014) as brain-restricted components that brain metastatic cells from breast and lung carcinomas selectively express to colonize the brain.

PCDH7 and Cx43 contribute to brain metastatic colonization and chemoresistance. Functional Cx43-based gap junctions between cancer cells and astrocytes allow cancer cells to disseminate cytosolic dsDNA to the astrocyte network. This activates the astrocytic cGAS-STING pathway, culminating in release of cytokines including IFNα and TNFα. These cytokines provide a growth advantage for brain metastatic cells by protecting against physiologic and chemotherapeutic stressors. Other upregulated pathways include Her2/AKT and TGFβ. Our results therefore provide in vivo evidence and mechanistic underpinnings for a previously observed chemoprotective effect of astrocytes on cancer cells in vitro (Kim, Kim et al. 2011). The present evidence together with previous work suggests that cancer cells protect themselves from astrocytic attack in two ways, first, through production of serpin inhibitors of cytotoxic plasmin generation, and second, by engaging astrocytes through gap junctions and appropriating the dsDNA response.

Cytosolic dsDNA was first defined as an activator of innate immunity against viral infection (Stetson and Medzhitov 2006). In cancer cells, there are a number of possible sources of dsDNA including genomic instability, mitochondrial stress, and exposure to DNA-damaging agents. DNA-triggered innate immune responses and, specifically, cGAMP, can pass to other cells through gap junctions (Patel, King et al. 2009, Ablasser, Schmid-Burgk et al. 2013). Fitting with these observations, we find that malignant cells, including brain metastatic derivatives, contain high levels of cytosolic dsDNA and cGAMP compared with astrocytes and other stromal cells. Importantly, in brain metastasis the dsDNA response emerges from intrinsic cytosolic dsDNA in the cancer cells, is Cx43-dependent, and involves host tissue astrocytes, thus representing an unprecedented pro-metastatic process.

Brain metastases are a major contributor to cancer patient morbidity and mortality, with few therapeutic options available. Early steps in the brain metastatic cascade, including cancer cell dissemination and extravasation through the BBB, have not been amenable to therapy (Maher, Mietz et al. 2009, Eichler, Chung et al. 2011). However, cancer cell dependency on Cx43/PCDH7 gap junctions for survival and outgrowth of metastatic lesions suggests a therapeutic opportunity. Our pre-clinical results using combinations of chemotherapy and gap junction modulators provide proof-of-principle for the therapeutic potential of these interventions against brain metastasis.

TABLE 1

Target Sequences of shRNAs (SEQ ID NOS: 1-14, top to bottom)

| PLKO.1 lenivirus vectors-human genes | | |
|---|---|---|
| Name of sh | Catalog number | Sequence |
| Cx43 sh1 | TRCN0000059773 | GCCCAAACTGATGGTGTCAAT |
| Cx43 sh2 | TRCN0000059775 | GCGACAGAAACAATTCTTCTT |
| PCDH7 sh1 | TRCN0000055744 | GCAGGAGACAACATTTCAAT |
| PCDH7 sh2 | TRCN0000291663 | GCTGGCATTATGACGGTGATT |
| STAT1 sh1 | TRCN0000280021 | CTGGAAGATTTACAAGATGAA |
| STAT1 sh2 | TRCN0000004265 | CCCTGAAGTATCTGTATCCAA |
| TRIPZ inducible lenivirus vectors-human genes | | |
| Name of sh | Catalog number | Sequence |
| Cx43 sh1 | V3THS_411733 | TAAGGACAATCCTCTGTCT |
| Cx43 sh2 | V3THS_411729 | TGAGTGGAATCTTGATGCT |
| PCDH7 sh1 | V3THS_338930 | GAATCAACACTGCCATCCG |
| PCDH7 sh2 | V3THS_152694 | TTAAGATGATTAGAATCAC |

TABLE 1-continued

Target Sequences of shRNAs (SEQ ID NOS: 1-14, top to bottom)

GIPZ lenivirus vectors-mouse genes

| Name of sh | Catalog number | Sequence |
|---|---|---|
| Cx43 sh1 | V3LHS_411730 | TGAGTACCACCTCCACCGG |
| PCDH7 sh1 | V3LMM_510718 | TAACTTTAAACTCATACCT |
| PCDH7 sh2 | V2LMM_11270 | TAAACTTAGGGTCGTTGTC |

Control sh

| Name of sh | | |
|---|---|---|
| Ctrl sh | SHC016 | CCGGGCGCGATAGCGCTAAT AATTTCTC |

TABLE 2

Antibodies

| Antibody against | Company | Catalog number |
|---|---|---|
| Western blotting antibodies | | |
| Cx43 | Cell Signaling | 3512 |
| PCDH7 | Sigma-Aldrich | HPA011866 |
| α-tubulin | Sigma-Aldrich | T6074 |
| E-cadherin | Cell Signaling | 3195 |
| N-cadherin | Sigma-Aldrich | C3865 |
| Phospho-STAT1 | Cell Signaling | 9167 |
| STAT1 | Cell Signaling | 9172 |
| Phospho-NF-κBp65 | Cell Signaling | 3033 |
| NF-κB p65 | Cell Signaling | 8242 |
| Phospho-TBK1 | Cell Signaling | 5483 |
| TBK1 | Cell Signaling | 3013 |
| Phospho-IRF3 | Cell Signaling | 4947 |
| IRF3 | Cell Signaling | 11904 |
| IκBα | Cell Signaling | 4812 |
| Immunochemical staining antibodies | | |
| Cx43 | Cell Signaling | 3512 |
| GFP | Aves Labs | GFP-1020 |
| Ki67 | Vector Laboratories | VP-K451 |
| GFAP | Dako | Z0334 |
| GFAP | EMD Millipore | MAB360 |
| CollagenIV | EMD Millipore | AB756P |
| IRF3 | Cell Signaling | 9172 |
| dsDNA | EMD Millipore | MAB1293 |
| CoxIV | Cell Signaling | 4850 |

7. REFERENCES

Axelsen, L. N., Calloe, K., Holstein-Rathlou, N. H., and Nielsen, M. S. (2013). Managing the complexity of communication: regulation of gap junctions by post-translational modification. Front Pharmacol 4, 130.

Bartzatt, R. (2012). Anti-inflammatory drugs and prediction of new structures by comparative analysis. Antiinflamm Antiallergy Agents Med Chem 11, 151-160.

Bennett, M. V., and Goodenough, D. A. (1978). Gap junctions, electrotonic coupling, and intercellular communication. Neurosci Res Program Bull 16, 1-486.

Bos, P. D., Zhang, X. H., Nadal, C., Shu, W., Gomis, R. R., Nguyen, D. X., Minn, A. J., van deVijver, M. J., Gerald, W. L., Foekens, J. A., et al. (2009). Genes that mediate breast cancer metastasis to the brain. Nature 459, 1005-1009.

Bradley, D. P., Smith, M. I., Netsiri, C., Smith, J. M., Bockhorst, K. H., Hall, L. D., Huang, C. L., Leslie, R. A., Parsons, A. A., and James, M. F. (2001). Diffusion-weighted MRI used to detect in vivo modulation of cortical spreading depression: comparison of sumatriptan and tonabersat. Exp Neurol 172, 342-353.

Chambers, A. F., Groom, A. C., and MacDonald, I. C. (2002). Dissemination and growth of cancer cells in metastatic sites. Nat Rev Cancer 2, 563-572.

Chan, W. N., Evans, J. M., Hadley, M. S., Herdon, H. J., Jerman, J. C., Parsons, A. A., Read, S. J., Stean, T. O., Thompson, M., and Upton, N. (1999). Identification of (−)-cis-6-acetyl-4S-(3-chloro-4-fluoro-benzoylamino)-3,4-dihydro-2,2-dimethyl-2H-benzo[b]pyran-3S-ol as a potential antimigraine agent. Bioorg Med Chem Lett 9, 285-290.

Dahlof, C. G., Hauge, A. W., and Olesen, J. (2009). Efficacy and safety of tonabersat, a gap junction modulator, in the acute treatment of migraine: a double-blind, parallel-group, randomized study. Cephalalgia 29 Suppl 2, 7-16.

Damodaram, S., Thalakoti, S., Freeman, S. E., Garrett, F. G., and Durham, P. L. (2009). Tonabersat inhibits trigeminal ganglion neuronal-satellite glial cell signaling. Headache 49, 5-20.

DeAngelis, L. M., and Posner, J. B. (2009). Intracranial Metastasis. In Neurologic Complications of Cancer, S. Gilman, ed. (Oxford University Press), pp. 141-274.

Deeken, J. F., and Loscher, W. (2007). The blood-brain barrier and cancer: transporters, treatment, and Trojan horses. Clin Cancer Res 13, 1663-1674.

Eichler, A. F., Chung, E., Kodack, D. P., Loeffler, J. S., Fukumura, D., and Jain, R. K. (2011). The biology of brain metastases-translation to new therapies. Nat Rev Clin Oncol 8, 344-356.

Eugenin, E. A., Basilio, D., Saez, J. C., Orellana, J. A., Raine, C. S., Bukauskas, F., Bennett, M. V., and Berman, J. W. (2012). The role of gap junction channels during physiologic and pathologic conditions of the human central nervous system. J Neuroimmune Pharmacol 7, 499-518.

Gaspar, L. E., Gay, E. G., Crawford, J., Putnam, J. B., Herbst, R. S., and Bonner, J. A. (2005). Limited-stage small-cell lung cancer (stages I-III): observations from the National Cancer Data Base. Clin Lung Cancer 6, 355-360.

Gaspar, L. E., Scott, C., Murray, K., and Curran, W. (2000). Validation of the RTOG recursive partitioning analysis (RPA) classification for brain metastases. Int J Radiat Oncol Biol Phys 47, 1001-1006.

Gavrilovic, I. T., and Posner, J. B. (2005). Brain metastases: epidemiology and pathophysiology. J Neurooncol 75, 5-14.

Gilula, N. B., Reeves, O. R., and Steinbach, A. (1972). Metabolic coupling, ionic coupling and cell contacts. Nature 235, 262-265.

Goadsby, P. J., Ferrari, M. D., Csanyi, A., Olesen, J., Mills, J. G., and Tonabersat, T. O. N. S. G. (2009). Randomized, double-blind, placebo-controlled, proof-of-concept study of the cortical spreading depression inhibiting agent tonabersat in migraine prophylaxis. Cephalalgia 29, 742-750.

Goldberg, G. S., Lampe, P. D., and Nicholson, B. J. (1999). Selective transfer of endogenous metabolites through gap junctions composed of different connexins. Nat Cell Biol 1, 457-459.

Gupta, G. P., Nguyen, D. X., Chiang, A. C., Bos, P. D., Kim, J. Y., Nadal, C., Gomis, R. R., Manova-Todorova, K., and Massague, J. (2007). Mediators of vascular remodelling co-opted for sequential steps in lung metastasis. Nature 446, 765-770.

Harks, E. G., de Roos, A. D., Peters, P. H., de Haan, L. H., Brouwer, A., Ypey, D. L., van Zoelen, E. J., and Theuvenet, A. P. (2001). Fenamates: a novel class of reversible gap junction blockers. J Pharmacol Exp Ther 298, 1033-1041.

Herdon, H. J., Jerman, J. C., Stean, T. O., Middlemiss, D. N., Chan, W. N., Vong, A. K., Evans, J. M., Thompson, M., and Upton, N. (1997). Characterization of the binding of [3H]-SB-204269, a radiolabelled form of the new anticonvulsant SB-204269, to a novel binding site in rat brain membranes. Br J Pharmacol 121, 1687-1691.

Heyn, C., Ronald, J. A., Ramadan, S. S., Snir, J. A., Barry, A. M., MacKenzie, L. T., Mikulis, D. J., Palmieri, D., Bronder, J. L., Steeg, P. S., et al. (2006). In vivo MRI of cancer cell fate at the single-cell level in a mouse model of breast cancer metastasis to the brain. Magn Reson Med 56, 1001-1010.

Hirano, S., Suzuki, S. T., and Redies, C. (2003). The cadherin superfamily in neural development: diversity, function and interaction with other molecules. Front Biosci 8, d306-355.

Holder, J. W., Elmore, E., and Barrett, J. C. (1993). Gap junction function and cancer. Cancer Res 53, 3475-3485.

Holmes, E. L. (1966). Experimental observations on flufenamic, mefenamic, and meclofenamic acids. IV. Toleration by normal human subjects. Ann Phys Med Suppl, 36-49.

Hsu, M., Andl, T., Li, G., Meinkoth, J. L., and Herlyn, M. (2000). Cadherin repertoire determines partner-specific gap junctional communication during melanoma progression. J Cell Sci 113 (Pt 9), 1535-1542.

Jin, M., Dai, Y., Xu, C., Wang, Y., Wang, S., and Chen, Z. (2013). Effects of meclofenamic acid on limbic epileptogenesis in mice kindling models. Neurosci Lett 543, 110-114.

Joyce, J. A., and Pollard, J. W. (2009). Microenvironmental regulation of metastasis. Nat Rev Cancer 9, 239-252.

Juszczak, G. R., and Swiergiel, A. H. (2009). Properties of gap junction blockers and their behavioural, cognitive and electrophysiological effects: animal and human studies. Prog Neuropsychopharmacol Biol Psychiatry 33, 181-198.

Juul, M. H., Rivedal, E., Stokke, T., and Sanner, T. (2000). Quantitative determination of gap junction intercellular communication using flow cytometric measurement of fluorescent dye transfer. Cell Adhes Commun 7, 501-512.

Kienast, Y., von Baumgarten, L., Fuhrmann, M., Klinkert, W. E., Goldbrunner, R., Herms, J., and Winkler, F. (2010). Real-time imaging reveals the single steps of brain metastasis formation. Nat Med 16, 116-122.

Kim, S. J., Kim, J. S., Park, E. S., Lee, J. S., Lin, Q., Langley, R. R., Maya, M., He, J., Kim, S. W., Weihua, Z., et al. (2011). Astrocytes upregulate survival genes in tumor cells and induce protection from chemotherapy. Neoplasia 13, 286-298.

Kim, S. Y., Chung, H. S., Sun, W., and Kim, H. (2007). Spatiotemporal expression pattern of nonclustered protocadherin family members in the developing rat brain. Neuroscience 147, 996-1021.

Li, B., Wang, C., Zhang, Y., Zhao, X. Y., Huang, B., Wu, P. F., Li, Q., Li, H., Liu, Y. S., Cao, L. Y., et al. (2013). Elevated PLGF contributes to small-cell lung cancer brain metastasis. Oncogene 32, 2952-2962.

Lim, E., and Lin, N. U. (2014). Updates on the Management of Breast Cancer Brain Metastases. Oncology (Williston Park) 28(7).

Lorger, M., and Felding-Habermann, B. (2010). Capturing changes in the brain microenvironment during initial steps of breast cancer brain metastasis. Am J Pathol 176, 2958-2971.

Loscher, W., and Potschka, H. (2005). Drug resistance in brain diseases and the role of drug efflux transporters. Nat Rev Neurosci 6, 591-602.

Luker, K. E., Smith, M. C., Luker, G. D., Gammon, S. T., Piwnica-Worms, H., and Piwnica-Worms, D. (2004). Kinetics of regulated protein-protein interactions revealed with firefly luciferase complementation imaging in cells and living animals. Proc Natl Acad Sci USA 101, 12288-12293.

MaassenVanDenBrink, A., van den Broek, R. W., de Vries, R., Upton, N., Parsons, A. A., and Saxena, P. R. (2000). The potential anti-migraine compound SB-220453 does not contract human isolated blood vessels or myocardium; a comparison with sumatriptan. Cephalalgia 20, 538-545.

Maher, E. A., Mietz, J., Arteaga, C. L., DePinho, R. A., and Mohla, S. (2009). Brain metastasis: opportunities in basic and translational research. Cancer Res 69, 6015-6020.

Miyamoto, S., Yagi, H., Yotsumoto, F., Kawarabayashi, T., and Mekada, E. (2006). Heparin binding epidermal growth factor-like growth factor as a novel targeting molecule for cancer therapy. Cancer Sci 97, 341-347.

Nguyen, D. X., Chiang, A. C., Zhang, X. H., Kim, J. Y., Kris, M. G., Ladanyi, M., Gerald, W. L., and Massague, J. (2009). WNT/TCF signaling through LEF1 and HOXB9 mediates lung adenocarcinoma metastasis. Cell 138, 51-62.

Nilsen, K. E., Kelso, A. R., and Cock, H. R. (2006). Antiepileptic effect of gap-junction blockers in a rat model of refractory focal cortical epilepsy. Epilepsia 47, 1169-1175.

Noy, R., and Pollard, J. W. (2014). Tumor-associated macrophages: from mechanisms to therapy. Immunity 41, 49-61.

Oberheim, N. A., Goldman, S. A., and Nedergaard, M. (2012). Heterogeneity of astrocytic form and function. Methods Mol Biol 814, 23-45.

Oshima, A. (2014). Structure and closure of connexin gap junction channels. FEBS Lett 588, 1230-1237.

Pekny, M., and Nilsson, M. (2005). Astrocyte activation and reactive gliosis. Glia 50, 427-434.

Pitz, M. W., Desai, A., Grossman, S. A., and Blakeley, J. O. (2011). Tissue concentration of systemically administered antineoplastic agents in human brain tumors. J Neurooncol 104, 629-638.

Read, S. J., Hirst, W. D., Upton, N., and Parsons, A. A. (2001). Cortical spreading depression produces increased cGMP levels in cortex and brain stem that is inhibited by tonabersat (SB-220453) but not sumatriptan. Brain Res 891, 69-77.

Read, S. J., Smith, M. I., Hunter, A. J., Upton, N., and Parsons, A. A. (2000). SB-220453, a potential novel antimigraine agent, inhibits nitric oxide release following induction of cortical spreading depression in the anaesthetized cat. Cephalalgia 20, 92-99.

Sarrouilhe, D., Dejean, C., and Mesnil, M. (2014). Involvement of gap junction channels in the pathophysiology of migraine with aura. Front Physiol 5, 78.

Silberstein, S. D., Schoenen, J., Gobel, H., Diener, H. C., Elkind, A. H., Klapper, J. A., and Howard, R. A. (2009). Tonabersat, a gap-junction modulator: efficacy and safety in two randomized, placebo-controlled, dose-ranging studies of acute migraine. Cephalalgia 29 Suppl 2, 17-27.

Smith, M. I., Read, S. J., Chan, W. N., Thompson, M., Hunter, A. J., Upton, N., and Parsons, A. A. (2000). Repetitive cortical spreading depression in a gyrencephalic feline brain: inhibition by the novel benzoylaminobenzopyran SB-220453. Cephalalgia 20, 546-553.

Solan, J. L., and Lampe, P. D. (2009). Connexin43 phosphorylation: structural changes and biological effects. Biochem J 419, 261-272.

Stelzer, K. J. (2013). Epidemiology and prognosis of brain metastases. Surg Neurol Int 4, S 192-202.

Taimur, S., and Edelman, M. J. (2003). Treatment options for brain metastases in patients with non-small-cell lung cancer. Curr Oncol Rep 5, 342-346.

Theis, M., and Giaume, C. (2012). Connexin-based intercellular communication and astrocyte heterogeneity. Brain Res 1487, 88-98.

Upton, N., Blackburn, T. P., Campbell, C. A., Cooper, D., Evans, M. L., Herdon, H. J., King, P. D., Ray, A. M., Stean, T. O., Chan, W. N., et al. (1997). Profile of SB-204269, a mechanistically novel anticonvulsant drug, in rat models of focal and generalized epileptic seizures. Br J Pharmacol 121, 1679-1686.

Valiente, M., Obenauf, A. C., Jin, X., Chen, Q., Zhang, X. H., Lee, D. J., Chaft, J. E., Kris, M. G., Huse, J. T., Brogi, E., et al. (2014). Serpins promote cancer cell survival and vascular co-option in brain metastasis. Cell 156, 1002-1016.

Winslow, M. M., Dayton, T. L., Verhaak, R. G., Kim-Kiselak, C., Snyder, E. L., Feldser, D. M., Hubbard, D. D., DuPage, M. J., Whittaker, C. A., Hoersch, S., et al. (2011). Suppression of lung adenocarcinoma progression by Nkx2-1. Nature 473, 101-104.

Xing, F., Kobayashi, A., Okuda, H., Watabe, M., Pai, S. K., Pandey, P. R., Hirota, S., Wilber, A., Mo, Y. Y., Moore, B. E., et al. (2013). Reactive astrocytes promote the metastatic growth of breast cancer stem-like cells by activating Notch signalling in brain. EMBO Mol Med 5, 384-396.

Yagi, T., and Takeichi, M. (2000). Cadherin superfamily genes: functions, genomic organization, and neurologic diversity. Genes Dev 14, 1169-1180.

Yoshida, K., Yoshitomo-Nakagawa, K., Seki, N., Sasaki, M., and Sugano, S. (1998). Cloning, expression analysis, and chromosomal localization of BH-protocadherin (PCDH7), a novel member of the cadherin superfamily. Genomics 49, 458-461.

Zhang, R. D., Price, J. E., Fujimaki, T., Bucana, C. D., and Fidler, I. J. (1992). Differential permeability of the blood-brain barrier in experimental brain metastases produced by human neoplasms implanted into nude mice. Am J Pathol 141, 1115-1124.

Ablasser, A., J. L. Schmid-Burgk, I. Hemmerling, G. L. Horvath, T. Schmidt, E. Latz and V. Hornung (2013). "Cell intrinsic immunity spreads to bystander cells via the intercellular transfer of cGAMP." *Nature* 503(7477): 530-534.

Anders, S., D. J. McCarthy, Y. Chen, M. Okoniewski, G. K. Smyth, W. Huber and M. D. Robinson (2013). "Count-based differential expression analysis of RNA sequencing data using R and Bioconductor." *Nat Protoc* 8(9): 1765-1786.

Beahm, D. L., A. Oshima, G. M. Gaietta, G. M. Hand, A. E. Smock, S. N. Zucker, M. M. Toloue, A. Chandrasekhar, B. J. Nicholson and G. E. Sosinsky (2006). "Mutation of a conserved threonine in the third transmembrane helix of alpha- and beta-connexins creates a dominant-negative closed gap junction channel." *J Biol Chem* 281(12): 7994-8009.

Boehm, J. S., J. J. Zhao, J. Yao, S. Y. Kim, R. Firestein, I. F. Dunn, S. K. Sjostrom, L. A. Garraway, S. Weremowicz, A. L. Richardson, H. Greulich, C. J. Stewart, L. A. Mulvey, R. R. Shen, L. Ambrogio, T. Hirozane-Kishikawa, D. E. Hill, M. Vidal, M. Meyerson, J. K. Grenier, G. Hinkle, D. E. Root, T. M. Roberts, E. S. Lander, K. Polyak and W. C. Hahn (2007). "Integrative genomic approaches identify IKBKE as a breast cancer oncogene." *Cell* 129(6): 1065-1079.

Bos, P. D., D. X. Nguyen and J. Massague (2010). "Modeling metastasis in the mouse." *Curr Opin Pharmacol* 10(5): 571-577.

Cai, J., W. G. Jiang and R. E. Mansel (1998). "Gap junctional communication and the tyrosine phosphorylation of connexin 43 in interaction between breast cancer and endothelial cells." *Int J Mol Med* 1(1): 273-278.

Cai, X., Y. H. Chiu and Z. J. Chen (2014). "The cGAS-cGAMP-STING pathway of cytosolic DNA sensing and signaling." *Mol Cell* 54(2): 289-296.

Gaspar, L. E., K. Chansky, K. S. Albain, E. Vallieres, V. Rusch, J. J. Crowley, R. B. Livingston and D. R. Gandara (2005). "Time from treatment to subsequent diagnosis of brain metastases in stage III non-small-cell lung cancer: a retrospective review by the Southwest Oncology Group." *J Clin Oncol* 23(13): 2955-2961.

Gatza, M. L., J. E. Lucas, W. T. Barry, J. W. Kim, Q. Wang, M. D. Crawford, M. B. Datto, M. Kelley, B. Mathey-Prevot, A. Potti and J. R. Nevins (2010). "A pathway-based classification of human breast cancer." *Proc Natl Acad Sci USA* 107(15): 6994-6999.

Haydon, P. G. and M. Nedergaard (2015). "How do astrocytes participate in neural plasticity?" *Cold Spring Harb Perspect Biol* 7(3): a020438.

Heiman, M., A. Schaefer, S. Gong, J. D. Peterson, M. Day, K. E. Ramsey, M. Suarez-Farinas, C. Schwarz, D. A. Stephan, D. J. Surmeier, P. Greengard and N. Heintz (2008). "A translational profiling approach for the molecular characterization of CNS cell types." *Cell* 135 (4): 738-748.

Kim, D., G. Pertea, C. Trapnell, H. Pimentel, R. Kelley and S. L. Salzberg (2013). "TopHat2: accurate alignment of transcriptomes in the presence of insertions, deletions and gene fusions." *Genome Biol* 14(4): R36.

Love, M. I., W. Huber and S. Anders (2014). "Moderated estimation of fold change and dispersion for RNA-seq data with DESeq2." *Genome Biol* 15(12): 550.

Patel, S. J., K. R. King, M. Casali and M. L. Yarmush (2009). "DNA-triggered innate immune responses are propagated by gap junction communication." *Proc Natl Acad Sci USA* 106(31): 12867-12872.

Pollmann, M. A., Q. Shao, D. W. Laird and M. Sandig (2005). "Connexin 43 mediated gap junctional communication enhances breast tumor cell diapedesis in culture." *Breast Cancer Res* 7(4): R522-534.

Read, S. J., M. I. Smith, A. J. Hunter, N. Upton and A. A. Parsons (2000). "SB-220453, a potential novel antimigraine agent, inhibits nitric oxide release following induction of cortical spreading depression in the anaesthetized cat." Cephalalgia 20(2): 92-99.

Rongvaux, A., R. Jackson, C. C. Harman, T. Li, A. P. West, M. R. de Zoete, Y. Wu, B. Yordy, S. A. Lakhani, C. Y. Kuan, T. Taniguchi, G. S. Shadel, Z. J. Chen, A. Iwasaki and R. A. Flavell (2014). "Apoptotic caspases prevent the induction of type I interferons by mitochondrial DNA." *Cell* 159(7): 1563-1577.

Sharma, V., T. Abraham, A. So, M. F. Allard and J. H. McNeill (2010). "Functional effects of protein kinases and peroxynitrite on cardiac carnitine palmitoyltransferase-1 in isolated mitochondria." *Mol Cell Biochem* 337(1-2): 223-237.

Stetson, D. B. and R. Medzhitov (2006). "Recognition of cytosolic DNA activates an IRF3-dependent innate immune response." *Immunity* 24(1): 93-103.

Stoletov, K., J. Strnadel, E. Zardouzian, M. Momiyama, F. D. Park, J. A. Kelber, D. P. Pizzo, R. Hoffman, S. R. VandenBerg and R. L. Klemke (2013). "Role of connexins in metastatic breast cancer and melanoma brain colonization." *J Cell Sci* 126(Pt 4): 904-913.

Wilson, A. A., L. W. Kwok, E. L. Porter, J. G. Payne, G. S. McElroy, S. J. Ohle, S. R. Greenhill, M. T. Blahna, K. Yamamoto, J. C. Jean, J. P. Mizgerd and D. N. Kotton (2013). "Lentiviral delivery of RNAi for in vivo lineage-specific modulation of gene expression in mouse lung macrophages." *Mol Ther* 21(4): 825-833.

Wu, J., L. Sun, X. Chen, F. Du, H. Shi, C. Chen and Z. J. Chen (2013). "Cyclic GMP-AMP is an endogenous second messenger in innate immune signaling by cytosolic DNA." *Science* 339(6121): 826-830.

Zhang, Q., N. Iwakuma, P. Sharma, B. M. Moudgil, C. Wu, J. McNeill, H. Jiang and S. R. Grobmyer (2009). "Gold nanoparticles as a contrast agent for in vivo tumor imaging with photoacoustic tomography." *Nanotechnology* 20(39): 395102.

Zhang, X. H., X. Jin, S. Malladi, Y. Zou, Y. H. Wen, E. Brogi, M. Smid, J. A. Foekens and J. Massague (2013). "Selection of bone metastasis seeds by mesenchymal signals in the primary tumor stroma." *Cell* 154(5): 1060-1073.

Various references are cited herein, the contents of which are hereby incorporated by reference in their entireties. Various nucleic acid and amino acid sequence accession numbers are cited herein, and the complete sequences referenced by those accession numbers are hereby incorporated by reference in their entireties.

---

What is claimed is:

1. A method for treating a cancer that has metastasized to the brain in a subject, comprising: administering to the subject tonabersat.

2. The method of claim 1, wherein the tonabersat is administered in an amount of about 10 mg/kg.

3. The method of claim 1, wherein the tonabersat is administered in an amount of between about 0.8 mg/kg and about 1.2 mg/kg.

4. The method of claim 1, wherein the cancer is a breast cancer or a lung cancer.

5. The method of claim 1, further comprising administering to the subject an anti-cancer agent.

6. The method of claim 5, wherein the anti-cancer agent is carboplatin.

7. The method of claim 6, wherein the carboplatin is administered in an amount of between 4 mg/kg and about 6 mg/kg.

8. A method for preventing and/or inhibiting the metastasis of a cancer to the brain in a subject, comprising: administering to the subject tonabersat.

9. The method of claim 8, wherein the tonabersat is administered in an amount of about 10 mg/kg.

10. The method of claim 8, wherein the tonabersat is administered in an amount of between about 0.8 mg/kg and about 1.2 mg/kg.

11. The method of claim 8, wherein the cancer is a breast cancer or a lung cancer.

12. The method of claim 8, further comprising administering to the subject an anti-cancer agent.

13. The method of claim 12, wherein the anti-cancer agent is carboplatin.

14. The method of claim 13, wherein the carboplatin is administered in an amount of between 4 mg/kg and about 6 mg/kg.

15. A method for reducing the risk of the metastasis of a cancer to the brain in a subject, comprising: administering to the subject tonabersat.

16. The method of claim 15, wherein tonabersat is administered in an amount of about 10 mg/kg.

17. The method of claim 15, wherein the tonabersat is administered in an amount of between about 0.8 mg/kg and about 1.2 mg/kg.

18. The method of claim 15, wherein the cancer is a breast cancer or a lung cancer.

19. The method of claim 15, further comprising administering to the subject an anti-cancer agent.

20. The method of claim 19, wherein the anti-cancer agent is carboplatin.

* * * * *